(12) United States Patent
Gregory et al.

(10) Patent No.: US 12,233,077 B2
(45) Date of Patent: *Feb. 25, 2025

(54) THERAPEUTIC TREATMENT OF BREAST CANCER BASED ON c-MAF STATUS

(71) Applicant: INBIOMOTION S.L., Barcelona (ES)

(72) Inventors: Walter Martin Gregory, Ilkley (GB); Juan Carlos Tercero, Madrid (ES); Robert E. Coleman, Sheffield (GB); Roger Gomis, Barcelona (ES)

(73) Assignee: INBIOMOTION S.L., Barcelona (ES)

( * ) Notice: Subject to any disclaimer, the term of this patent is extended or adjusted under 35 U.S.C. 154(b) by 27 days.

This patent is subject to a terminal disclaimer.

(21) Appl. No.: 18/298,807

(22) Filed: Apr. 11, 2023

(65) Prior Publication Data
US 2024/0000816 A1 Jan. 4, 2024

Related U.S. Application Data

(63) Continuation of application No. 16/766,043, filed as application No. PCT/IB2018/059189 on Nov. 21, 2018, now Pat. No. 11,654,153.

(60) Provisional application No. 62/589,630, filed on Nov. 22, 2017.

(51) Int. Cl.
A61K 31/675 (2006.01)
A61K 31/663 (2006.01)
A61K 45/06 (2006.01)
A61P 35/04 (2006.01)
C07K 16/28 (2006.01)
C12Q 1/6886 (2018.01)

(52) U.S. Cl.
CPC .......... A61K 31/675 (2013.01); A61K 31/663 (2013.01); A61K 45/06 (2013.01); A61P 35/04 (2018.01); C07K 16/2875 (2013.01); C12Q 1/6886 (2013.01); C12Q 2600/158 (2013.01)

(58) Field of Classification Search
CPC .................................................. A61K 31/675
USPC ...................................................... 424/133.1
See application file for complete search history.

(56) References Cited

U.S. PATENT DOCUMENTS

| | | |
|---|---|---|
| 6,274,338 B1 | 8/2001 | Glimcher et al. |
| 6,740,522 B2 | 5/2004 | Anderson et al. |
| 7,019,028 B2 | 3/2006 | Eder et al. |
| 7,097,834 B1 | 8/2006 | Boyle |
| 7,364,736 B2 | 4/2008 | Boyle et al. |
| 7,411,050 B2 | 8/2008 | Anderson |
| 8,642,270 B2 | 2/2014 | Leyland-Jones et al. |
| 9,127,302 B2 | 9/2015 | Verrant et al. |
| 9,134,237 B2 | 9/2015 | Connelly et al. |
| 9,702,878 B2 | 7/2017 | Gomis et al. |
| 10,006,091 B2 | 6/2018 | Gomis et al. |
| 10,047,398 B2 | 8/2018 | Gomis et al. |
| 10,114,022 B2 | 10/2018 | Gomis et al. |
| 10,119,171 B2 | 11/2018 | Gomis et al. |
| 10,793,642 B2 | 10/2020 | Gomis et al. |
| 10,866,241 B2 | 12/2020 | Gomis et al. |
| 11,041,213 B2 | 6/2021 | Gomis et al. |
| 11,041,861 B2 | 6/2021 | Gomis et al. |
| 11,072,831 B2 | 7/2021 | Gomis et al. |
| 11,352,673 B2 | 6/2022 | Gomis et al. |
| 11,591,599 B2 | 2/2023 | Gomis et al. |
| 11,596,642 B2 | 3/2023 | Gregory et al. |
| 11,654,153 B2 | 5/2023 | Gregory et al. |
| 2004/0138313 A1 | 7/2004 | Eder et al. |
| 2005/0181375 A1 | 8/2005 | Aziz et al. |
| 2008/0219996 A1 | 9/2008 | Kalebic et al. |
| 2009/0029378 A1 | 1/2009 | Connelly et al. |
| 2009/0048117 A1 | 2/2009 | Glimcher et al. |
| 2009/0220955 A1 | 9/2009 | Verrant |
| 2010/0113297 A1 | 5/2010 | Lidereau et al. |
| 2010/0210738 A1 | 8/2010 | Leyland-Jones et al. |
| 2011/0130296 A1 | 6/2011 | Benz et al. |
| 2011/0150979 A1 | 6/2011 | Ray et al. |
| 2011/0152113 A1 | 6/2011 | Escudero et al. |
| 2014/0057796 A1 | 2/2014 | Gomis et al. |
| 2014/0105918 A1 | 4/2014 | Gomis et al. |
| 2014/0162887 A1 | 6/2014 | Martin et al. |
| 2014/0303133 A1 | 10/2014 | Pietenpol et al. |
| 2014/0314792 A1 | 10/2014 | Gomis et al. |
| 2015/0152506 A1 | 6/2015 | Gomis et al. |
| 2015/0293100 A1 | 10/2015 | Gomis et al. |

(Continued)

FOREIGN PATENT DOCUMENTS

| | | |
|---|---|---|
| EP | 0120694 A2 | 10/1984 |
| EP | 0125023 A1 | 11/1984 |

(Continued)

OTHER PUBLICATIONS

Abbott Molecular, "Vysis LSI IGH/MAF Dual Color Dual Fusion Probe," accessed at http://abbottmolecular.com/us/products/analyte-specific-reagent/fish/vysis-lsi-igh-maf-dual-color-dual-fusion-probe.html, accessed on Oct. 16, 2014, 2 pages.

Abnova, "MAF FISH Probe," accessed at http://abnova.com/products/products_detail.asp?Catalog_id=FA0375, accessed on Oct. 16, 2014, 2 pages.

Afinitor.com, "AFINITOR (everolimus) Tablets," accessed at http://afinitor.com/sega-tuberous-sclerosis/patient/sega-information.jsp, accessed on Oct. 16, 2014, 5 pages.

(Continued)

Primary Examiner — Sean E Aeder
(74) Attorney, Agent, or Firm — Sterne, Kessler, Goldstein & Fox P.L.L.C.

(57) ABSTRACT

The present invention relates to the design of a customized therapy for a subject with breast cancer based on the c-MAF expression level and the menopausal status of the subject. In some embodiments, the customized therapy comprises an agent for avoiding, treating or preventing bone degradation. In some embodiments, the agent for avoiding, treating or preventing bone degradation is zoledronic acid. In other embodiments, the agent is clodronate or denosumab.

22 Claims, 37 Drawing Sheets
Specification includes a Sequence Listing.

(56) References Cited

U.S. PATENT DOCUMENTS

| | | | |
|---|---|---|---|
| 2015/0362495 | A1 | 12/2015 | Gomis et al. |
| 2016/0032399 | A1 | 2/2016 | Gomis et al. |
| 2016/0032400 | A1 | 2/2016 | Gomis et al. |
| 2016/0040247 | A1 | 2/2016 | Gomis et al. |
| 2017/0002357 | A1 | 1/2017 | Gomis et al. |
| 2017/0088900 | A1 | 3/2017 | Anjamshoaa et al. |
| 2017/0101683 | A1 | 4/2017 | Gomis et al. |
| 2017/0121777 | A1 | 5/2017 | Gomis et al. |
| 2017/0369589 | A1 | 12/2017 | Gomis et al. |
| 2017/0370935 | A1 | 12/2017 | Gomis et al. |
| 2019/0119757 | A1 | 4/2019 | Gomis et al. |
| 2019/0169693 | A1 | 6/2019 | Gomis et al. |
| 2019/0242898 | A1 | 8/2019 | Gomis et al. |
| 2019/0256922 | A1 | 8/2019 | Gomis et al. |
| 2019/0269707 | A1 | 9/2019 | Gregory et al. |
| 2019/0309299 | A1 | 10/2019 | Gomis et al. |
| 2021/0137952 | A1 | 5/2021 | Gregory et al. |
| 2021/0190784 | A1 | 6/2021 | Gomis et al. |
| 2021/0317534 | A1 | 10/2021 | Gomis et al. |
| 2021/0388452 | A1 | 12/2021 | Gomis et al. |
| 2022/0042997 | A1 | 2/2022 | Gomis et al. |
| 2022/0049316 | A1 | 2/2022 | Gomis et al. |
| 2023/0323356 | A1 | 10/2023 | Gomis et al. |
| 2023/0381209 | A1 | 11/2023 | Gregory et al. |

FOREIGN PATENT DOCUMENTS

| | | |
|---|---|---|
| EP | 1961825 A1 | 8/2008 |
| EP | 2626431 A2 | 8/2013 |
| EP | 2650682 A1 | 10/2013 |
| WO | WO-9116880 A1 | 11/1991 |
| WO | WO-0055126 A2 | 9/2000 |
| WO | WO-0149288 A1 | 7/2001 |
| WO | WO-03020278 A1 | 3/2003 |
| WO | WO-03020721 A1 | 3/2003 |
| WO | WO-03059249 A2 | 7/2003 |
| WO | WO-2004000843 A1 | 12/2003 |
| WO | WO-2004014888 A1 | 2/2004 |
| WO | WO-2005029067 A2 | 3/2005 |
| WO | WO-2005046731 A1 | 5/2005 |
| WO | WO-2005063252 A1 | 7/2005 |
| WO | WO-2005086891 A2 | 9/2005 |
| WO | WO-2006012221 A2 | 2/2006 |
| WO | WO-2006135436 A2 | 12/2006 |
| WO | WO-2008098351 A1 | 8/2008 |
| WO | WO-2008104543 A2 | 9/2008 |
| WO | WO-2008142164 A2 | 11/2008 |
| WO | WO-2008145125 A1 | 12/2008 |
| WO | WO-2009045115 A1 | 4/2009 |
| WO | WO-2009049410 A1 | 4/2009 |
| WO | WO-2009146546 A1 | 12/2009 |
| WO | WO-2010000907 A1 | 1/2010 |
| WO | WO-2010136569 A1 | 12/2010 |
| WO | WO-2012045905 A2 | 4/2012 |
| WO | WO-2012125828 A2 | 9/2012 |
| WO | WO-2013153458 A2 | 10/2013 |
| WO | WO-2013182912 A2 | 12/2013 |
| WO | WO-2014057357 A2 | 4/2014 |
| WO | WO-2014140896 A2 | 9/2014 |
| WO | WO-2014140933 A2 | 9/2014 |
| WO | WO-2014184679 A2 | 11/2014 |
| WO | WO-2015052583 A2 | 4/2015 |
| WO | WO-2016092524 A1 | 6/2016 |
| WO | WO-2017203468 A1 | 11/2017 |
| WO | WO-2019102380 A1 | 5/2019 |

OTHER PUBLICATIONS

Agilent Technologies, "Probes for Chromosome 16," accessed at http://genomics.agilent.com/productSearch.jsp?chr=16&start-79483700&end-79754340&_requestid=78075, accessed on Oct. 16, 2014, 3 pages.

Al-Mulla, F., et al., "Expressive Genomic Hybridisation: Gene Expression Profiling at the Cytogenetic Level," Journal of Clinical Pathology: Molecular Pathology 56(4):210-217, BMJ Publishing Group, England (2003).

Altschul, S.F., et al., "Basic Local Alignment Search Tool," Journal of Molecular Biology 215(3):403-410, Elsevier, England (Oct. 1990).

Andrews, N.C., et al., "The Ubiquitous Subunit of Erythroid Transcription Factor NF-E2 is a Small Basic-leucine Zipper Protein Related to the v-maf Oncogene," Proceedings of the National Academy of Sciences of USA 90(24):11488-11492, National Academy of Sciences, United States (1993).

Annunziata, C.M., et al., "A Mechanistic Rationale for MEK Inhibitor Therapy in Myeloma Based on Blockade of MAF Oncogene Expression," Blood, 117(8):2396-2404, American Society of Hematology, United States (Feb. 2011).

ARUP Laboratories, "Multiple Myeloma (MM) by FISH: Detection of Prognostically Significant Genomic Aberrations in Multiple Myeloma (MM) by Fluorescence in situ Hybridization (FISH)," accessed at http://aruplab.com, accessed on Oct. 16, 2014, 2 pages.

AZURE Trial Protocol for: Coleman, R.E., et al., "Breast-Cancer Adjuvant Therapy with Zoledronic Acid," The New England Journal of Medicine 365(15):1396-1405, Massachusetts Medical Society, United States (2011), 144 pages.

Badve, S., et al. "Basal-like and Triple-negative Breast Cancers: A Critical Review with an Emphasis on the Implications for Pathologists and Oncologists," Modern Pathology 24(2):157-167, USCAP, Inc., United States (2011).

Barrett, T., et al., "NCBI GEO: Mining Tens of Millions of Expression Profiles—Database and Tools Update," Nucleic Acids Research 35(Database Issue):D760-D765, Oxford University Press, England (2007).

Baselga, J., et al., "Everolimus in Postmenopausal Hormone-Receptor-Positive Advanced Breast Cancer," The New England Journal of Medicine 366(6):520-529, Massachusetts Medical Society, United States (Feb. 2012).

Bertucci, F., et al., "How Basal are Triple-Negative Breast Cancers?," International Journal of Cancer 123(1):236-240, Wiley-Liss, United States (2008).

Bogado, C.E., et al., "Denosumab: An Update," Drugs of Today 47(8):605-613, Prous Science, United States (2011).

Bohn, O.L., et al., "Biomarker Profile in Breast Carcinomas Presenting with Bone Metastasis," International Journal of Clinical and Experimental Pathology 3(2):139-146, E-Century Publishing Corporation, United States (2010).

Bos, P.D., et al., "Genes that Mediate Breast Cancer Metastasis to the Brain," Nature 459(7249):1005-1009, Nature Publishing Group, England (2009).

Bowles, D.W., et al., "Abstract: Multi-targeted Tyrosine Kinase Inhibitors in Clinical Development: Focus on X1-184 (Cabozantinib)," Drugs of today (Barcelona, Spain) 47(11) :857-868, Clarivate Analytics, Spain (Nov. 2011), 1 page.

Brufsky, A.M., "The Evolving Role of Bone-Conserving Therapy in Patients with Breast Cancer," Seminars in Oncology 37(Suppl 1):S12-S19, W.B. Saunders, United States (Jun. 2010).

Bruland Ø.S., et al., "High-Linear Energy Transfer Irradiation Targeted to Skeletal Metastases By the Alpha-emitter 223Ra: Adjuvant or Alternative to Conventional Modalities?," Clinical Cancer Research 12 (20 Pt 2):6250s-6257s, American Association for Cancer Research, Denville, NJ (Oct. 2006).

Cancer Genome Atlas Network, "Comprehensive Molecular Portraits of Human Breast Tumors," Nature 490(7418):61-70, Nature Publishing Group, England (2012).

Carey, L.A., "Triple-Negative (basal-like) Breast Cancer: A New Entity," Breast Cancer Research 9(Suppl1):S13,, 24 pages, BioMed Central Ltd., England (2007).

CGI Italia, "IGH/MAF Two Color, Two Fusion Translocation Probe," accessed at http://cancergeneticsitalia.com/dna-fish-probe/ighmaf/, accessed on Oct. 16, 2014, 1 page.

Choi, M., et al., "Genetic Diagnosis by Whole Exome Capture and Massively Parallel DNA Sequencing," Proceedings of the National Academy of Sciences of USA 106(45):19096-19101, National Academy of Sciences, United States (2009).

(56) References Cited

OTHER PUBLICATIONS

Clinicaltrials.gov, "Study of Denosumab as Adjuvant Treatment for Women With High Risk Early Breast Cancer Receiving Neoadjuvant or Adjuvant Therapy (D-CARE)," Identifier NCT01077154, accessed at https://clinicaltrials.gov/ct2/show/NCT01077154, last accessed on Aug. 25, 2017, 6 pages.
Coleman, R., "Abstract P1-09-01: Impact of MAF Gene Amplification on Disease Recurrence and Effects of Adjuvant Zoledronic Acid in Early Breast Cancer," Cancer Research 77(4), 2 pages (Feb. 2017), 103rd Annual Meeting of the American Association-For-Cancer-Research, Chicago, IL, USA, Mar. 31-Apr. 4, 2012, including supplemental data.
Coleman, R., et al., "Adjuvant Zoledronic Acid in Patients with Early Breast Cancer: Final Efficacy Analysis of the Azure (Big 01/04) Randomised Open-label Phase 3 Trial," The Lancet Oncology 15(9):997-1006, 10 pages, Lancet Publishing Group, England (Jul. 2014).
Coleman, R., et al., "Effect of MAF Amplification on Treatment Outcomes with Adjuvant Zoledronic Acid in Early Breast Cancer: A Secondary Analysis of the International, Open-Label, Randomised, Controlled, Phase 3 Azure (Big 01/04) Trial," The Lancet Oncology 18(11):1543-1552, 10 pages, Lancet Publication, England (Nov. 2017).
Coleman, R.E., et al., "Benefits and risks of adjuvant treatment with zoledronic acid in stage II/III breast cancer. 10 years follow-up of the AZURE randomized clinical trial (BIG 01/04)," Journal of Bone Oncology, 13(1):123-135, Elsevier (Sep. 2018).
Coleman, R.E., et al., "Breast-Cancer Adjuvant Therapy with Zoledronic Acid," The New England Journal of Medicine 365(15):1396-1405, Massachusetts Medical Society, United States (Oct. 2011), with Supplementary Appendix, 18 pages.
Co-pending Application, U.S. Appl. No. 15/944,510, inventors Gomis R., et al., filed Apr. 3, 2018 (Not Published).
Co-pending Application, U.S. Appl. No. 15/955,790, Inventors Gomis, R., et al., filed Apr. 18, 2018 (Not Published).
Costa, L and Ferreira, A.R., "Adjuvant zoledronic acid to treat breast cancer: not for all," The Lancet Oncology, 18(11):1437-1439, The Lancet Publishing Group, England (Nov. 2017).
Creative Bioarray, "Products," accessed at http://creative-bioarray.com/Products.htm, accessed on Oct. 16, 2014, 2 pages.
Curtis, C., et al., "The Genomic and Transcriptomic Architecture of 2,000 Breast Tumours Reveals Novel Subgroups," Nature 486(7403):346-352, Nature Publishing Group, England (2012).
Cytocell, "Oncology and Constitutional FISH Probe Catalogue 2012/2013," accessed at http://zentech.be/uploads/docs/products_info/prenatalogy/cytocell%202012-2013%20catalogue%5B3%5D.pdf, accessed on Oct. 16, 2014, 134 pages.
Dako Denmark A/S, "HER2 IQFISH pharmDx™, Code K5731," Assay Information, 3rd edition, 184 pages.
Dako, "SureFISH Probes," accessed at http://dako.com/us/ar42/psg42806000/baseproducts_surefish.htm?setCountry=true&purl=ar42/psg42806000/baseproducts_surefish.htm?undefined&submit=Accept%20country, accessed on Oct. 16, 2014, 2 pages.
Dannhardt, G. and Kiefer, W., "Cyclooxygenase Inhibitors—Current Status and Future Prospects," European Journal of Medicinal Chemistry 36(2):109-126, Editions Scientifiques et Medicales Elsevier SAS, France (2001).
Dean-Colomb, W., et al., "Elevated Serum PINP Predicts Development of Bone Metastasis and Survival in Early-Stage Breast Cancer," Breast Cancer Research and Treatment 137(2):631-636, Springer Science+Business Media, United States (2013).
Demarest, J.F., et al., "Update on Aplaviroc: An HIV Entry Inhibitor Targeting CCR5," Retrovirology 2(Suppl 1):S13, 1 page, BioMed Central, England (2005).
Dhesy-Thind, S., et al., "Use of Adjuvant Bisphosphonates and Other Bone-Modifying Agents in Breast Cancer: A Cancer Care Ontario and American Society of Clinical Oncology Clinical Practice Guideline," J Clin Oncol 35, American Society of Clinical Oncology, United States, 22 pages (Mar. 6, 2017).

Early Breast Cancer Trialists' Collaborative Group (EBCTCG), "Adjuvant Bisphosphonate Treatment in Early Breast Cancer: Meta-analyses of Individual Patient Data From Randomised Trials," Lancet 386(10001):1353-1361, Elsevier, England (2015).
Ettenberg, S.A., et al., "BHQ880, A Novel Anti-DKK1 Neutralizing Antibody, Inhibits Tumor-Induced Osteolytic Bone Disease," Proceedings of the American Association for Cancer Resaerch 49:947, Abstract 3987, American Association for Cancer Research, United States (2008).
Extended European Search Report for EP Application No. 12382139.9, European Patent Office, Munich, Germany, dated Sep. 20, 2012, 8 pages.
Extended European Search Report for EP Application No. 15180897.9, European Patent Office, Munich, Germany, mailed Sep. 29, 2016, 9 pages.
Extended European Search Report for EP Application No. 19165007.6, The Hague, Netherlands, mailed on May 22, 2019.
Extended European Search Report for Application No. 19159414.2, mailed on Jun. 13, 2019, 10 pages.
Eychene, A., et al., "A New MAFia in Cancer," Nature Reviews Cancer 8(9):683-693, Nature Publishing Group, England (2008).
Fili, S., et al., "Therapeutic Implications of Osteoprotegerin," Cancer Cell International 9:26:1-8, BioMed Central Ltd., England (2009).
Finn, R.S., et al., "Targeting the Cyclin-dependent Kinases (CDK) 4/6 in Estrogen Receptor-positive Breast Cancers," Breast Cancer Research 18(1):17, BioMed Central Ltd., England, 11 pages (2016).
Fornier, M.N., et al., "Phase I Dose-finding Study of Weekly Docetaxel Followed by Flavopiridol for Patients with Advanced Solid Tumors," Clinical Cancer Research 13(19):5841-5846, The Association, United States (Oct. 2007).
Fujiwara, K.T., et al., "Two New Members of the maf Oncogene Family, mafK and mafF, Encode Nuclear b-Zip Proteins Lacking Putative Trans-Activator Domain," Oncogene 8(9):2371-2380, Nature Publishing Group, England (1993).
GenBank Database, "*Homo sapiens* Chromosome 16 Genomic Contig, GRCh37.p10 Primary Assembly," NCBI Reference Sequence Accession No. NT_010498, accessed at https://www.ncbi.nlm.nih.gov/nuccore/NT_010498.15, accessed on Jun. 20, 2013, 5 pages.
GenBank Database, "*Homo sapiens* Chromosome 16 Genomic Contig, GRCh37.p10 Primary Assembly," NCBI Reference Sequence Accession No. NT_010542.15, accessed at http://www.ncbi.nlm.nih.gov/nuccore/NT_010542.15, accessed on Jun. 20, 2013, 2 pages.
GenBank Database, "*Homo sapiens* v-maf avian musculoaponeurotic fibrosarcoma oncogene homolog (MAF), RefSeqGene on chromosome 16," NCBI Reference Sequence Accession No. NG_016440.1, accessed at http://www.ncbi.nlm.nih.gov/nuccore/NG_016440, accessed on Apr. 3, 2015, 5 pages.
GenBank Database, "*Homo sapiens* v-maf avian musculoaponeurotic fibrosarcoma oncogene homolog (MAF), transcript variant 1, mRNA," NCBI Reference Sequence Accession No. NM_005360.4, accessed at http://www.ncbi.nlm.nih.gov/nuccore/NM_005360.4, accessed on Apr. 3, 2015, 5 pages.
GenBank Database, "*Homo sapiens* v-maf avian musculoaponeurotic fibrosarcoma oncogene homolog (MAF), transcript variant 2, mRNA," NCBI Reference Sequence Accession No. NM_001031804.2, accessed at http://www.ncbi.nlm.nih.gov/nuccore/NM_001031804.2, accessed on Apr. 3, 2015, 6 pages.
Gene Expression Omnibus Database, Accession No. GSE 12276, made public on Jun. 13, 2009, accessed at http://www.ncbi.nlm.nih.gov/geo/query/acc.cgi?acc=GSE12276, accessed on Jun. 20, 2013, 2 pages.
Gene Expression Omnibus Database, Accession No. GSE 14020, made public on May 1, 2009, accessed at http://www.ncbi.nlm.nih.gov/geo/query/acc.cgi?acc=GSE14020, accessed on Jun. 20, 2013, 2 pages.
Gene Expression Omnibus Database, Accession No. GSE 2034, made public on Feb. 23, 2005, accessed at http://www.ncbi.nlm.nih.gov/geo/query/acc/cgi?acc=GSE+2034, accessed on Jun. 20, 2013, 7 pages.

(56) References Cited

OTHER PUBLICATIONS

Gene Expression Omnibus Database, Accession No. GSE 2603, made public on Jul. 28, 2005, accessed at http://www.ncbi.nlm.nih.gov/geo/query/acc/cgi?acc=GSE+2603, accessed on Jun. 20, 2013, 2 pages.
GenPept Database, "RecName: Full-Transcription Factor Maf; AltName: Full=Proto-oncogene c-Maf; AltName: Full=V-maf Musculoaponeurotic Fibrosarcoma Oncogene Homolog [*Homo sapiens*]," UniProtKB/Swiss-Prot: Accession No. 075444.2, accessed at https://www.ncbi.nlm.nih.gov/protein/o75444, accessed on Apr. 3, 2015, 6 pages.
GenPept Database, "transcription factor Maf isoform a [*Homo sapiens*]" NCBI Reference Sequence Accession No. NP_005351.2, accessed at http://www.ncbi.nlm.nih.gov/protein/NP_005351.2, accessed on Apr. 3, 2015, 4 pages.
GenPept Database, "transcription factor Maf isoform b [*Homo sapiens*]" NCBI Reference Sequence Accession No. NP_001026974.1, accessed at http://www.ncbi.nlm.nih.gov/protein/NP_001026974, accessed on Apr. 3, 2015, 4 pages.
Gentleman, R.C., et al., "Bioconductor: Open Software Development for Computational Biology and Bioinformatics," Genome Biology 5(10):R80, 16 pages, BioMed Central Ltd, England (2004).
Genycell Biotech, "FISH Mieloma Multiple," accessed at http://google.com/url?sa=t&rct=j&q=&esrc=s&source=web&cd=1&ved=CCQQFjAA&url=http%3A%2F%2Fwww.genycell.es%2Fimages%2Fproductos%2Fbrochures%2Flphmie6_86.ppt&ei=MhFYUOi3GKWH0QGlt4DoDw&usg=AFQjCNEqQMbT8vQGjJbi9riEf31VgoFTFQ&sig2=V5IS8juEMVHB18Mv2Xx_Ww, accessed on Oct. 16, 2014, 1 page.
Giancotti, V., "Breast Cancer Markers," Cancer Letters, 243(2):145-159, Elsevier Ireland Ltd., Ireland (2006).
Gnant, M., et al., "Adjuvant Bisphosphonates in Endocrine-responsive Breast Cancer: What is their Place in Therapy?" Therapeutic Advances in Medical Oncology 1(3):123-136, Sage, England (2009).
Gnant, M., et al., "Adjuvant Denosumab in Breast Cancer (ABCSG-18): a Multicentre, Randomised, Double-Blind, Placebo-Controlled Trial," Lancet, 386(9992):433-443, Elsevier, England (Aug. 2015).
Gnant, M., et al., "Adjuvant Endocrine Therapy Plus Zoledronic Acid in Premenopausal Women With Early-stage Breast Cancer: 62-month Follow-up From the ABCSG-12 Randomised Trial," The Lancet Oncology 12(7):631-641, Lancet Pub. Group, England (Jul. 2011).
Goss, P.E., and Chambers, A.F., "Does Tumour Dormancy Offer a Therapeutic Target?," Nature Reviews. Cancer 10(12):871-877, Macmillan Publishers Ltd., England (2010).
Gralow, J., et al., "Phase III Trial of Bisphosphonates as Adjuvant Therapy in Primary Breast Cancer: SWOG/Alliance/ECOG-ACRIN/NCIC Clinical Trials Group/NRG Oncology Study S0307," ASCO meeting library, accessed at https://meetinglibrary.asco.org/record/111882/abstract, accessed on Jul. 26, 2018, 2 pages.
Gur-Dedeoglu, B., et al., "A Resampling-Based Meta-Analysis for Detection of Differential Gene Expression in Breast Cancer," BMC Cancer 8:396, 16pages, BioMed Central Ltd, England (2008).
Haas, M.J., "RANKLing Non-skeletal Tumors," SciBX, Nature Publishing Group, 2 pages (2010).
Hadji, P., et al., "Adjuvant Bisphosphonates in Early Breast Cancer: Consensus Guidance for Clinical Practice From a European Panel," Annals of Oncology 27(3):379-390, Oxford University Press, England (2016).
Hammond, M.E.H., et al., "American Society of Clinical Oncology/College of American Pathologists Guideline Recommendations for Immunohistochemical Testing of Estrogen and Progesterone Receptors in Breast Cancer," Journal of Clinical Oncology 28(16):2784-2795, American Society of Clinical Oncology, United States (2010).
Henry, D.H., et al., "Randomized, Double-Blind Study of Denosumab Versus Zoledronic Acid in the Treatment of Bone Metastases in Patients with Advanced Cancer (Excluding Breast and Prostate Cancer) or Multiple Myeloma," Journal of Clinical Oncology 29(9):1125-1132, American Society of Clinical Oncology, United States (2011).
Hiraga, T., "Role of Cyclooxygenase-2 in the Bone Metastasis of the Breast Cancer [Nyugan No Honeteni Ni Okeru Shikurookishigenaze-2 No Yakuwari]," Bone 20(5):563-566, Japan (2006).
Horlings, H.M., et al., "Integration of DNA Copy Number Alterations and Prognostic Gene Expression Signatures in Breast Cancer Patients," Clinical Cancer Research, 16(2):651-663, American Association for Cancer Research, United States (Jan. 2010).
Hospira Healthcare Corporation, "Prescribing Information: Zoledronic Acid for Injection, 4 mg/5 mL (0.8 mg/mL), zoledronic acid (as zoledronic acid monohydrate)," Control No. 182128, prepared May 4, 2015, accessed at https://www.hospira.ca/en/images/2015.05.04%20Zoledronic%20Acid%204%20mg%20Eng%20PI_tcm87-97657.PDF, 32 pages.
Hu, G., et al., "MTDH Activation by 8q22 Genomic Gain Promotes Chemoresistance and Metastasis of Poor-Prognosis Breast Cancer," Cancer Cell 15(1):9-20, Cell Press, United States (2009).
Huang, Q. and Ouyang, X., "Biochemical-Markers for the Diagnosis of Bone Metastasis: A Clinical Review," Cancer Epidemiology 36(1):94-98, Elsevier Ltd., Netherlands (2012).
Huober J and Thurlimann B, "Bone Targeted Therapy in Breast Cancer: Present and Future," Critical Reviews in Oncology/Hematology 74 Suppl 1:S7-S10, Elsevier Scientific Publishers, Netherlands (Apr. 2010).
Hurt, E.M., et al., "Overexpression of c-maf is a Frequent Oncogenic Event in Multiple Myeloma that Promotes Proliferation and Pathological Interactions with Bone Marrow Stroma," Cancer Cell 5(2):191-199, Cell Press, United States (Feb. 2004).
Igarashi, K., et al., "Activity and Expression of Murine Small Maf Family Protein MafK," The Journal of Biological Chemistry 270(13):7615-7624, The American Society for Biochemistry and Molecular Biology, Inc., United States (1995).
International Preliminary Report on Patentability for Application No. PCT/ES2011/070693, International Bureau of WIPO, Sweden, mailed on Apr. 9, 2013, 8 pages.
International Preliminary Report on Patentability for Application No. PCT/IB2013/001204, European Patent Office, Rijswijk, Netherlands, mailed on Aug. 11, 2014, 12 pages.
International Preliminary Report on Patentability for Application No. PCT/IB2017/053094, mailed on Sep. 3, 2018, 11 pages.
International Preliminary Report on Patentability for International Application No. PCT/IB2014/002675, The International Bureau of WIPO, Geneva, Switzerland, issued Apr. 12, 2016, 12 pages.
International Search Report and Written Opinion for Application No. PCT/ES2011/070693, European Patent Office, Netherlands, mailed on Apr. 2, 2012, 12 pages.
International Search Report and Written Opinion for Application No. PCT/IB2013/001204, European Patent Office, Rijswijk, Netherlands, mailed on Dec. 17, 2013, 11 pages.
International Search Report and Written Opinion for Application No. PCT/IB2018/059189, mailed on May 7, 2019, 32 pages.
International Search Report and Written Opinion for International Application No. PCT/IB2014/002675, mailed on Jun. 3, 2015, 17 pages.
International Search Report and Written Opinion for International Application No. PCT/IB2017/053094, European Patent Office, Rijswijk, mailed on Aug. 14, 2017, 19 pages.
Johnson, K., "Denosumab Boosts Survival, Not Just Bones, in Breast Cancer, "Medscape, Retrieved on [Apr. 23, 2019], Dec. 10, 2015, 1 page, Retrieved From the Internet: (URL: https://www.medscape.com/viewarticle/855803).
Kang, Y., et al., "A Multigenic Program Mediating Breast Cancer Metastasis to Bone," Cancer Cell 3(6):537-549, Cell Press, United States (2003).
Kataoka, K., et al., "Small Maf Proteins Heterodimerize with Fos and May Act as Competitive Repressors of the NF-E2 Transcription Factor," Molecular and Cellular Biology 15(4):2180-2190, American Society for Microbiology, United States (1995).
Kataoka, K., et al., "Transactivation Activity of Maf Nuclear Oncoprotein is Modulated by Jun, Fos and Small Maf Proteins," Oncogene 12:53-62, Stockton Press, England (1996).

(56) References Cited

OTHER PUBLICATIONS

Kharaishvili, G., et al., "Collagen Triple Helix Repeat Containing 1 Protein, Periostin and Versican in Primary and Metastatic Breast Cancer: An Immunohistochemical Study," Journal of Clinical Pathology 64(11):977-982, BMJ Publishing Group, England (2011).
Kim, H., et al., "Multi-cancer Computational Analysis Reveals Invasion-associated Variant of Desmoplastic Reaction Involving INHBA, THBS2 and COL11A1," BMC Medical Genomics 3:51, 11 pages, BioMed Central, England (Nov. 2010).
Klopocki, E. and Mundlos, S., "Copy-number Variations, Noncoding Sequences, and Human Phenotypes," Annual Review of Genomics and Human Genetics 12:53-72, Annual Reviews, United States (2011).
Knight III, W.A., et al., "Estrogen Receptor as an Independent Prognostic Factor for Early Recurrence in Breast Cancer," Cancer Research 37(12):4669-4671, American Association for Cancer Research, United States (1977).
Kohler, G. and Milstein, C., "Continuous Cultures of Fused Cells Secreting Antibody of Predefined Specificity," Nature 256(5517):495-497, Macmillan Journals Ltd., England (Aug. 1975).
Kuritzkes, D.R., "HIV-1 Entry Inhibitors: An Overview," Current Opinion in HIV and AIDS 4(2):82-87, Lippincott Williams & Wilkins, United States (2009).
Largo, C., et al., "Identification of Overexpressed Genes in Frequently Gained/Amplified Chromosome Regions in Multiple Myeloma," Haematologica 91(2):184-191, Ferrata Storti Foundation, Italy (2006).
Leica Biosystems, "Kreatech™MFISH Probes," accessed at http://leicabiosystems.com/ihc-ish/kreatech-fish-probes/, accessed on Oct. 16, 2014, 2 pages.
Liao, S., et al., "Identification of New Breast Cancer Candidate Genes Associated with Stromal Invasion," Cancer Research, Abstract #4036, 69(2 Suppl), (Jan. 2009), Retrieved from the Internet http://cancerres.aacrjournals.org/content/69/2_Supplement/4036, 4 pages.
Liepe, K, "Abstract: Alpharadin, a 223Ra-based Alpha-particle-emitting Pharmaceutical for the Treatment of Bone Metastases in Patients With Cancer," Current Opinion in Investigational Drugs 10(12):1346-1358, Thomson Reuters (Scientific) Ltd, England (Dec. 2009), 2 pages.
Lipton, A., et al., "The science and practice of bone health in oncology: managing bone loss and metastasis in patients with solid tumors," J Natl Compr Canc Netw 7(Suppl 7):S1-30, Jones and Bartlett Publishers, United States (2009).
Maisano, R., et al., "Novel Therapeutic Approaches to Cancer Patients with Bone Metastasis," Critical Reviews in Oncology/Hematology 40(3):239-250, Elsevier Science Ireland Ltd., Ireland (2001).
MetaSystems, "24XCyte," acessed at http://metasystems-international.com/index.php?option=com_joodb&view=article&joobase=5*id=12%3Ad-5029-100-og&Itemid=272, accessed on Oct. 16, 2014, 2 pages.
Ministry of Health, Social Services and Equality, Data Sheet of "Zoledronic acid Kern Pharma 4 mg/100 mL Solution for Infusion EFG," Text Revised Jul. 2016, Machine-translated Jul. 6, 2017, 38 pages (Ministerio de Sanidad, Servicios Sociales e Igualdad, Ficha Tecnica de "Acido Zoledronico Kern Pharma 4 mg/100 ml Solucion Para Perfusion EFG").
Morito, N., et al., "Overexpression of c-Maf Contributes to T-Cell Lymphoma in Both Mice and Human, "Cancer Research 66(2):812-819, American Association for Cancer Research, Japan (Jan. 2006).
Mystakidou, K., et al., "Randomized, Open Label, Prospective Study on the Effect of Zoledronic Acid on the Prevention of Bone Metastases in Patients with Recurrent Solid Tumors That Did Not Present with Bone Metastases at Baseline," Medical Oncology 22(2):195-201, Humana Press Inc., United States (2005).
Nakashima, T., et al., "New Molecular and Biological Mechanism of Antitumor Activities of KW-2478, a Novel Nonansamycin Heat Shock Protein 90 Inhibitor, in Multiple Myeloma Cells," Clinical Cancer Research 16(10):2792-2802, American Association for Cancer Research, United States (May 2010).

Neville-Webbe H.L. and Coleman R.E., "Bisphosphonates and RANK Ligand Inhibitors for the Treatment and Prevention of Metastatic Bone Disease," European Journal of Cancer 46(7):1211-1222, Elsevier Science Ltd., England (2010).
Ng, P.C. and Kirkness, E.F., "Whole Genome Sequencing," in Genetic Variation: Methods and Protocols, pp. 215-226, Springer Science+Business Media, LLC, Netherlands (2010).
Nguyen, D.X. and Massague, J., "Genetic Determinants of Cancer Metastasis," Nature Reviews Genetics 8(5):341-352, Nature Publishing Group, England (May 2007).
Nguyen, D.X., et al., "Metastasis: From Dissemination to Organ-Specific Colonization," Nature Reviews Cancer 9(4):274-284, Macmillan Publishers Limited, England (Apr. 2009).
Pageau, S.C., "Denosumab," mAbs 1(3):210-215, Landes Bioscience, United States (May-Jun. 2009).
Paik, S., et al., "A Multigene Assay to Predict Recurrence of Tamoxifen-Treated, Node-Negative Breast Cancer," The New England Journal of Medicine 351(27):2817-2826, Massachusetts Medical Society, United States (2004).
Paterson, A.H., et al., "Oral Clodronate for Adjuvant Treatment of Operable Breast Cancer (National Surgical Adjuvant Breast and Bowel Project protocol B-34): A Multicentre, Placebo-controlled, Randomised Trial," The Lancet Oncology 13(7):734-742, Lancet Pub. Group, England (Jul. 2012).
Paterson, A.H.G. and Shea-Budgell, M.A., "Bone Health in Patients with Breast Cancer: Recommendations from an Evidence-Based Canadian Guideline," Journal of Clinical Medicine 2(4):283-301, MDPI AG, Switzerland (2013).
Pavlovic, M., et al., "Enhanced MAF Oncogene Expression and Breast Cancer Bone Metastasis," Journal of the National Cancer Institute 107(12):djv256:1-12, Oxford University Press, United States (Sep. 2015), with Supplementary Materials and Methods, Cell Culture, Supplementary Table 1-5, 40 pages.
Polascik, T.J., "Bisphosphonates in Oncology: Evidence for the Prevention of Skeletal Events in Patients with Bone Metastases," Drug Design, Development and Therapy 3:27-40, Dove Medical Press Ltd., New Zealand (2009).
Pollack, J.R., et al., "Microarray Analysis Reveals a Major Direct Role of DNA Copy Number Alteration in the Transcriptional Program of Human Breast Tumors," Proceedings of the National Academy of Sciences of USA 99(20):12963-12968, National Academy of Sciences, United States (2002).
Rocques, N., et al., "GSK-3-Mediated Phosphorylation Enhances Maf-Transforming Activity," Molecular Cell 28(4):584-597, Cell Press, United States (2007).
Rojo, F., et al., "Nuclear PARP-1 Protein Overexpression is Associated with Poor Overall Survival in Early Breast Cancer," Annals of Oncology 23(5):1156-1164, Oxford University Press, England (2012).
Rotstein, D.M., et al., "Spiropiperidine CCR5 Antagonists," Bioorganic and Medicinal Chemistry Letters 19(18):5401-5406, Elsevier Ltd., England (2009).
Santana-Codina, N., et al., "A Transcriptome-proteome Integrated Network Identifies Endoplasmic Reticulum Thiol Oxidoreductase (ERp57) as a Hub that Mediates Bone Metastasis," Molecular and Cellular Proteomics 12(8):2111-2125, The American Society for Biochemistry and Molecular Biology, Inc., United States (2013).
Sen, B. and Johnson, F.M., "Regulation of SRC Family Kinases in Human Cancers," Journal of Signal Transduction 2011(865819):1-14, Hindawi Publishing Corporation, United States (Apr. 2011).
Stein, C.A. and Cohen, J.S., "Oligodeoxynucleotides as Inhibitors of Gene Expression: a Review," Cancer Research 48(10):2659-2668, American Association for Cancer Research, United States (1988).
Stopeck, A.T., et al., "Denosumab Compared with Zoledronic Acid for the Treatment of Bone Metastases in Patients with Advanced Breast Cancer: A Randomized, Double-Blind Study," Journal of Clinical Oncology 28(35): 5132-5139, Alexandria, American Society of Clinical Oncology, United States (2010).
Supplementary Appendix for: Coleman, R.E., et al., "Breast-Cancer Adjuvant Therapy with Zoledronic Acid," The New England Journal of Medicine 365(15):1396-1405, Massachusetts Medical Society, United States (2011), 18 pages.

(56) References Cited

OTHER PUBLICATIONS

Sutherland, R.L., et al., "Expression and Regulation of Cyclin Genes in Breast Cancer," Acta Oncologica 34(5):651-656, Scandinavian University Press, England (1995).

Swennenhuis, J.F., et al., "Construction of Repeat-Free Fluorescence in situ Hybridization Probes," Nucleic Acids Research 40(3):e20:1-8, Oxford University Press, England (Nov. 2011).

Takahashi, S., "Anti-RANKL Antibody for Treatment of Patients with Bone Metastasis from Breast Cancer," Gan To Kagaku Ryoho [Jpn J Cancer Chemother] 39(1):89-94, Gan To Kagaku Ryohosha, Tokyo, Japan (2012).

Thery, C., et al., "Isolation and Characterization of Exosomes from Cell Culture Supernatants and Biological Fluids," Current Protocols in Cell Biology Chapter 3:3.22.1-3.22.29, 29 pages, Oxford University Press, England (2006).

ZOMETA®, "About ZOMETA® (zoledronic acid) 4 mg/5 mL Injection," accessed at http://www.us.zometa.com/index.jsp?usertrack.filter_applied=true&NovaId=29353769344676433633, accessed on Apr. 3, 2015, 2 pages.

Van de Wetering de Rooij, J., et al., "Safety, Pharmacokinetics and Efficacy of Anti-Rankl Nanobody® Alx-0141 in Healthy Postmenopausal Women," Annals of the Rheumatic Diseases 70(Suppl. 3):136, 2 pages, 2011 (Abstract).

Velasco-Velazquez, M., et al., "CCR5 Antagonist Blocks Metastasis of Basal Breast Cancer Cells," Cancer Research 72(15):3839-3850, American Association for Cancer Research, United States (Aug. 2012).

Washam, C.L., et al., "Identification of PTHrP(12-48) as a Plasma Biomarker Associated with Breast Cancer Bone Metastasis," Cancer Epidemiology, Biomarkers and Prevention 22(5):972-983, American Association for Cancer Research, United States (2013).

Weber-Mangal, S., et al., "Breast Cancer in Young Women (≤35 years): Genomic Aberrations Detected by Comparative Genomic Hybridization," International Journal of Cancer 107(4):583-592, Wiley-Liss, Inc., United States (2003).

Winer, E.P., et al., "Activity of Cabozantinib (XL184) in Metastatic Breast Cancer (MBC): Results From a Phase 2 Randomized Discontinuation Trial (RDT)," Poster, 1 page, Annual Meeting of the American Society of Clinical Oncology, Chicago, United States (Jun. 1-5, 2012).

Yakes F.M., et al., "Cabozantinib (XL 184), a Novel MET and VEGFR2 Inhibitor Simultaneously Suppresses Metastasis, Angiogenesis, and Tumor Growth," Molecular Cancer Therapeutics 10(12):2298-2308, American Association for Cancer Research, Inc., Philadelphia, PA (Dec. 2011).

Yersal, O and Barutca, S., "Biological Subtypes of Breast Cancer: Prognostic and Therapeutic Implications," World Journal of Clinical Oncology, 5(3):412-424, Baishideng Publishing Group, United States (Aug. 2014).

Zeiss, "Fish Probes: XL Haematology," accessed at https://microshop.zeiss.com/?440675675dedc6&1=en&p-uk&f=r&i=5000&0=&h=25&n=1&sd=000000-528-231-uk, accessed on Oct. 16, 2014, 3 pages.

Zhang, X. H.-F., et al., "Latent Bone Metastasis in Breast Cancer Tied to Src-Dependent Survival Signals," Cancer Cell 16(1):67-78, Cell Press, United States (2009).

Zhou, H., et al., "Updates of mTOR Inhibitors," Anticancer Agents in Medicinal Chemistry 10(7):571-581, Bentham Science Publishers, Netherlands (2010).

Amit, A.G., et al., "Three-Dimensional Structure of an Antigen-Antibody Complex at 2.8 A Resolution," Science 233(4765):747-753, American Association for the Advancement of Science, United States (1986).

Baker, S.G., "The Central Role of Receiver Operating Characteristic (ROC) Curves in Evaluating Tests for the Early Detection of Cancer," Journal of the National Cancer Institute 95(7):511-515, Oxford University Press, England (2003).

Caton, A.J., et al., "Identical D Region Sequences Expressed by Murine Monoclonal Antibodies Specific for a Human Tumor-associated Antigen," Journal of Immunology 144(5):1965-1968, American Association of Immunologists, United States (Mar. 1990).

Chothia, C. and Lesk, A.M., "Canonical Structures for the Hypervariable Regions of Immunoglobulins," Journal of Molecular Biology 196(4):901-917, Elsevier Science, United States (Aug. 1987).

Chothia, C., et al., "Conformations of Immunoglobulin Hypervariable Regions," Nature 342(6252):877-883, Nature Publishing Group, England (Dec. 1989).

Creative Bioarray, "IGH/MAF Translocation, Dual Fusion Probe," accessed at http://www.creative-bioarray.com/IGH-MAF-Translocation,-Dual-Fusion-Probe-FHPC-066-item-4707.htm, accessed on May 21, 2015, 2 pages.

Deeks, E.D., and Perry, C.M., "Zoledronic Acid: A Review of Its Use In The Treatment of Osteoporosis", Drugs Aging, 25(11):963-986, Springerlink, Germany (2008).

Drake, M. T., et al., "Bisphosphonates: mechanism of action and role in clinical practice," Mayo Clin Proc 83(9):1032-1045, Elsevier, Netherlands (Sep. 2008).

Gralow, J. R., et al., "Phase III Randomized Trial of Bisphosphonates as Adjuvant Therapy in Breast Cancer: S0307," J Natl Cancer Inst 112(7):698-707, Oxford University Press, United Kingdom (Jul. 2020).

Haas, D, "On the Expanding, Then Contracting Scope of Scientific Publications," FEMS Microbiology Reviews 34(1):1-2, Oxford University Press, England (Jan. 2010).

Holliger, P, and Hudson, P.J., "Engineered Antibody Fragments and the Rise of Single Domains," Nature Biotechnology 23(9):1126-1136, Nature America Publishing, United States (2005).

Paterson, A.H.G., et al., "Validation of MAF Biomarker for Response Prediction to Adjuvant Bisphosphonates in 2 Clinical Trials: AZURE and NSABP-B34," Journal of Clinical Oncology 38(15_suppl):513-513, American Society of Clinical Oncology, United States (May 2020).

Paterson, A. H. G., et al., "MAF Amplification and Adjuvant Clodronate Outcomes in Early-Stage Breast Cancer in NSABP B-34 and Potential Impact on Clinical Practice," JNCI Cancer Spectr 5(4):pkab054, Oxford University Press, United Kingdom (May 2021), 8 pages.

Reis-Filho, J. S., "Triple Negative and Basal-like Breast Cancer: One or Many diseases? Implications for surgical Pathologists," accessed at https://web.archive.org/web/20130319192034/http://www.uscap.org/site~/98th/pdf/companion03h03.pdf on Aug. 29, 2019, 19 pages, United States & Canadian Academy of Pathology, United States (2009).

Segal, D.M., et al., "The Three-dimensional Structure of a Phosphorylcholine-binding Mouse Immunoglobulin Fab and the Nature of the Antigen Binding Site," Proc Natl Acad Sci USA 71(11):4298-4302, National Academy of Sciences, United States (Nov. 1974).

Sharon, J., "Structural Characterization of Idiotopes by Using Antibody Variants Generated by Site-directed Mutagenesis," Journal of Immunology 144(12):4863-4869, American Association of Immunologists, United States (Jun. 1990).

Sharon, J., "Structural Correlates of High Antibody Affinity: Three Engineered Amino Acid Substitutions Can Increase the Affinity of an Anti-p-azophenylarsonate Antibody 200-fold," Proc Natl Acad Sci USA 87(12):4814-4817, National Academy of Sciences, United States (Jun. 1990).

Viprey, V.F., et al., "Neuroblastoma mRNAs Predict Outcome in Children With Stage 4 Neuroblastoma: A European HR-NBL1/SIOPEN Study," Journal of Clinical Oncology, 32(10):1074-1083, American Society of Clinical Oncology, United States (Apr. 2014).

Zefei, J., et al., "Expert Consensus on Clinical Diagnosis and Treatment of Breast Cancer Bone Metastasis and Bone-related Diseases (2014 Edition)," Chinese Medical Journal, 95(4):241-247, (Jan. 2015).

Zhao, X, and Hu, X., "Dosing of Zoledronic Acid with its Anti-Tumor Effects in Breast Cancer," Journal of Bone Oncology 4(3):98-101, Elsevier, Netherlands. (Oct. 2015).

Rosen, L., et al., "Zoledronic acid is superior to pamidronate for the treatment of bone metastases in breast carcinoma patients with at least one osteolytic lesion," Cancer 100(1):36-43, Wiley, United States (Jan. 2004).

(56) References Cited

OTHER PUBLICATIONS

Kristensen, B., et al., "Oral clodronate in breast cancer patients with bone metastases: a randomized study," J Intern Med 246(1):67-74, Wiley, United States (Jul. 1999).

Martin, M., et al., "P347 Benefit of denosumab therapy in patients with bone metastases from breast cancer: A number-needed-to-treat (NNT) analysis," Breast 20(1):P347, Wiley, United States (2011), 1 page.

Furukawa, H., et al., "Analysis of the Risk and Work Efficiency in Admixture Processes of Injectable Drugs using the Ampule Method and the Pre-filled Syringe Method," Japanese Journal of Pharmaceutical Health Care and Sciences, 29(3): 270-278 (2003).

Ezra, A., et al., "Administration routes and delivery systems of bisphosphonates for the treatment of bone resorption," Adv Drug Deliv Rev., 42(3): 175-195 (2000).

Anonymous, "Highlights of Prescribing Information—Zometa (zoledronic acid)", XP055980793, pp. 1-23 (2014).

Anonymous, "Product information Bonefos (sodium clodronate)", XP055980801, pp. 1-12 (2012).

Office Action, Non-Final Rejection, mailed Nov. 5, 2021, in U.S. Appl. No. 16/766,043, Gomis, R., et al., filed May 21, 2020, 17 pages.

Office Action, Final Rejection, mailed Apr. 15, 2022, in U.S. Appl. No. 16/766,043, Gomis, R., et al., filed May 21, 2020, 6 pages.

Office Action, Non-Final Rejection, mailed Aug. 12, 2022, in U.S. Appl. No. 16/766,043, Gomis, R., et al., filed May 21, 2020, 5 pages.

Co-pending Application, U.S. Appl. No. 18/169,537, inventors Gregory. W.M., et al., filed Feb. 15, 2023 (Not yet Published).

Co-pending Application, U.S. Appl. No. 18/154,295, inventors Gomis. R., et al., filed Jan. 13, 2023 (Not yet Published).

Co-pending Application, U.S. Appl. No. 18/883,685, inventors Gomis, R. et al., filed Sep. 12, 2024 (Not yet Published).

Figure 1

| MAF-FISH assay validation parameters | MAF-IHC assay validation parameters |
|---|---|
| Different probes analyzed | Dako Autostainer Link vs. Ventana Benchmark Ultra |
| Lot-to-lot variation | |
| Intra-assay-repeatability (same run, same person evaluates) | |
| Intra-assay-repeatability (separate run, same person evaluates) | |
| Stability of the biomarker / storage | |
| Intermediate precision (2 separate technicians performing assay) | Intermediate precision (staining was performed on two different devices) |
| Probe concentration, hybridization temperature | Antibody concentration |

AZURE: STUDY DESIGN
Accrual September 2003 – February 2013

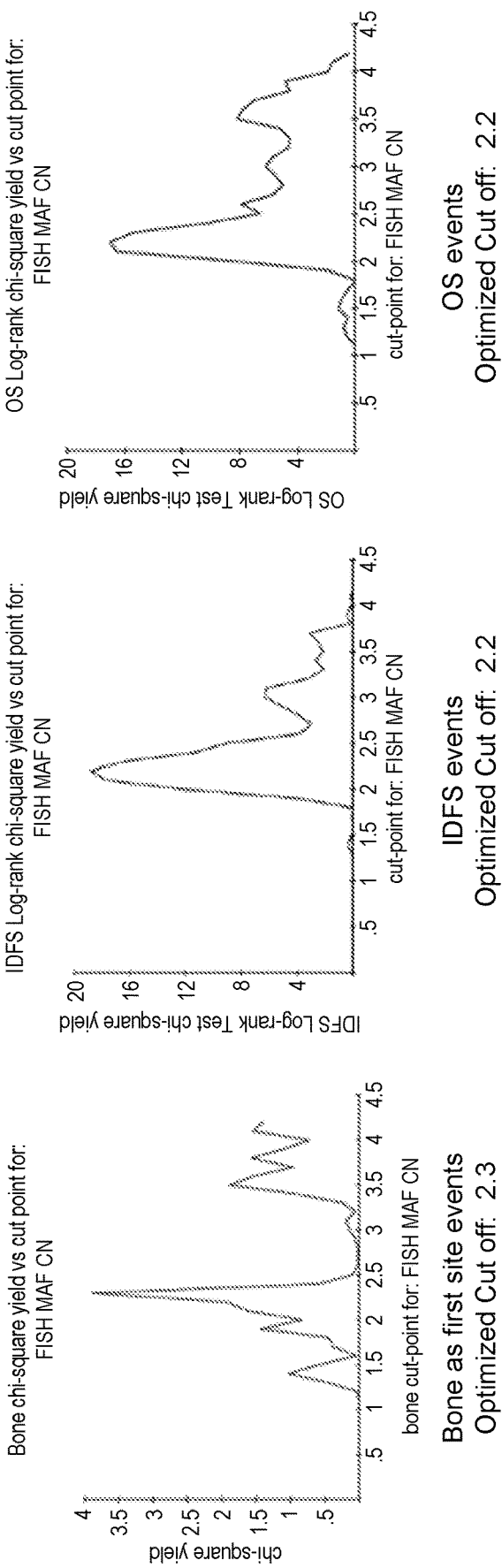

Impact of Zoledronic Ac. treatment on DFS according con MAF FISH

Figure 28
Impact of Zoledronic Ac. treatment on DFS according MAF FISH on post menopausal patients
Control Arm
Post menopausal
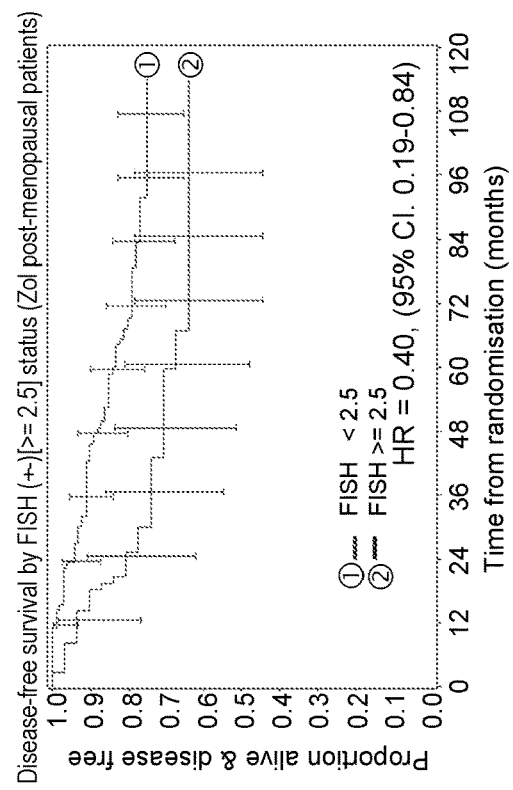
Zoledronic Treatment Arm
Post menopausal
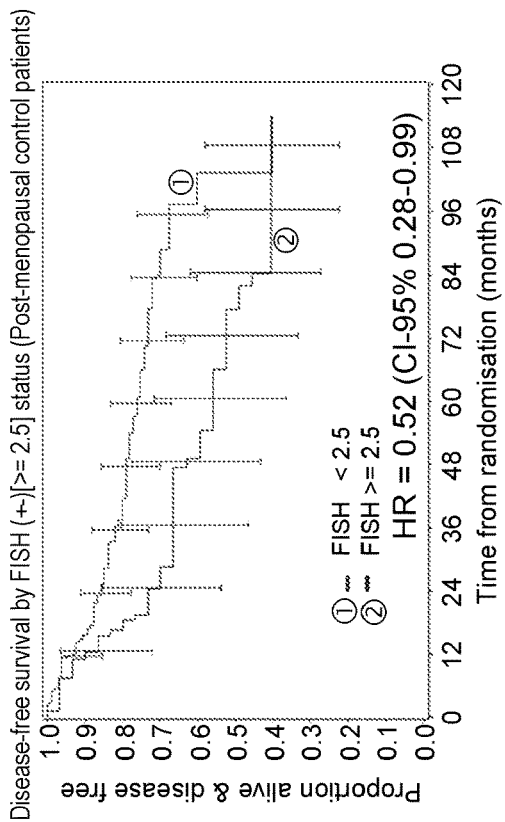

Impact of Zoledronic Ac. treatment on DFS of Non-Menopausal woman according to MAF FISH

- ZOL treatment produces worst DFS outcome in MAF positive Non-Post menopausal patients.

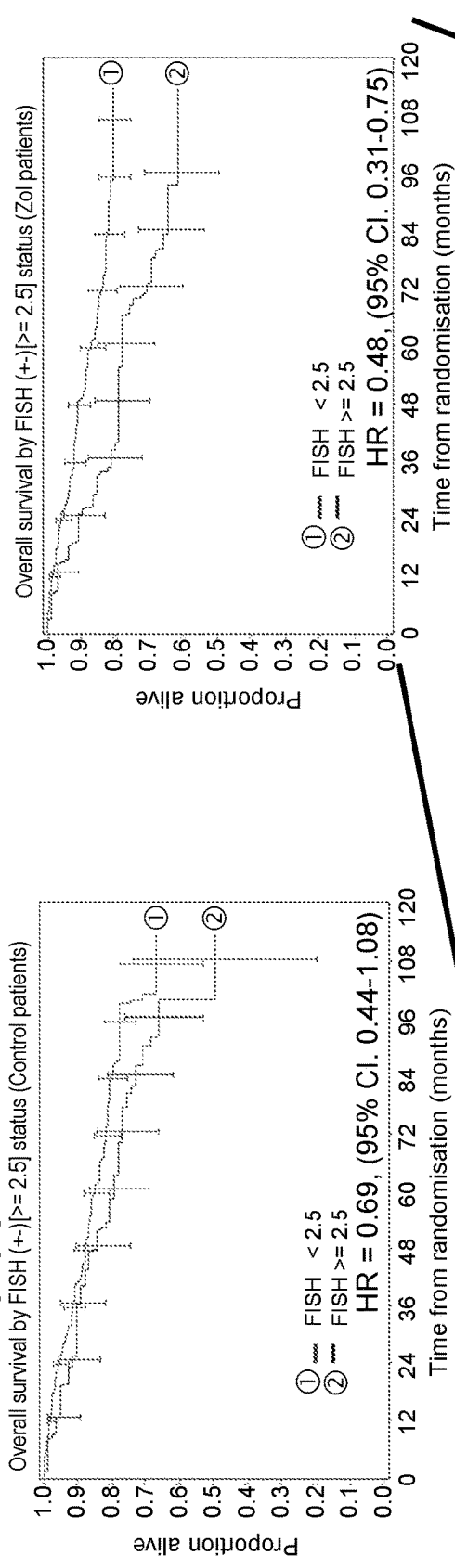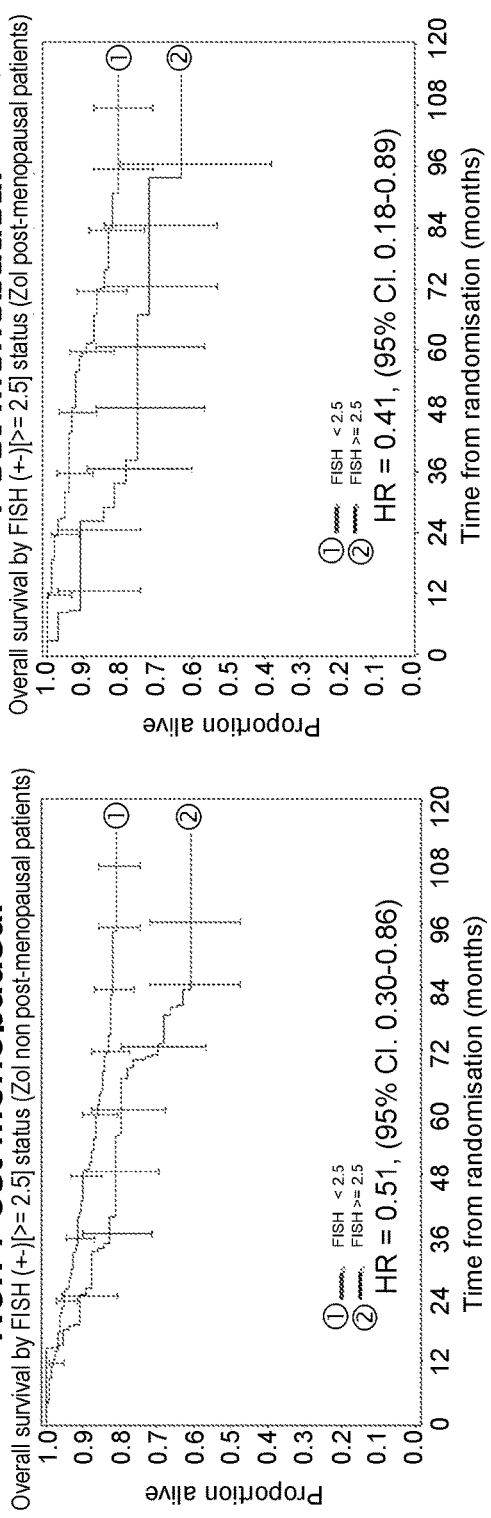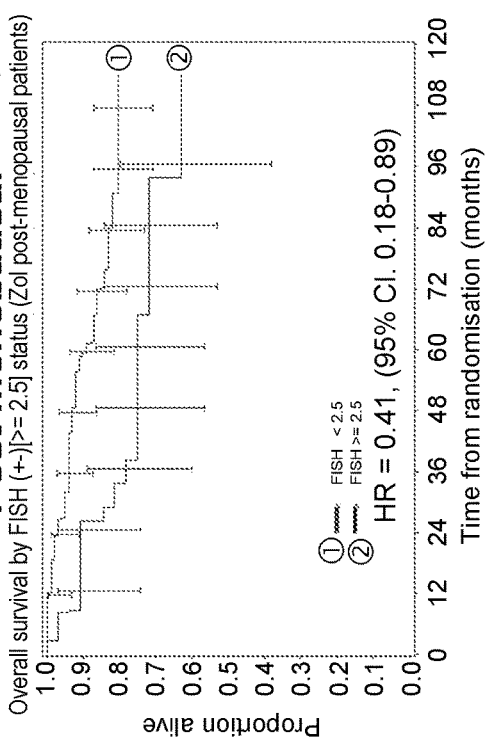
Figure 30
Impact of Zoledronic Ac. treatment on OS according to MAF FISH Figure 31
Impact of Zoledronic Ac. treatment on OS according to MAF FISH in post menopausal patients
Control Arm
Post menopausal
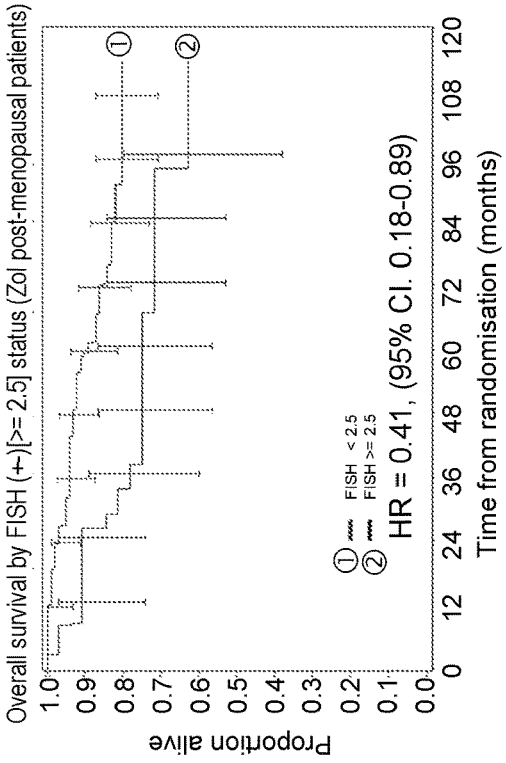
Zoledronic Treatment Arm
Post menopausal
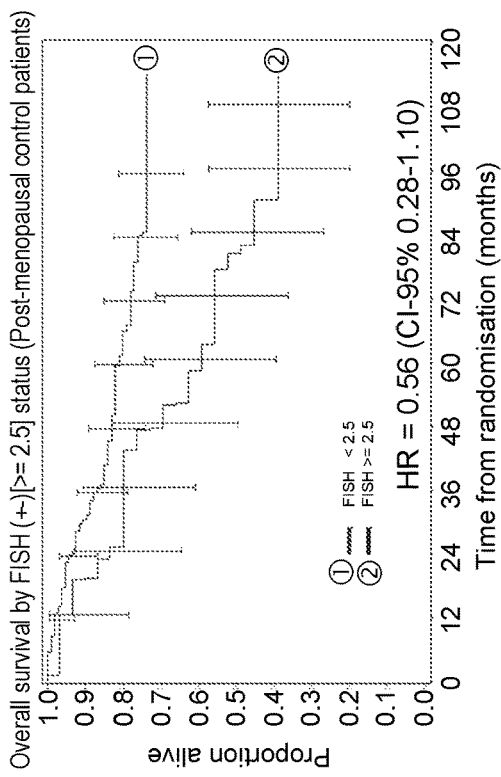

THERAPEUTIC TREATMENT OF BREAST CANCER BASED ON c-MAF STATUS

CROSS-REFERENCE TO RELATED APPLICATIONS

This application is a continuation of U.S. application Ser. No. 16/766,043, which is a 35 U.S.C. § 371 National Phase Application of International Application No. PCT/IB2018/059189, filed Nov. 21, 2018, which claims priority to U.S. Provisional Application No. 62/589,630, filed Nov. 22, 2017, each of which is incorporated herein by reference in its entirety.

REFERENCE TO SEQUENCE LISTING

The content of the electronically submitted sequence listing (Name: 3190_0170002_Seqlisting_ST26.xml; Size: 59,246 bytes; Date of Creation: Apr. 7, 2023) filed with the application is incorporated herein by reference in its entirety.

BACKGROUND OF THE INVENTION

Field of the Invention

The present invention relates to the design of a customized therapy for a subject with breast cancer, wherein the customized therapy is selected based on the c-MAF expression level, copy number, amplification, gain, or translocation. In some embodiments, the customized therapy comprises an agent for avoiding, treating or preventing bone remodeling. In some embodiments, the agent for avoiding, treating or preventing bone remodeling is zoledronic acid, denosumab or clodronate.

Background Art

Breast cancer is the second most common type of cancer worldwide (10.4%; after lung cancer) and the fifth most common cause of death by cancer (after lung cancer, stomach cancer, liver cancer, and colon cancer). Among women, breast cancer is the most common cause of death by cancer. In 2005, breast cancer caused 502,000 deaths worldwide (7% of the deaths by cancer; almost 1% of all deaths). The number of cases worldwide has increased significantly from the 1970s, a phenomenon which is partly due to the modern lifestyle in the western world.

The fact that most of the patients with solid tumor cancer die after metastasis means that it is crucial to understand the molecular and cellular mechanisms allowing a tumor to metastasize. Recent publications have demonstrated how the metastasis is caused by means of complex yet little known mechanisms and also how the different metastatic cell types have a tropism towards specific organs. These tissue specific metastatic cells have a series of acquired functions allowing them to colonize specific organs.

All cells have receptors on their surface, in their cytoplasm and in the cell nucleus. Certain chemical messengers such as hormones bind to said receptors and this causes changes in the cell. There art the breast cancer cells: estrogen receptor (ER), progesterone receptor (PR) and HER2/neue three significant receptors which may affect. For the purpose of naming the cells having any of these receptors, a positive sign is placed thereto when the receptor is present and a negative sign if it is absent: ER positive (ER+), ER negative (ER−), PR positive (PR+), PR negative (PR−), HER2 positive (HER2+) and HER2 negative (HER2−). The receptor state has become a critical assessment for all breast cancers since it determines the suitability of using specific treatments, for example, tamoxifen or trastuzumab.

Unsupervised gene expression array profiling has provided biological evidence for the heterogeneity of breast cancer through the identification of intrinsic subtypes such as luminal A, luminal B, HER2+/ER− and the basal-like subtype.

Triple-negative cancers are defined as tumors that do not express the genes for estrogen receptor (ER), progesterone receptor (PR) nor HER2. This subgroup accounts for 15% of all types of breast cancer and for a higher percentage of breast cancer arising in African and African-American women who are premenopausal. Triple negative breast cancers have a relapse pattern that is very different from Estrogen Receptor positive breast cancers: the risk of relapse is much higher for the first 3-5 years but drops sharply and substantially below that of Estrogen Receptor positive breast cancers after that.

The basal-like subtype is characterized by low expression of both the ER and HER2 clusters of genes, so is typically ER-negative, PR-negative, and HER2-negative on clinical testing; for this reason, it is often referred to as "triple-negative" breast cancer (Breast Cancer Research 2007, 9(Suppl 1):S13). Basal-like cancers express genes usually found in "basal"/myoepithelial cells of the normal breast including high molecular weight cytokeratins (5/6, 14 and 17), P-cadherin, caveolins 1 and 2, nestin, αB crystalline and epidermal growth factor receptor (Reis-Fiho J. et al., http://www.uscap.org/site-/98th/pdf/companion03h03.pdf).

Given that there is no internationally accepted definition for basal-like breast cancers, it is not surprising that there has been a great deal of confusion as to whether triple negative and basal-like breast cancers are synonymous. Although several groups have used these terms interchangeably, it should be noted that not all basal-like cancers lack ER, PR and HER2 and not all triple negative cancers display a basal-like phenotype. The vast majority of triple negative cancers are of basal-like phenotype. Likewise, the vast majority of tumors expressing 'basal' markers are triple negative. It should be noted, however, that there is a significant number of triple negative cancers that do not express basal markers and a small, but still significant, subgroup of basal-like cancers that express either hormone receptors or HER2. Bertucci et al. (Int J Cancer. 2008 Jul. 1; 123(1): 236-40) have addressed this issue directly and confirmed that not all triple negative tumors when analyzed by gene expression profiling were classified as basal-like cancers (i.e., only 71% were of basal-like phenotype) and not all basal-like breast carcinomas classified by expression arrays displayed a triple negative phenotype (i.e., 77%).

The keystone for treating breast cancer is surgery when the tumor is localized with possible adjuvant hormone therapy (with tamoxifen or an aromatase inhibitor), chemotherapy, and/or radiotherapy. Currently, the suggestions for treatment after the surgery (adjuvant therapy) follow a pattern. This pattern is subject to change because every two years a world conference takes place in St. Gallen, Switzerland to discuss the actual results of the worldwide multi-center studies. Likewise, said pattern is also reviewed according to the consensus criterion of the National Institute of Health (NIH). Based on in these criteria, more than 85-90% of the patients not having metastasis in lymph nodes would be candidates to receive adjuvant systemic therapy.

Currently, PCR assays such as Oncotype DX or microarray assays such as MammaPrint can predict the risk of breast cancer relapse based on the expression of specific genes. In February 2007, the MammaPrint assay became the first breast cancer indicator in achieving official authorization from the Food and Drug Administration.

Patent Application No. EP1961825-A1 describes a method for predicting the occurrence of breast cancer metastasis to bone, lung, liver or brain, which comprises determining in a tumor tissue sample the expression level of one or more markers with respect to their corresponding expression level in a control sample, among which include c-MAF. However, this document requires determining several genes simultaneously to enable determining the survival of breast cancer patients and the correlation between the capacities of the gene signature for predicting the survivability free from bone metastasis was not statistically significant.

U.S. Patent Publication No. 2011/0150979 relates to a method for predicting a prognosis of a basal like breast cancer comprising detecting the level of FOXC1.

U.S. Patent Publication No. 2010/0210738 relates to a method for prognosing cancer in a subject with triple negative breast cancer comprising detecting in a sample the expression levels of a series of genes which are randomly up-regulated or down-regulated.

Patent publication U.S. Publ. No. 2011/0130296 relates to the identification of marker genes useful in the diagnosis and prognosis of triple negative breast cancer.

There is a need for the identification of subsets of patients with breast cancer that will benefit from specific treatments, and, conversely, subsets of patients with breast cancer that will not benefit, or will potentially be harmed, by specific treatments.

SUMMARY OF THE INVENTION

In one embodiment, the present invention relates to a method for the treatment of a subject having breast cancer, comprising administering from about 1 mg to about 10 mg of zoledronic acid to the subject, wherein the subject has been identified as having a not increased c-MAF expression level, copy number, amplification, or gain in a tumor sample with respect to a control sample.

In another embodiment, the present invention relates to a method for the treatment of a subject having breast cancer, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is administered from about 1 mg to about 10 mg of zoledronic acid.

In another embodiment, the present invention relates to a method for the treatment of a subject having breast cancer, comprising quantifying the c-MAF expression level, copy number, amplification, or gain in a sample of said subject, wherein if the c-MAF expression level, copy number, amplification, or gain is not increased then said subject is administered from about 1 mg to about 10 mg of zoledronic acid. In another embodiment, the subject is administered about 4 mg of zoledronic acid.

In another embodiment, the present invention relates to a method for the identification of a subject having breast cancer who will benefit from treatment with zoledronic acid, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is administered from about 1 mg to about 10 mg of zoledronic acid. In another embodiment, the subject is administered about 4 mg of zoledronic acid.

In another embodiment, the present invention relates to a method for the identification of a subject having breast cancer who will benefit from treatment with zoledronic acid, comprising quantifying the c-MAF expression level, copy number, amplification, or gain in a sample of said subject, wherein if the c-MAF expression level, copy number, amplification, or gain is not increased, then said subject is administered about 1 mg to about 10 mg of zoledronic acid. In another embodiment, the subject is administered about 4 mg of zoledronic acid.

In another embodiment, the present invention relates to an in vitro method for designing a customized therapy for a subject having breast cancer which comprises: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is susceptible to receive about 1 mg to about 10 mg of zoledronic acid. In another embodiment, the subject is administered about 4 mg of zoledronic acid.

In another embodiment, the present invention relates to a method for the treatment of a subject having breast cancer, comprising administering clodronate at a dose of from about 1000 mg to about 2000 mg about once a day, wherein the subject has been identified as having a not increased c-MAF expression level, copy number, amplification, or gain in a tumor sample with respect to a control sample.

In another embodiment, the present invention relates to a method for the treatment of a subject having breast cancer, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is administered clodronate at a dose of from about 1000 mg to about 2000 mg about once a day.

In another embodiment, the present invention relates to a method for the treatment of a subject having breast cancer, comprising quantifying the c-MAF expression level, copy number, amplification, or gain in a sample of said subject, wherein if the c-MAF expression level, copy number, amplification, or gain is not increased then said subject is administered clodronate at a dose of from about 1000 mg to about 2000 mg about once a day.

In another embodiment, the present invention relates to a method for the identification of a subject having breast cancer who will benefit from treatment with clodronate, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is administered clodronate at a dose of from about 1000 mg to about 2000 mg about once a day.

In another embodiment, the present invention relates to a method for the identification of a subject having breast cancer who will benefit from treatment with clodronate, comprising quantifying the c-MAF expression level, copy number, amplification, or gain in a sample of said subject, wherein if the c-MAF expression level, copy number, amplification, or gain is not increased, then said subject is administered clodronate at a dose of from about 1000 to about 2000 mg about once a day.

In another embodiment, the present invention relates to an in vitro method for designing a customized therapy for a subject having breast cancer, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is susceptible to receive clodronate at a dose of from about 1000 mg to about 2000 mg about once a day.

In another embodiment, the present invention relates to a method for the treatment of a subject having breast cancer comprising administering denosumab at a dose of about 10 mg to about 300 mg, wherein the subject has been identified as having a not increased c-MAF expression level, copy number, amplification, or gain in a tumor sample with respect to a control sample.

In another embodiment, the present invention relates to a method for the treatment of a subject having breast cancer, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is administered denosumab at a dose of from about 10 mg to about 300 mg.

In another embodiment, the present invention relates to a method for the treatment of a subject having breast cancer, comprising quantifying the c-MAF expression level, copy number, amplification, or gain in a sample of said subject, wherein if the c-MAF expression level, copy number, amplification, or gain is not increased then said subject is administered denosumab at a dose of from about 10 mg to about 300 mg.

In another embodiment, the present invention relates to a method for the identification of a subject having breast cancer who will benefit from treatment with denosumab, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is administered denosumab at a dose of from about 10 mg to about 300 mg.

In another embodiment, the present invention relates to a method for the identification of a subject having breast cancer who will benefit from treatment with denosumab, comprising quantifying the c-MAF expression level, copy number, amplification, or gain in a sample of said subject, wherein if the c-MAF expression level, copy number, amplification, or gain is not increased, then said subject is administered denosumab at a dose of from about 10 mg to about 300 mg.

In another embodiment, the present invention relates to an in vitro method for designing a customized therapy for a subject having breast cancer, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is susceptible to receive denosumab at a dose of from about 10 mg to about 300 mg.

BRIEF DESCRIPTION OF THE DRAWINGS

FIG. 1. Overview of the assay parameters.

FIG. 5. MAF cut-off optimized FISH data. A sharp spike on the cutpoint graph indicates that the MAF FISH value truly is a threshold event. Additionally, the predefined cut-off is close to the optimized cut-off.

FIG. 28. Predictive value of MAF FISH for the effect of zoledronic acid treatment on the disease free survival (DFS) outcome on post menopausal patients.

FIG. 30. Predictive value of MAF FISH for the effect of zoledronic acid treatment on the OS outcome.

FIG. 31. Predictive value of MAF FISH for the effect of zoledronic acid treatment on the OS outcome in post menopausal patients.

FIG. 36A shows patients with MAF-positive tumors. FIG. 36B shows patients with MAF-negative tumors. Cumulative incidence unadjusted for differences in the prognostic factors between groups is shown. Events for this endpoint were death and local or contralateral invasive disease. First events in bone were a competing risk. HR=hazard ratio.

DETAILED DESCRIPTION OF THE INVENTION

Definitions of General Terms and Expressions

Figure 2:
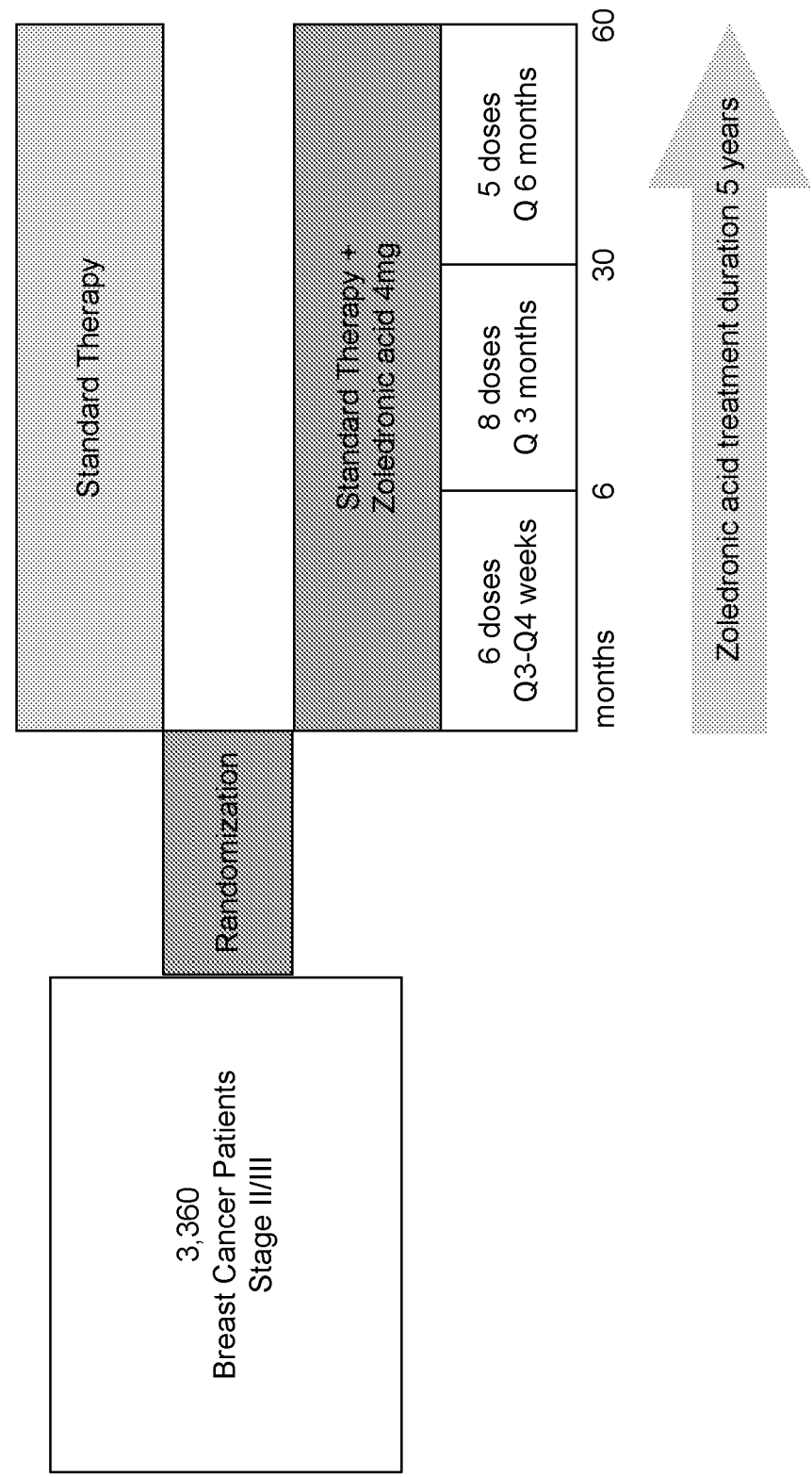
FIG. 2. AZURE study design.

"And/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The c-MAF gene (v-maf musculoaponeurotic fibrosarcoma oncogene homologue (avian) also known as MAF or MGC71685) is a transcription factor containing a leucine zipper which acts like a homodimer or a heterodimer. Depending on the DNA binding site, the encoded protein can be a transcriptional activator or repressor. The DNA sequence encoding c-MAF is described in the NCBI database under accession number NG_016440 (SEQ ID NO: 1)(coding)). The genomic sequence of c-MAF is set forth in SEQ ID NO:13. The methods of the present invention may utilize either the coding sequence or the genomic DNA sequence. Two messenger RNA are transcribed from said DNA sequence, each of the which will give rise to one of the two c-MAF protein isoforms, the a isoform and the R isoform. The complementary DNA sequences for each of said isoforms are described, respectively, in the NCBI database under accession numbers NM_005360.4 (SEQ ID NO: 2) and NM_001031804.2 (SEQ ID NO: 3). Use of the c-MAF gene to predict the prognosis of ER+ breast cancer can be found in U.S. application Ser. No. 13/878,114, which is incorporated herein by reference in its entirety. Use of the c-MAF gene to predict the prognosis of triple-negative and ER+ breast cancer is described in U.S. application Ser. No. 14/391,085, which is incorporated herein by reference in its entirety. Use of the c-MAF gene to predict the prognosis of thyroid cancer is described in U.S. Prov. Appl. No. 61/801,769, which is incorporated herein by reference in its entirety. Use of the c-MAF gene to predict the prognosis of renal cell carcinoma is described in U.S. Prov. application Ser. No. 14/776,390, which is incorporated herein by reference in its entirety. The use of a gene of interest, including c-MAF and the c-MAF gene locus, and probes to the gene locus, to determine the prognosis of an individual having breast cancer is described in U.S. application Ser. No. 14/776,412, which is incorporated herein by reference in its entirety. Use of the c-MAF gene to predict the prognosis of lung cancer is found in U.S. application Ser. No. 14/405,724, which is incorporated herein by reference in its entirety. Use of the c-MAF gene to predict the prognosis of prostate cancer is found in U.S. application Ser. Nos. 14/050,262 and 14/435,128, which are incorporated herein by reference in their entirety. Use of the c-MAF gene to predict the prognosis of HER2+ cancer is found in U.S. application Ser. No. 15/027,946, which is incorporated herein by reference in its entirety. Use of downstream genes of c-MAF to predict the prognosis of cancer is found in U.S. application Ser. Nos. 15/014,916 and 14/776,453, which are incorporated herein by reference in its entirety.

As used herein, the term "basal-like" "basal-like subtype," "breast cancer of the basal-like subtype" and the like, as used herein, refers to a particular subtype of breast cancer characterized by the two negative receptors ER and HER2 and at least one positive receptor of the group consisting of CK5/6, CK14, CK17 and EGFR. Thus, all sentences in the present application which cite and refer to triple negative breast cancer (ER, HER-2, PgR) can also be cited and refer also to basal-like breast cancer wherein ER and HER2 are negative and wherein at least one of CK5/6, CK14, CK17 and EGFR is positive. Alternatively, "basal-like" also refers to breast cancer characterized by a gene expression profile based on the up-regulation and/or down-regulation of the following ten genes: (1) Forkhead box CI (FOXC 1); (2) Melanoma inhibitory activity (MIA); (3) NDC80 homolog, kinetochore complex component (KNTC2); (4) Centrosomal protein 55 kDa (CEP55); (5) Anillin, actin binding protein (ANLN); (6) Maternal embryonic leucine zipper kinase (MELK); (7) G protein-coupled receptor 160 (GPR160); (8) Transmembrane protein 45B (TMEM45B); (9) Estrogen receptor 1 (ESR1); (10) Forkhead box A1 (FOXA1). Because the gene expression profile used to classify breast cancer tumors as basal-like subtype does not include the estrogen receptor, the progesterone receptor or Her2, both triple negative and non-triple negative breast cancers may be classified as basal-like subtype.

As used herein, "Triple-negative breast cancer" refers to a breast cancer which is characterized by a lack of detectable expression of both ER and PR (preferably when the measures of expression of ER and PR are carried out by the method disclosed by M. Elizabeth H et al., Journal of Clinical Oncology, 28(16): 2784-2795, 2010) and the tumor cells are not amplified for epidermal growth factor receptor type 2 (HER2 or ErbB2), a receptor normally located on the cell surface. Tumor cells are considered negative for expression of ER and PR if less than 5 percent of the tumor cell nuclei are stained for ER and PR expression using standard immunohistochemical techniques. As used herein, tumor cells are considered negative for HER2 overexpression if they yield a test result score of 0 or 1+, or 2+ when tested with a HercepTest™ Kit (Code K5204, Dako North America, Inc., Carpinteria, CA), a semi-quantitative immunohistochemical assay using a polyclonal anti-HER2 primary antibody or if they are HER2 FISH negative.

As used herein, "ER+ breast cancer" is understood as breast cancer the tumor cells of which express the estrogen receptor (ER). This makes said tumors sensitive to estrogen, meaning that the estrogen makes the cancerous breast tumor grow. In contrast, "ER− breast cancer" is understood as breast cancer the tumor cells of which do not express the estrogen receptor (ER). Among the ER+ breast cancer are included luminal A and B subtypes.

As used herein, "HER2+" refers to a breast cancer which is characterized by tumor cells with detectable expression of epidermal growth factor receptor type 2 (HER2 or ErbB2) and/or amplification for the HER2 gene, a receptor normally located on the cell surface. As used herein, tumor cells are considered negative for HER2 overexpression if they yield a test result score of 0 or 1+, or 2+ when tested with a HercepTest™ Kit (Code K5204, Dako North America, Inc., Carpinteria, CA), a semi-quantitative immunohistochemical assay using a polyclonal anti-HER2 primary antibody or if they are HER2 FISH negative.

Breast cancer is classified into stages according to the TNM system. (See American Joint Committee on Cancer. AJCC Cancer Staging Manual. 6th ed. New York, NY: Springer, 2002, which is incorporated herein by reference in its entirety.) The prognosis is closely related to the results of the stage classification, and the stage classification is also used to assign patients to treatments both in clinical trials and in the medical practice. The information for classifying into stages is as follows:

TX: The primary tumor cannot be assessed. T0: there is no evidence of tumor. Tis: in situ carcinoma, no invasion. T1: The tumor is 2 cm or less. T2: The tumor is more than 2 cm but less than 5 cm. T3: The tumor is more than 5 cm. T4: Tumor of any size growing in the wall of the breast or skin, or inflammatory breast cancer.

NX: The nearby lymph nodes cannot be assessed. N0: The cancer has not spread to the regional lymph nodes. N1: The cancer has spread to 1 to 3 axillary lymph nodes or to one internal mammary lymph node. N2: The cancer has spread to 4 to 9 axillary lymph nodes or to multiple internal mammary lymph nodes. N3: One of the followings applies: The cancer has spread to 10 or more axillary lymph nodes, or the cancer has spread to the infraclavicular lymph nodes, or the cancer has spread to the supraclavicular lymph nodes or the cancer affects the axillary lymph nodes and has spread to the internal mammary lymph nodes, or the cancer affects 4 or more axillary lymph nodes and minimum amounts of cancer are in the internal mammary nodes or in sentinel lymph node biopsy.

MX: The presence of distant spread (metastasis) cannot be assessed. M0: There is no distant spread. M1: spreading to distant organs which do not include the supraclavicular lymph node has been produced.

According to the American Cancer Society, there are 5 stages of breast cancer, and each of these is subdivided into several additional stages (https://www.cancer.org/cancer/breast-cancer/understanding-a-breast-cancer-diagnosis/stages-of-breast-cancer.html, last visited Aug. 25, 2017).

Stage 0 breast cancer (Tis, N0, M0) is also known as ductal carcinoma in situ (where the cancer cells are still within a duct) or lobular carcinoma in situ (LCIS). In Stage 0 breast cancer, the cancer has not spread to either the lymph nodes or distant sites.

Stage IA breast cancer (T1, N0, M0) is cancer where the tumor is 2 cm or less and where the tumor has not spread to the lymph nodes or distant sites.

Stage IB breast cancer (T0 or T1, N1mi, M0) is cancer where the tumor is 2 cm or less and there are 1 to 3 micrometastases in the underarm lymph nodes (where the cancer in the lymph nodes is 0.2-2 mm), but the cancer has not spread the distant sites.

Stage IIA breast cancer (T0 or T1, N1 (but not N1mi), M0) is breast cancer where the tumor is 2 cm or less across and either (1) the cancer has spread to 1-3 underarm lymph nodes and is greater than 2 mm; (2) tiny amounts of cancer are in internal mammary lymph nodes; or (3) the cancer has spread to 1-3 underarm lymph nodes and to internal mammary lymph nodes. Stage IIA breast cancer (T2, N0, M0) can also be breast cancer where the tumor is larger than 2 cm but less than 5 cm and has not spread to any lymph nodes or distant sites.

Stage IIB breast cancer (T2, N1, M0) is breast cancer where the tumor is larger than 2 cm but less than 5 cm and has spread to 1 to 3 underarm lymph nodes and/or tiny amounts of cancer are in the internal mammary lymph nodes, but the cancer has not spread to distant sites. Stage IIB breast cancer (T3, N0, M0) is also breast cancer where the tumor is larger than 5 cm, but has not grown into the chest wall or skin and hasn't spread to any lymph nodes or distant sites.

Stage IIIA breast cancer (T0 to T2, N2, M0) is breast cancer where the tumor is not more than 5 cm across and has spread to 4 to 9 underarm lymph nodes and has enlarged the mammary lymph nodes but hasn't spread to distant sites. Stage IIIA breast cancer (T3, N1 or N2, M0) is also breast cancer where the tumor is larger than 5 cm across but has not grown into the chest wall or skin and has spread to 1 to 9 underarm nodes or to the internal mammary nodes but not to distant sites.

Stage IIIB breast cancer (T4, N0 to N2, M0) is breast cancer in which the tumor has grown into the chest wall or skin, and one of the following situations applies: (1) the cancer has not spread to the lymph nodes; (2) the cancer has spread to 1 to 3 underarm lymph nodes and/or there are tiny amounts of cancer in the internal mammary lymph nodes in a sentinel lymph node biopsy; or (3) the cancer has spread to 4 to 9 underarm lymph nodes or the cancer has enlarged the internal mammary lymph nodes. In Stage IIIB cancer, the cancer has not spread to distant sites. Inflammatory breast cancer is at least stage IIIB breast cancer, but if it has spread, it could be Stage IIIC or Stage IV.

In Stage IIIC breast cancer (any T, N3, M0), the tumor can be any size, and one of the following situations applies: (1)

the cancer has spread to 10 or more underarm lymph nodes, (2) the cancer has spread to the lymph nodes under the collar bone; (3) the cancer has spread to the lymph nodes above the collar bone; (4) the cancer involves the underarm lymph nodes and has enlarged the internal mammary lymph nodes; or (5) the cancer has spread to 4 or more underarm lymph nodes, and there are tiny amounts of cancer in the internal mammary lymph nodes in a sentinel lymph node biopsy. In Stage IIIC breast cancer, the cancer has not spread to distant sites.

In Stage IV breast cancer (any T, any N, M1), the cancer can be any size, and the cancer may or may not have spread to nearby lymph nodes. The cancer has spread to distant organs or lymph nodes that are far from the breast.

In the context of the present invention, a "post-menopausal" subject is understood to be a woman who has undergone menopause and has experienced sixty consecutive months without menstruation. See Coleman et al Lancet Oncol 2014; 15: 997-1006. In certain embodiments, a woman may confirm her postmenopausal status through the measuring of follicle stimulating hormone (FSH).

In the context of the present invention, a "non-post menopausal" subject is any subject who has not gone through menopause and experienced sixty consecutive months without menstruation. "Non-post menopausal" subjects include premenopausal, perimenopausal, and unknown menopausal status women.

In the context of the present invention, "metastasis" is understood as the propagation of a cancer from the organ where it started to a different organ. It generally occurs through the blood or lymphatic system. When the cancer cells spread and form a new tumor, the latter is called a secondary or metastatic tumor. The cancer cells forming the secondary tumor are like those of the original tumor. If a breast cancer, for example, spreads (metastasizes) to the bone, the secondary tumor is formed of malignant breast cancer cells. The disease in the bone is metastatic breast cancer and not bone cancer. In a particular embodiment of the method of the invention, the metastasis is breast cancer which has spread (metastasized) to the bone.

In the context of the present invention, "recurrence" refers to the return of breast cancer following a period of time in which no cancer was detected. Breast cancer may reoccur locally in the breast or tissue surrounding the breast. Breast cancer may also reoccur in nearby lymph nodes or lymph nodes not in the surrounding area. When the breast cancer reoccurs by spreading to other tissues or travels through the blood stream to recur in bones or other organs, it is also referred to as metastasis. As used herein, recurrence also encompasses the risk of recurrence.

In the context of the present invention, "relapse" refers to the situation when symptoms have decreased, but the subject is not cancer free, and then cancer returns. Breast cancer may relapse locally in the breast or tissue surrounding the breast. Breast cancer may also relapse in nearby lymph nodes or lymph nodes not in the surrounding area. When the breast cancer relapses by spreading to other tissues or travels through the blood stream to recur in bones or other organs, it is also referred to as metastasis. As used herein, relapse also encompasses the risk of relapse.

As used herein, the term "disease free survival" refers to the length of time after primary treatment for a cancer ends that the patient survives without any signs or symptoms of that cancer. In some embodiments, disease free survival is referred to as DFS, relapse-free survival, or RFS.

As used herein, the term "overall survival" or "OS" refers to the length of time from either the date of diagnosis or the start of treatment for a cancer that patients diagnosed with the disease are still alive.

As used herein, the term "subject" or "patient" refers to all animals classified as mammals and includes but is not limited to domestic and farm animals, primates and humans, for example, human beings, non-human primates, cows, horses, pigs, sheep, goats, dogs, cats, or rodents. Preferably, the subject is a human man or woman of any age or race.

The terms "poor" or "good", as used herein to refer to a clinical outcome, mean that the subject will show a favorable or unfavorable outcome. As will be understood by those skilled in the art, such an assessment of the probability, although preferred to be, may not be correct for 100% of the subjects to be diagnosed. The term, however, requires that a statistically significant portion of subjects can be identified as having a predisposition for a given outcome. Whether a portion is statistically significant can be determined readily by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least about 50%, at least about 60%, at least about 70%, at least about 80%, at least about 90% at least about 95%. The p-values are, preferably, 0.05, 0.01, 0.005, or 0.0001 or less. More preferably, at least about 60 percent, at least about 70 percent, at least about 80 percent or at least about 90 percent of the subjects of a population can be properly identified by the method of the present invention.

In the present invention "tumor sample" is understood as a sample (e.g., tumor tissue, circulating tumor cell, circulating tumor DNA) originating from the primary breast cancer tumor. Said sample can be obtained by conventional methods, for example biopsy, using methods well known by the persons skilled in related medical techniques. The methods for obtaining a biopsy sample include splitting a tumor into large pieces, or microdissection, or other cell separating methods known in the art. The tumor cells can additionally be obtained by means of cytology through aspiration with a small gauge needle. To simplify sample preservation and handling, samples can be fixed in formalin and soaked in paraffin or first frozen and then soaked in a tissue freezing medium such as OCT compound by means of immersion in a highly cryogenic medium which allows rapid freezing.

In the context of the present invention, "functionally equivalent variant of the c-MAF protein" is understood as (i) variants of the c-MAF protein (SEQ ID NO: 4 or SEQ ID NO: 5) in which one or more of the amino acid residues are substituted by a conserved or non-conserved amino acid residue (preferably a conserved amino acid residue), wherein such substituted amino acid residue may or may not be one encoded by the genetic code, or (ii) variants comprising an insertion or a deletion of one or more amino acids and having the same function as the c-MAF protein, e.g., to act as a DNA binding transcription factor. Variants of the c-MAF protein can be identified using methods based on the capacity of c-MAF for promoting in vitro cell proliferation as shown in international patent application WO2005/046731 (hereby incorporated by reference in its entirety), based on the capacity of the so-called inhibitor for blocking the transcription capacity of a reporter gene under the control of cyclin D2 promoter or of a promoter containing the c-MAF responsive region (MARE or c-MAF responsive element) in cells expressing c-MAF as described in WO2008098351 (hereby incorporated by reference in its entirety), or based on the capacity of the so-called inhibitor for blocking reporter gene expression under the control of the IL-4 promoter in response to the stimulation with PMA/ionomycin in cells expressing NFATc2 and c-MAF as described in US2009048117A (hereby incorporated by reference in its entirety).

The variants according to the invention preferably have sequence similarity with the amino acid sequence of any of the c-MAF protein isoforms (SEQ ID NO: 4 or SEQ ID NO: 5) of at about least 50%, at least about 60%, at about least 70%, at least about 80%, at least about 90%, at least about 91%, at least about 92%, at least about 93%, at least about 94%, at least about 95%, at least about 96%, at least about 97%, at about least 98% or at about least 99%. The degree of similarity between the variants and the specific c-MAF protein sequences defined previously is determined using algorithms and computer processes which are widely known by the persons skilled in the art. The similarity between two amino acid sequences is preferably determined using the BLASTP algorithm [BLAST Manual, Altschul, S., et al., NCBI NLM NIH Bethesda, Md. 20894, Altschul, S., et al., J. Mol. Biol. 215: 403-410 (1990)].

As used herein, "agent for avoiding, treating or preventing bone remodeling" refers to any molecule capable of preventing, inhibiting, treating, reducing, or stopping bone degradation either by stimulating the osteoblast proliferation or inhibiting the osteoclast proliferation or fixing the bone structure. Agents for avoiding, treating or preventing bone remodeling include agents for avoiding, treating or preventing bone degradation and include agents for avoiding, treating or preventing bone synthesis.

As used herein "outcome" or "clinical outcome" refers to the resulting course of disease and/or disease progression and can be characterized for example by recurrence, period of time until recurrence, relapse, metastasis, period of time until metastasis, number of metastases, number of sites of metastasis and/or death due to disease. For example a good clinical outcome includes cure, prevention of recurrence, prevention of metastasis and/or survival within a fixed period of time (without recurrence), and a poor clinical outcome includes disease progression, metastasis and/or death within a fixed period of time.

As used herein, "invasive disease free survival" or "IDFS" refers to, in cancer, the length of time after primary treatment for a cancer ends that the patient survives without any signs or symptoms of that cancer invading the same breast parenchyma as the original primary tumor or other tissues. In some embodiments, IDFS includes: ipsilateral invasive breast tumor recurrence, local or regional invasive breast cancer recurrence, metastatic or distant recurrence, death attributable to any cause, including breast cancer, contralateral invasive breast cancer, and second primary invasive cancer (non-breast but excluding basal-cell or squamous skin cancers). See Coleman et al Lancet Oncol 2014; 15: 997-1006.

In the present invention, "diagnosis of metastasis in a subject with breast cancer" is understood as identifying a disease (metastasis) by means of studying its signs, e.g., in the context of the present invention by means of increased c-MAF gene expression levels (e.g., overexpression) in the breast cancer tumor tissue with respect to a control sample.

In the present invention "prognosis of the tendency to develop metastasis in a subject with breast cancer" is understood as knowing based on the signs if the breast cancer that said subject has will metastasize in the future. In the context of the present invention, the sign is c-MAF gene overexpression in tumor tissue.

In the context of the present invention, it is understood that "a subject has a positive diagnosis for metastasis" when the breast cancer suffered by said subject has metastasized to other organs of the body, in a particular embodiment, to the bone. The term is similarly used for recurrence and relapse.

The person skilled in the art will understand that the prediction of the tendency for a primary tumor to metastasize, relapse or reoccur is not intended to be correct for all the subjects to be identified (i.e., for 100% of the subjects). Nevertheless, the term requires enabling the identification of a statistically significant part of the subjects (for example, a cohort in a cohort study). Whether a part is statistically significant can be determined in a simple manner by the person skilled in the art using various well known statistical evaluation tools, for example, the determination of confidence intervals, determination of p values, Student's T test, Mann-Whitney test, etc. Details are provided in Dowdy and Wearden, Statistics for Research, John Wiley and Sons, New York 1983. The preferred confidence intervals are at least about 90%, at least about 95%, at least about 97%, at least 98% or at least 99%. The p values are preferably 0.1, 0.05, 0.01, 0.005 or 0.0001. More preferably, at least about 60%, at least about 70%, at least about 80% or at least about 90% of the subjects of a population can be suitably identified by the method of the present invention.

As used herein, "poor prognosis" indicates that the subject is expected, e.g., predicted, to not survive and/or to have, or is at high risk of having, recurrence, relapse, or distant metastases within a set time period. The term "high" is a relative term and, in the context of this application, refers to the risk of the "high" expression group with respect to a clinical outcome (recurrence, distant metastases, etc.). A "high" risk can be considered as a risk higher than the average risk for a heterogeneous cancer patient population. In the study of Paik et al. (2004), an overall "high" risk of recurrence was considered to be higher than 15 percent. The risk will also vary in function of the time period. The time period can be, for example, five years, ten years, fifteen years or even twenty years of initial diagnosis of cancer or after the prognosis was made.

"Reference value", as used herein, refers to a laboratory value used as a reference for values/data obtained by laboratory examinations of patients or samples collected from patients. The reference value or reference level can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from a population of subjects of the chronological age matched group, or based on a pool of samples including or excluding the sample to be tested.

The term "treatment", as used herein, refers to any type of therapy, which aims at terminating, preventing, ameliorating or reducing the susceptibility to a clinical condition as described herein. In an embodiment, the term treatment relates to prophylactic treatment (e.g., a therapy to reduce the susceptibility to a clinical condition), of a disorder or a condition as defined herein. Thus, "treatment", "treating", and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, or immune deficiency.

As used herein, "sample" or "biological sample" means biological material isolated from a subject. The biological sample may contain any biological material suitable for determining the expression level of the c-MAF gene. The sample can be isolated from any suitable biological tissue or fluid such as, for example, tumor tissue, blood, blood plasma, serum, urine or cerebral spinal fluid (CSF).

As used herein, the term "expression level" of a gene as used herein refers to the measurable quantity of gene product produced by the gene in a sample of the subject, wherein the gene product can be a transcriptional product or a translational product. Accordingly, the expression level can pertain to a nucleic acid gene product such as mRNA or cDNA or a polypeptide gene product. The expression level is derived from a subject's sample and/or a reference sample or samples, and can for example be detected de novo or correspond to a previous determination. The expression level can be determined or measured, for example, using microarray methods, PCR methods (such as qPCR), and/or antibody based methods, as is known to a person of skill in the art.

"Increased expression level" is understood as the expression level when it refers to the levels of the c-MAF gene greater than those in a reference sample or control sample. These increased levels can be caused without excluding other mechanisms by a gene or 16q23 or 16q22-24 chromosomal locus amplification, copy gain or translocation. Particularly, a sample can be considered to have high c-MAF expression level when the expression level in the sample isolated from the patient is at least about 1.1 times, 1.2 times, 1.3 times, 1.4 times, 1.5 times, 2 times, 2.1 times, 2.2 times, 2.3 times, 2.4 times, 2.5 times, 3 times, 4 times, 5 times, 10 times, 20 times, 30 times, 40 times, 50 times, 60 times, 70 times, 80 times, 90 times, 100 times or even more with respect to the reference or control. In embodiments, an "increased expression level" is a "high" expression level. An expression level that is "not increased" or "non increased" is any value that is not included in the definition of "increased" expression level, including a value equal or the reference or control level or a decreased expression level in comparison to a reference or control level.

"Decreased expression level" is understood as the expression level when it refers to the levels of the c-MAF gene less than those in a reference sample or control sample. This decreased level can be caused without excluding other mechanisms by a gene or 16q23 or 16q22-24 chromosomal locus deletion. Particularly, a sample can be considered to have decreased c-MAF expression levels when the expression level in the sample isolated from the patient is at least about 1.1 times, 1.2 times, 1.3 times, 1.4 times, 1.5 times, 2 times, 2.1 times, 2.2 times, 2.3 times, 2.4 times, 2.5 times, 3 times, 4 times, 5 times, 10 times, 20 times, 30 times, 40 times, 50 times, 60 times, 70 times, 80 times, 90 times, 100 times or even less with respect to the reference or control. In embodiments, a "decreased expression level" is a "low" expression level or a "not increased" expression level.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population.

In the present invention, "increased gene copy number" is understood as when the c-MAF gene copy number is more than the copy number that a reference sample or control sample has. These increased gene copy number can be caused without excluding other mechanisms by a gene or 16q23 or 16q22-24 chromosomal locus amplification, copy gain or translocation. In particular, it can be considered that a sample has an increased c-MAF copy number when the copy number is more than 2 copies, for example, 2.1, 2.2, 2.3, 2.4, 2.5, 2.6, 2.7, 2.8, 2.9, 3, 4, 5, 6, 7, 8, 9 or 10 copies, and even more than 10 copies of the c-MAF gene. In embodiments, "increased gene copy number" is determined based on an average of copies per cells counted. In embodiments, it can be considered that a sample has an increased c-MAF copy number when the average copy number per cell counted is more than 2 copies, for example, 2.1, 2.2, 2.3, 2.4, 2.5, 2.6, 2.7, 2.8, 2.9, 3, 4, 5, 6, 7, 8, 9 or 10 copies, and even more than 10 copies of the c-MAF gene.

In the present invention, "decreased gene copy number" is understood as when the c-MAF gene copy number is less than the copy number that a reference sample or control sample has. The decreased gene copy number can be caused without excluding other mechanisms by a gene or 16q23 or 16q22-24 chromosomal locus deletions. In some embodiments, it can be considered that a sample has a decreased c-MAF copy number when the copy number is 2 or less than 2 copies of the c-MAF gene.

In the present invention, a "not increased gene copy number" is understood as when the c-MAF gene copy number or the average c-MAF gene copy number is less than the copy number that a reference sample or positive for the increase sample has. The not increased gene copy number can be caused without excluding other mechanisms by no increase in gene or 16q23 or 16q22-24 chromosomal locus amplification, copy gain or translocation. In particular, it can be considered that a sample has not an increased c-MAF copy number or c-MAF average copy number when the copy number is less than 2.1, 2.2, 2.3, 2.4, 2.5, 2.6, 2.7, 2.8, 2.9 copies of the c-MAF gene.

The term "amplification of a gene" as understood herein refers to a process through which various copies of a gene or of a gene fragment are formed in an individual cell or a cell line. The copies of the gene are not necessarily located in the same chromosome. The duplicated region is often called an "amplicon". Normally, the amount of mRNA produced, e.g., the gene expression level also increases in proportion to the copy number of a particular gene.

The term "gain" refers any chromosomal copy number increase from the norm, e.g., in a diploid organism, 3 copies of a gene in a cell would be a gain. In some embodiments, "gain" includes the term "copy gain", and is used synonymously with "copy number".

"Probe", as used herein, refers to an oligonucleotide sequence that is complementary to a specific nucleic acid sequence of interest. In some embodiments, the probes may be specific to regions of chromosomes that are known to undergo translocations. In some embodiments, the probes have a specific label or tag. In some embodiments, the tag is a fluorophore. In some embodiments, the probe is a DNA in situ hybridization probe whose labeling is based on the stable coordinative binding of platinum to nucleic acids and proteins. In some embodiments, the probe is described in U.S. Pat. Nos. 9,127,302 and 9,134,237, which are incorporated by reference in their entirety, or as described in Swennenhuis et al. "Construction of repeat-free fluorescence in situ hybridization probes" Nucleic Acids Research 40(3): e20 (2012).

"Tag" or "label", as used herein, refers to any physical molecule that is directly or indirectly associated with a probe, allowing the probe or the location of the probed to be visualized, marked, or otherwise captured.

"Translocation", as used herein, refers to the exchange of chromosomal material in unequal or equal amounts between chromosomes. In some cases, the translocation is on the same chromosome. In some cases, the translocation is between different chromosomes. Translocations occur at a high frequency in many types of cancer, including breast cancer and leukemia. Translocations can be either primary reciprocal translocations or the more complex secondary translocations. There are several primary translocations that involve the immunoglobin heavy chain (IgH) locus that are believed to constitute the initiating event in many cancers. (Eychène, A., Rocques, N., and Puoponnot, C., A new MAFia in cancer. 2008. Nature Reviews: Cancer. 8: 683-693.)

"Polyploid" or "polyploidy", as used herein, indicates that the cell contains more than two copies of a gene of interest. In some instances, the gene of interest is MAF. In some embodiments, polyploidy is associated with an accumulation of expression of the gene of interest. In some embodiments, polyploidy is associated with genomic instability. In some embodiments, the genomic instability may lead to chromosome translocations.

"Whole genome sequencing", as used herein, is a process by which the entire genome of an organism is sequenced at a single time. See, e.g., Ng., P. C. and Kirkness, E. F., Whole Genome Sequencing. 2010. Methods in Molecular Biology. 628: 215-226.

"Exome sequencing", as used herein, is a process by which the entire coding region of the DNA of an organism is sequenced. In exome sequencing, the mRNA is sequenced. The untranslated regions of the genome are not included in exome sequencing. See, e.g., Choi, M. et al., Genetic diagnosis by whole exome capture and massively parallel DNA sequencing. 2009. PNAS. 106(45): 19096-19101.

As used herein, "binding member" describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, receptor-ligand and enzyme-substrate. In some embodiments, the binding member is an antibody. In some embodiments, the binding member is an antibody that binds a c-MAF antigen. In certain embodiments, the binding member is any c-MAF antibody disclosed herein.

As used herein, "CDR region" or "CDR" is intended to indicate the hypervariable regions of the heavy and light chains of the immunoglobulin as defined by Kabat et al., (1991) Sequences of Proteins of Immunological Interest, 5th Edition. US Department of Health and Human Services, Public Service, NIH, Washington. An antibody typically contains 3 heavy chain CDRs, termed HCDR1, HCDR2, and HCDR3, and 3 light chain CDRs, termed LCDR1, LCDR2 and LCDR3. The term CDR or CDRs is used here in order to indicate one of these regions or several, or even the whole, of these regions which contain the majority of the amino acid residues responsible for the binding by affinity of the antibody for the antigen or the epitope which it recognizes. Among the six CDR sequences, the third CDR of the heavy chain (HCDR3) has a greatest size variability, e.g., greater diversity, essentially due to the mechanism known in the art as V(D)J rearrangement of the V, D and J gene segments of the germline immunoglobulin heavy chain gene locus. The HCDR3 may be as short as two amino acids or as long as 26 amino acids, or may have any length in between these two extremes. CDR length may also vary according to the length that can be accommodated by the particular underlying framework. Functionally, HCDR3 can play an important role in the determination of the specificity of the antibody (Segal et al., (1974) Proc Natl Acad Sci USA. 71(11): 4298-302; Amit et al., (1986) Science 233(4765): 747-53; Chothia et al., (1987) J. Mol. Biol. 196(4): 901-17; Chothia et al., (1989) Nature 342(6252): 877-83; Caton et al., (1990) J. Immunol. 144(5): 1965-8; Sharon (1990a) PNAS USA. 87(12): 4814-7, Sharon (1990b) J. Immunol. 144: 4863-4869, Kabat et al., (1991) Sequences of Proteins of Immunological Interest, 5th Edition. US Department of Health and Human Services, Public Service, NIH, Washington).

As used herein, "antibody", "antibody molecule", or "antibodies" describes an immunoglobulin whether naturally, or partly, or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids. Antibody fragments that comprise an antibody antigen-binding site include, but are not limited to, molecules such as Fab, Fab', F(ab')2, Fab'-SH, scFv, Fv, dAb and Fd. Various other antibody molecules including one or more antibody antigen-binding sites have been engineered, including for example Fab2, Fab3, diabodies, triabodies, tetrabodies, camelbodies, nanobodies and minibodies. Antibody molecules and methods for their construction and use are described in Hollinger & Hudson (2005) Nature Biot. 23(9): 1126-1136.

As used herein, "antibody molecule" should be construed as covering any binding member or substance having an antibody antigen-binding site with the required specificity and/or binding to antigen. Thus, this term covers functional antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described for example in EP0120694A (Boss et al) and EP0125023A (Cabilly et al), which are incorporated herein in their entirety.

As used herein, "functional fragment or variant" of, for example, a binding member of the present invention means a fragment or variant of a binding member that retains at least some function of a full binding member (e.g., the ability to specifically bind to an antigen, such as Maf).

"Tumor tissue sample" is understood as the tissue sample originating from the breast cancer tumor, including but not limited to circulating tumor cells and circulating tumor DNA. Said sample can be obtained by conventional methods, for example biopsy, using methods well known by the persons skilled in related medical techniques.

"Osteolytic bone metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcemia, spinal cord compression and other syndromes resulting from nerve compression.

Treatment in the "adjuvant" setting refers to treatment administered after a primary treatment, such as surgery or radiotherapy.

Treatment in the "neoadjuvant" setting refers to treatment administered before the primary treatment.

Method for Designing Customized Therapy of the Invention in Patients with Breast Tumors The present invention is directed to identifying subjects suffering from breast cancer who will benefit from treatment with particular agents and/or therapies. In further embodiments, the invention is directed to treating patients who are identified as benefitting from treatment with particular agents and therapies. In some embodiments, the subjects have a not increased or low expression level, copy number, amplification, gain and/or translocation of c-MAF. In particular embodiments, the cancer is triple-negative breast cancer. In other embodiments, the cancer is ER+ breast cancer. In further embodiments, the cancer is ER− breast cancer. In still further embodiments, the cancer is HER2+ breast cancer. In some embodiments, the cancer is a basal-like breast cancer. In one embodiment, the subjects are post-menopausal. In an embodiment, the subjects are non-post menopausal. As described U.S. application Ser. No. 14/391,085, U.S. Prov. Appl. No. 61/801,769, U.S. Prov. application Ser. No. 14/776,390, U.S. application Ser. No. 14/776,412, U.S. application Ser. No. 14/405,724, U.S. application Ser. No. 14/050,262, U.S. application Ser. No. 14/435,128, U.S. application Ser. No. 15/027,946 U.S. application Ser. No. 15/014,916, U.S. application Ser. No. 15/534,893, U.S. application Ser. No. 14/776,453, and Int'l Appl. No. PCT/IB2017/053094, each of which is incorporated herein by reference in its entirety, the levels of c-MAF can be used to diagnosis metastasis, relapse or recurrence, or to predict the tendency of a tumor to undergo metastasis, relapse or recurrence. Therefore, as described in the present invention, given that the c-MAF gene overexpression, amplification, copy number, or gain in breast cancer cells is related to the presence of metastasis, relapse or recurrence, information related to the c-MAF gene expression levels, amplification, copy number, or gain allows for the making of decisions of the most suitable therapy for the subject suffering said cancer. In an embodiment, the invention comprises quantifying only the c-MAF gene expression level, amplification, copy number, or gain as a single marker, e.g., the method does not involve determining the expression level of any additional marker. Thus, in one embodiment the invention relates to a method for the treatment of a subject having breast cancer comprising administering an agent that avoids, treats and/or prevents bone remodeling, wherein the subject has been identified as having a not increased c-MAF expression level, copy number, amplification, or gain in a tumor sample with respect to a control sample. In one embodiment, the invention relates to a method for the treatment of a subject having breast cancer, comprising: (i) quantifying the c-MAF gene expression level, copy number, amplification, or gain in a sample of said subject, and (ii) comparing the expression level, copy number, amplification, or gain obtained in (i) with a reference value, wherein if the expression level, copy number, amplification, or gain is not increased with respect to said reference value, then said subject is administered an agent that avoids, treats and/or prevents bone remodeling. In embodiments, the invention relates to a method for the treatment of a subject having breast cancer, comprising quantifying the c-MAF expression level, copy number, amplification, or gain in a sample of said subject, wherein if the c-MAF expression level, copy number, amplification, or gain is not increased then said subject is administered an agent that avoids, treats and/or prevents bone remodeling. In certain embodiments, the invention relates to method for the identification of a subject having breast cancer who will benefit from treatment with an agent that avoids, treats and/or prevents bone remodeling, comprising (i) quantifying the c-MAF gene expression level, copy number, amplification, or gain in a sample of said subject and (ii) comparing the expression level, copy number, amplification, or gain obtained in (i) with a reference value, wherein if the expression level, copy number, amplification, or gain is not increased with respect to said reference value, then said subject is administered an agent that avoids, treats and/or prevents bone remodeling. In embodiments, the invention relates to a method for the identification of a subject having breast cancer who will benefit from treatment with an agent that avoids, treats and/or prevents bone remodeling comprising quantifying the c-MAF expression level, copy number, amplification, or gain in a sample of said subject, wherein if the c-MAF expression level, copy number, amplification, or gain is not increased, then said subject is administered an agent that avoids, treats and/or prevents bone remodeling. In certain embodiments, the invention is directed to in vitro method for designing a customized therapy for a subject having breast cancer which comprises: (i) quantifying the c-MAF gene expression level, copy number, amplification, or gain in a sample of said subject and ii) comparing the expression level, copy number, amplification, or gain obtained in (i) with a reference value, wherein if the expression level, copy number, amplification, or gain is not increased with respect to said reference value, then said subject is susceptible to receive an agent that avoids, treats and/or prevents bone remodeling. In some embodiments, the treatment or therapy improves overall survival. In other embodiments, the treatment or therapy improves invasive disease free survival. In further embodiments, the treatment or therapy improves disease-free survival. In some embodiments, the subject has cancer-treatment-induced-bone-loss (CTIBL). In certain embodiments, the treatment or therapy treats or improves the CTIBL. In other embodiments, the treatment or therapy avoids or prevents CTIBL.

In some embodiments, the subject has a high c-MAF gene expression level. In other embodiments, the subject has a low c-MAF gene expression level. In certain embodiments, the subject is administered an agent that avoids and/or prevents bone remodeling, including agents that avoid, treat or prevent bone degradation. In embodiments, the subject is additionally administered an agent that treats the cancer. In particular embodiments, the agent that avoids and/or prevents bone remodeling or the c-MAF inhibitory agent is any agent disclosed in U.S. application Ser. No. 14/391,085, U.S. Prov. Appl. No. 61/801,769, U.S. Prov. application Ser. No. 14/776,390, U.S. application Ser. No. 14/776,412, U.S. application Ser. No. 14/405,724, U.S. application Ser. No. 14/050,262, U.S. application Ser. No. 14/435,128, U.S. application Ser. No. 15/027,946 U.S. application Ser. No. 15/014,916, U.S. application Ser. No. 15/534,893, U.S. application Ser. No. 14/776,453, and Int'l Appl. No. PCT/IB2017/053094, which are incorporated herein by reference in their entireties.

In an embodiment, the invention relates to a method for the treatment of bone metastasis in a subject having breast cancer and having decreased c-MAF levels in a tumor sample with respect to a control sample comprising administering an agent capable of preventing or inhibiting bone remodeling and or improving disease free survival or overall survival, wherein the agent capable of avoiding, treating or preventing bone remodeling or improving disease free survival or overall survival is selected from the group consisting of: a bisphosphonate, a RANKL inhibitor, PTH, PTHLH inhibitor (including neutralizing antibodies and peptides), a PRG analog, strontium ranelate, a DKK-1 inhibitor, a dual MET and VEGFR2 inhibitor, an estrogen receptor modulator, an EGFR inhibitor, calcitonin, Radium-223, a CCR5 antagonist, a Src kinase inhibitor, a COX-2 inhibitor, an mTor inhibitor, and a cathepsin K inhibitor. In some embodiments, the subject is non-postmenopausal. In other embodiments, the subject is postmenopausal.

In embodiments, the bisphosphonate treatment is begun at the start of adjuvant therapy. In certain embodiments, the bisphosphonate treatment is continued for about 3-5 years, and is continued only after 5 years if fracture risk is indicated.

In certain embodiments, the subject is administered an agent that avoids, treats and/or prevents bone remodeling, including agents that avoid, treat or prevent bone degradation. In embodiments, the subject is administered an agent that avoids, treats and/or prevents bone degradation. In embodiments, the agent that avoids, treats and/or prevents bone degradation is selected from the group consisting of: denosumab, zoledronic acid, clodronate, alendronate, risedronate, and ibandronate.

Once the c-MAF gene expression level, copy number, amplification or gain in the sample have been measured and compared with the control sample, the expression level, copy number, amplification or gain of said gene indicates whether the subject is susceptible to receive a therapy or agent intended to avoid, treat or prevent bone remodeling.

In some embodiments, a copy number of MAF or average copy number of MAF per cell as measured using FISH$\geq$2.1, 2.2, 2.3, 2.4, 2.5, 2.6, 2.7, 2.8, 2.9 or 3.0 is considered a high value. In embodiments, the MAF FISH value is $\geq$2.2. In certain embodiments, the MAF FISH value is $\geq$2.3. In other embodiments, the MAF FISH value is $\geq$2.4. In further embodiments, the MAF FISH value is $\geq$2.5. In other embodiments, the copy number of c-MAF as measured using FISH is <2.1, 2.2, 2.3, 2.4, 2.5, 2.6, 2.7, 2.8, 2.9 copies of the c-MAF gene is considered a low value. In embodiments, the copy number of c-MAF as measured using c-MAF is <2.1. In particular embodiments, the copy number of c-MAF is $\leq$2.0, 1.9. 1.8. 1.7. 1.6 or 1.5. In one embodiment, the copy number of c-MAF is $\leq$2.0.

In a particular embodiment, the subject has metastasis or a prognosis to undergo metastasis. In some embodiments, the metastasis is a bone metastasis. In a further embodiment, the bone metastasis is osteolytic metastasis.

In some embodiments, the method comprises in a first step quantifying the c-MAF gene expression level, copy number, gain or amplification in a tumor sample in a subject suffering from breast cancer.

In some embodiments, the sample is a primary tumor tissue sample of the subject. In other embodiments, the sample is a metastatic tumor sample of the subject. In a second step, the c-MAF gene expression level, copy number, amplification or gain obtained in the tumor sample of the subject is compared with the expression level, copy number, amplification or gain of said gene in a control sample. The determination of the c-MAF gene expression levels, copy number, amplification or gain must be related to values of a control sample or reference sample. Depending on the type of tumor to be analyzed, the exact nature of the control sample may vary. Thus, in some embodiments, the reference sample is a tumor tissue sample of a subject with breast cancer that has not metastasized, relapsed or reoccurred or that corresponds to the median value of the c-MAF gene expression levels, copy number, amplification or gain measured in a tumor tissue collection in biopsy samples of subjects with breast cancer which has not metastasized, relapsed or reoccurred.

In one embodiment, the methods of the invention comprise in a second step comparing the c-MAF gene expression level, copy number, amplification or gain obtained in the tumor sample (including but not limited to a primary tumor biopsy, circulating tumor cells and circulating tumor DNA) from the subject with the expression level of said gene in a control sample.

The determination of the c-MAF gene expression level, copy number, amplification or gain must be correlated with values of a control sample or reference sample. Depending on the type of tumor to be analyzed, the exact nature of the control sample may vary. Thus, in the event that a diagnosis is to be evaluated, then the reference sample is a tumor tissue sample from a subject with breast cancer that has not metastasized or that corresponds to the median value of the c-MAF gene expression levels measured in a tumor tissue collection in biopsy samples from subjects with breast cancer which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (c-MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least about 2, at least about 10, at least about 20, at least about 25, at least about 50, at least about 75, at least about 100, at least about 250, at least about 500, to more than 1000 subjects, classified according to the foregoing considerations, for example according to various age categories, are taken as the reference group. The sample collection from which the reference level is derived will preferably be formed by subjects suffering from the same type of cancer as the patient object of the study (e.g., breast cancer). Similarly, the reference value within a cohort of patients can be established using a receiving operating curve (ROC) and measuring the area under the curve for all de sensitivity and specificity pairs to determine which pair provides the best values and what the corresponding reference value is. ROC is a standard statistical concept. A description can be found in Stuart G. Baker "The Central Role of Receiver Operating Characteristic (ROC) curves in Evaluating Tests for the Early Detection of Cancer" *Journal of The National Cancer Institute* (2003) Vol 95, No. 7, 511-515.

Once this median or reference value has been established, the level of this marker expressed in tumor tissues from patients with this median value can be compared and thus be assigned, for example, to the "increased" or "not increased" expression level. Due to the variability among subjects (for example, aspects referring to age, race, etc.) it is very difficult (if not virtually impossible) to establish absolute reference values of c-MAF expression. Thus, in particular embodiments the reference values for "increased" or "reduced" or "not increased" expression of the c-MAF expression are determined by calculating the percentiles by conventional means which involves performing assays in one or several samples isolated from subjects whose disease is well documented by any of the methods mentioned above the c-MAF expression levels. The "reduced" or "not increased" levels of c-MAF can then preferably be assigned to samples wherein the c-MAF expression levels are equal to or lower than $50^{th}$ percentile in the normal population including, for example, expression levels equal to or lower than the $60^{th}$ percentile in the normal population, equal to or lower than the $70^{th}$ percentile in the normal population, equal to or lower than the $80^{th}$ percentile in the normal population, equal to or lower than the $90^{th}$ percentile in the normal population, and equal to or lower than the $95^{th}$ percentile in the normal population. The "increased" c-MAF gene expression levels can then preferably be assigned to samples wherein the c-MAF gene expression levels are equal to or greater than the $50^{th}$ percentile in the normal population including, for example, expression levels equal to or greater than the $60^{th}$ percentile in the normal population, equal to or greater than the $70^{th}$ percentile in the normal population, equal to or greater than the $80^{th}$ percentile in the normal population, equal to or greater than the $90^{th}$ percentile in the normal population, and equal to or greater than the $95^{th}$ percentile in the normal population.

In a particular embodiment, the degree of amplification or gain of the c-MAF gene can be determined by means of determining the amplification or gain of a chromosome region containing said gene. Preferably, the chromosome region the amplification or gain of which is indicative of the existence of amplification or gain of the c-MAF gene is the locus 16q22-q24 which includes the c-MAF gene. The locus 16q22-q24 is located in chromosome 16, in the long arm of said chromosome and in a range between band 22 and band 24. This region corresponds in the NCBI database with the contigs NT_010498.15 and NT_010542.15. In another preferred embodiment, the degree of amplification or gain of the c-MAF gene can be determined by means of using a probe specific for said gene.

In some embodiments, the amplification or gain is in region at the 16q23 locus. In some embodiments, the amplification or gain is in any part of the chromosomal region between Chr. 16-79,392,959 bp to 79,663,806 bp (from centromere to telomere). In some embodiments, the amplification or gain is in the genomic region between Chr. 16—79,392,959 bp to 79,663,806 bp, but excluding DNA repeating elements. In some embodiments, amplification or gain is measured using a probe specific for that region.

In an embodiment, the c-MAF gene is amplified with respect to a reference gene copy number when the c-MAF gene copy number is higher than the copy number that a reference sample or control sample has. In one example, the c-MAF gene is said to be "amplified" if the genomic copy number or the average genomic copy number of the c-MAF gene is increased by at least about 2- (e.g., 6 copies), 3- (e.g., 8 copies), 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number or the average genomic copy number of the c-MAF gene per cell is at least about 2.1, 2.2, 2.3, 2.4, 2.5, 2.6, 2.7, 2.8, 2.9, 3, 4, 5, 6, 7, 8, 9, 10, 11, 12, 13, 14, 15, 16, 17, 18, 19, 20, 21, 22, 23, 24, 25, 26, 27, 28, 29, 30, and the like. In one example, the c-MAF gene is not amplified if the genomic copy number or the average genomic copy number of the c-MAF gene per cell is less than about 2 copies per cell.

In some embodiments, when copy number is measured, the control sample refers to a tumor sample of a subject with breast cancer who has not suffered metastasis or that correspond to the median value of the c-MAF gene copy number measured in a tumor tissue collection in biopsy samples of subjects with breast cancer who have not suffered metastasis. Said reference sample is typically obtained by combining equal amounts of samples from a subject population. If the c-MAF gene copy number is increased with respect to the copy number of said gene in the control sample, then subject has a positive diagnosis for metastasis or a greater tendency to develop metastasis. In another embodiment, the reference gene copy number is the gene copy number in a sample of breast cancer from a subject who has not suffered bone metastasis.

In another embodiment, the amplification or gain is determined by means of in situ hybridization or PCR.

In another embodiment and as described in the present invention, given that the chr16q22-24, including the c-MAF gene, is amplified in breast cancer cells is related to the presence of metastasis, relapse or recurrence the chr16q22-24, including the c-MAF gene, amplification or gain allow making decisions in terms of the most suitable therapy for the subject suffering said cancer.

The determination of the amplification of the c-MAF gene needs to be correlated with values of a control sample or reference sample that correspond to the level of amplification of the c-MAF gene measured in a tumor tissue sample of a subject with breast cancer who has not suffered metastasis or that correspond to the median value of the amplification of the c-MAF gene measured in a tumor tissue collection in biopsy samples of subjects with breast cancer who have not suffered metastasis. Said reference sample is typically obtained by combining equal amounts of samples from a subject population.

In general, the typical reference samples will be obtained from subjects who are clinically well documented and in whom the absence of metastasis is well characterized. The sample collection from which the reference level is derived will preferably be made up of subjects suffering the same type of cancer as the patient object of the study. Once this median value has been established, the level of amplification of c-MAF in tumor tissues of patients can be compared with this median value, and thus, if there is amplification, the subject has a positive diagnosis of metastasis or a greater tendency to develop metastasis.

In another aspect, the invention relates to an in vitro method for designing a customized therapy for a patient suffering from breast cancer, which comprises determining if the c-MAF gene is translocated in a sample of said subject.

In some embodiments, the translocated gene is from the region at the 16q23 locus. In some embodiments, the translocated gene is from any part of the chromosomal region between Chr. 16-79,392,959 bp to 79,663,806 bp (from centromere to telomere). In some embodiments, the translocated gene is from the genomic region between Chr. 16—79,392,959 bp to 79,663,806 bp, but excluding DNA repeating elements. In some embodiments, the translocation is measured using a probe specific for that region.

In a particular embodiment, the translocation of the c-MAF gene can be determined by means of determining the translocation of a chromosome region containing said gene. In one embodiment, the translocation is the t(14,16) translocation. In another embodiment, the chromosome region that is translocated is from locus 16q22-q24. The locus 16q22-q24 is located in chromosome 16, in the long arm of said chromosome and in a range between band 22 and band 24. This region corresponds in the NCBI database with the contigs NT_010498.15 and NT_010542.15. In an, the c-MAF gene translocates to chromosome 14 at the locus 14q32, resulting in the translocation t(14,16)(q32,q23). This translocation places the MAF gene next to the strong enhancers in the IgH locus, which, in some cases, leads to overexpression of MAF. (Eychène, A., Rocques, N., and Puoponnot, C., A new MAFia in cancer. 2008. *Nature Reviews: Cancer.* 8: 683-693.)

In an embodiment, the translocation of the c-MAF gene can be determined by means of using a probe specific for said translocation.

One embodiment of the invention comprises a method in which in a first step it is determined if the c-MAF gene is translocated in a sample of a subject. In an embodiment, the sample is a tumor tissue sample.

In some embodiments, the amplification, gain and copy number of the c-MAF gene are determined after translocation of the c-MAF gene is determined. In some embodiments, a probe is used to determine if the cell is polyploid for the c-MAF gene. In some embodiments, a determination of polyploidy is made by determining if there are more than 2 signals from the gene of interest. In some embodiments, polyploidy is determined by measuring the signal from the probe specific for the gene of interest and comparing it with a centromeric probe or other probe.

Method of Predicting Survival, Including IDFS, Using c-MAF

The present invention is directed to predicting the IDFS of a subject suffering from breast cancer. In certain embodiments, the subjects have a high expression level, copy number, amplification, or gain of c-MAF. In other embodiments, the subjects have a low expression level, copy number, amplification, or gain of c-MAF. In some embodiments, the cancer is triple-negative breast cancer. In other embodiments, the cancer is ER+ breast cancer. In further embodiments, the cancer is ER− breast cancer. In certain embodiments, the cancer is basal-like breast cancer. In still further embodiments, the cancer is HER2+ breast cancer. In some embodiments, the subjects are post-menopausal. In other embodiments, the subjects are non-post menopausal.

In some embodiments, the invention is directed to an in vitro method for predicting the IDFS of a patient with breast cancer which comprises i) quantifying the expression level, copy number, amplification, or gain of the c-MAF gene in a sample of said subject and ii) comparing the expression level, copy number, amplification, or gain obtained in step i) with a reference value, wherein increased expression level, copy number, amplification, or gain of said gene with respect to said reference value is indicative of a poor IDFS prognosis.

In an embodiment, the invention is directed to an in vitro method for predicting the IDFS of a patient with breast cancer which comprises determining the c-MAF gene expression level, copy number, amplification, or gain in a sample of said subject relative to a reference wherein an increase of the c-MAF gene expression level, copy number, amplification, or gain with respect to said reference is indicative of a poor IDFS prognosis.

In a further embodiment, the invention is directed to an in vitro method for predicting the IDFS, excluding bone recurrence, of a patient with breast cancer which comprises determining the c-MAF gene expression level, copy number, amplification, or gain in a sample of said subject relative to a reference wherein an increase of the c-MAF gene expression level, copy number, amplification, or gain with respect to said reference is indicative of a poor IDFS prognosis, excluding bone recurrence.

In some embodiments, the copy number of MAF or average copy number of MAF per cell as measured using FISH≥2.1, 2.2, 2.3, 2.4, 2.5, 2.6, 2.7, 2.8, 2.9 or 3.0 is considered a high value. In certain embodiments, the MAF FISH value is ≥2.2. In other embodiments, the MAF FISH value is ≥2.3. In further embodiments, the MAF FISH value is ≥2.4. In still further embodiments, the MAF FISH value is ≥2.5.

In some embodiments, the c-MAF status of the subject predicts the overall survival or the duration of the disease-free survival of the subject. In certain embodiments, the c-MAF status in any of the embodiments herein includes 16923 or 16q22-24 chromosomal locus amplification, copy gain or translocation or lack thereof, or 16q23 or 16q22-24 chromosomal locus deletions. In particular embodiments, a subject with an increase in their c-MAF gene expression level, copy number, amplification, or gain with respect to a reference has a shorter disease free survival than a subject without an increase of the c-MAF gene expression level, copy number, amplification, or gain with respect to a reference. In embodiments, the disease free survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less than the disease free survival of a subject without an increase of the c-MAF gene expression level, copy number, amplification, or gain with respect to a reference. In certain embodiments, a subject with an increase in their c-MAF gene expression level, copy number, amplification, or gain with respect to a reference has a shorter overall survival than a subject without an increase of the c-MAF gene expression level, copy number, amplification, or gain with respect to a reference. In embodiments, the overall survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less than the disease free survival of a subject without an increase of the c-MAF gene expression level, copy number, amplification, or gain with respect to a reference. In embodiments, the subject is post menopausal. In other embodiments, the subject is non-post-menopausal. In some embodiments, the subject is premenopausal.

In embodiments, the disease free survival of a subject without an increase of the c-MAF gene expression level, copy number, amplification, or gain with respect to a reference is longer after treatment with a bone modifying agent and/or an agent that avoids or prevents bone degradation, e.g., zoledronic acid, than the disease free survival of a subject with an increase in their c-MAF gene expression level, copy number, amplification, or gain with respect to a reference. In embodiments, the disease free survival of a subject without an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more after treatment with zoledronic acid than the disease free survival of a subject with an increase of the c-MAF gene expression level, copy number, amplification, or gain with respect to a reference after treatment with a bone modifying agent and/or an agent that avoids or prevents bone degradation, e.g., zoledronic acid. In embodiments, the overall survival of a subject without an increase of the c-MAF gene expression level, copy number, amplification, or gain with respect to a reference is longer after treatment a bone modifying agent and/or an agent that avoids or prevents bone degradation, e.g., zoledronic acid, than the overall survival of a subject with an increase in their c-MAF gene expression level, copy number, amplification, or gain with respect to a reference. In embodiments, the overall survival of a subject without an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more after treatment with zoledronic acid than the overall survival of a subject with an increase of the c-MAF gene expression level, copy number, amplification, or gain with respect to a reference after treatment with zoledronic acid. In embodiments, the subject is post menopausal. In other embodiments, the subject is non-post-menopausal. In some embodiments, the subject is premenopausal.

In embodiments, the disease free survival of a subject with an increase of the c-MAF gene expression level, copy number, amplification, or gain with respect to a reference is shorter after treatment a bone modifying agent and/or an agent that avoids or prevents bone degradation, e.g., zoledronic acid, than the disease free survival of a subject without an increase in their c-MAF gene expression level, copy number, amplification, or gain with respect to a reference. In embodiments, the disease free survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less after treatment a bone modifying agent and/or an agent that avoids or prevents bone degradation, e.g., zoledronic acid, than the disease free survival of a subject without an increase of the c-MAF gene expression level, copy number, amplification, or gain with respect to a reference after treatment a bone modifying agent and/or an agent that avoids or prevents bone degradation, e.g., zoledronic acid. In embodiments, the overall survival of a subject with an increase of the c-MAF gene expression level, copy number, amplification, or gain with respect to a reference is shorter after treatment a bone modifying agent and/or an agent that avoids or prevents bone degradation, e.g., zoledronic acid, than the overall survival of a subject without an increase in their c-MAF gene expression level, copy number, amplification, or gain with respect to a reference. In embodiments, the overall survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less after treatment a bone modifying agent and/or an agent that avoids or prevents bone degradation, e.g., zoledronic acid, than the overall survival of a subject without an increase of the c-MAF gene expression level, copy number, amplification, or gain with respect to a reference after treatment a bone modifying agent and/or an agent that avoids or prevents bone degradation, e.g., zoledronic acid. In embodiments, the subject is post menopausal. In other embodiments, the subject is non-post-menopausal. In some embodiments, the subject is premenopausal.

In embodiments, the disease free survival of non-post menopausal subject with an increase of the c-MAF gene expression level, copy number, amplification, or gain with respect to a reference is shorter after treatment a bone modifying agent and/or an agent that avoids or prevents bone degradation, e.g., zoledronic acid, than the disease free survival of a subject without an increase in their c-MAF gene expression level, copy number, amplification, or gain with respect to a reference. In embodiments, the disease free survival of a non-post menopausal subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more than 10 years less after treatment a bone modifying agent and/or an agent that avoids or prevents bone degradation, e.g., zoledronic acid, than the disease free survival of a subject without an increase of the c-MAF gene expression level, copy number, amplification, or gain with respect to a reference after treatment a bone modifying agent and/or an agent that avoids or prevents bone degradation, e.g., zoledronic acid.

In embodiments, the overall survival of a subject with an increase of the c-MAF gene expression level, copy number, amplification, or gain with respect to a reference is shorter after treatment a bone modifying agent and/or an agent that avoids or prevents bone degradation, e.g., zoledronic acid, than the disease free survival of a subject without an increase in their c-MAF gene expression level, copy number, amplification, or gain with respect to a reference. In embodiments, the overall survival of a subject with an increase in their c-MAF gene expression level, copy number, amplification, or gain with respect to a reference is at least about 1 month, 2 months, 3 months, 4 months, 5 months, 6 months, 7 months, 8 months, 9 months, 10 months, 11 months, 12 months, 1 year, eighteen months, 3 years, 4 years, 5 years, 6 years, 7 years, 8 years, 9 years, 10 years or more less after treatment a bone modifying agent and/or an agent that avoids or prevents bone degradation, e.g., zoledronic acid, than the overall survival of a subject without an increase of the c-MAF gene expression level, copy number, amplification, or gain with respect to a reference after treatment a bone modifying agent and/or an agent that avoids or prevents bone degradation, e.g., zoledronic acid. In embodiments, the subject is post menopausal. In other embodiments, the subject is non-post-menopausal. In some embodiments, the subject is premenopausal.

In embodiments, the predictive power of MAF for the OS or DFS of a subject is based on the menopausal status of the subject. In some embodiments, MAF is predictive in post-menopausal, unknown and perimenopausal subjects at risk of a shorter DFS or worst OS. In other embodiments, in premenopausal subjects, MAF positive subjects are those at less risk and are more likely to have a longer DFS and better OS.

In embodiments, the MAF status of the subject is predictive of the treatments that should be received by the subject. In embodiments, the c-MAF status in any of the embodiments herein includes 16923 or 16922-24 chromosomal locus amplification, copy gain or translocation or lack thereof, or 16q23 or 16q22-24 chromosomal locus deletions.

In embodiments, post-menopausal patients with an increase of the c-MAF gene expression level, copy number, amplification, or gain with respect to a reference (and are therefore at a high risk of a bad DFS or OS outcome) may be administered any treatment disclosed herein. In some embodiments, post menopausal patients with an increase of the c-MAF gene expression level, copy number, amplification, or gain with respect to a reference (and are therefore at a high risk of a bad DFS or OS outcome) may be treated by extending their hormonal treatment beyond the five year time prescribed by the use of hormonal treatments as the standard of care. In certain embodiments, the hormonal treatment is Tamoxifen and/or aromatase inhibitors. Patients without an increase of the c-MAF gene expression level, copy number, amplification, or gain with respect to a reference should not be administered a treatment disclosed herein.

In a particular embodiment, the subject has metastasis or a prognosis to undergo metastasis. In some embodiments, the metastasis is a bone metastasis. In a further embodiment, the bone metastasis is osteolytic metastasis.

In some embodiments, the sample is a primary tumor tissue sample of the subject. In a second step, the c-MAF gene expression level, copy number, amplification or gain obtained in the tumor sample of the subject is compared with the expression level, copy number, amplification or gain of said gene in a control sample. The determination of the c-MAF gene expression levels, copy number, amplification or gain must be related to values of a control sample or reference sample. Depending on the type of tumor to be analyzed, the exact nature of the control sample may vary. Thus, in some embodiments, the reference sample is a tumor tissue sample of a subject with breast cancer that has not metastasized, relapsed or reoccurred or that corresponds to the median value of the c-MAF gene expression levels, copy number, amplification or gain measured in a tumor tissue collection in biopsy samples of subjects with breast cancer which has not metastasized, relapsed or reoccurred.

In one embodiment, the methods of the invention comprise in a second step comparing the c-MAF gene expression level, copy number, amplification or gain obtained in the tumor sample (including but not limited to a primary tumor biopsy, circulating tumor cells and circulating tumor DNA) from the subject with the expression level of said gene in a control sample.

Once the c-MAF gene expression level, copy number, amplification or gain in a tumor tissue sample, a circulating tumor cell or circulating tumor DNA from a subject with breast cancer has been measured and compared with the control sample, if the expression level of said gene is increased with respect to its expression level in the control sample, then it can be concluded that said subject has a positive diagnosis for metastasis or a greater tendency to develop metastasis.

The determination of the c-MAF gene expression level, copy number, amplification or gain must be correlated with values of a control sample or reference sample. Depending on the type of tumor to be analyzed, the exact nature of the control sample may vary. Thus, in the event that a diagnosis is to be evaluated, then the reference sample is a tumor tissue sample from a subject with breast cancer that has not metastasized or that corresponds to the median value of the c-MAF gene expression levels measured in a tumor tissue collection in biopsy samples from subjects with breast cancer which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (c-MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least about 2, at least about 10, at least about 20, at least about 25, at least about 50, at least about 75, at least about 100, at least about 250, at least about 500, to more than 1000 subjects, classified according to the foregoing considerations, for example according to various age categories, are taken as the reference group. The sample collection from which the reference level is derived will preferably be formed by subjects suffering from the same type of cancer as the patient object of the study (e.g., breast cancer). Similarly, the reference value within a cohort of patients can be established using a receiving operating curve (ROC) and measuring the area under the curve for all de sensitivity and specificity pairs to determine which pair provides the best values and what the corresponding reference value is. ROC is a standard statistical concept. A description can be found in Stuart G. Baker "The Central Role of Receiver Operating Characteristic (ROC) curves in Evaluating Tests for the Early Detection of Cancer" *Journal of The National Cancer Institute* (2003) Vol 95, No. 7, 511-515.

Once this median or reference value has been established, the level of this marker expressed in tumor tissues from patients with this median value can be compared and thus be assigned, for example, to the "increased" expression level. Due to the variability among subjects (for example, aspects referring to age, race, etc.) it is very difficult (if not virtually impossible) to establish absolute reference values of c-MAF expression. Thus, in particular embodiments the reference values for "increased" or "reduced" expression of the c-MAF expression are determined by calculating the percentiles by conventional means which involves performing assays in one or several samples isolated from subjects whose disease is well documented by any of the methods mentioned above the c-MAF expression levels. The "reduced" levels of c-MAF can then preferably be assigned to samples wherein the c-MAF expression levels are equal to or lower than $50^{th}$ percentile in the normal population including, for example, expression levels equal to or lower than the $60^{th}$ percentile in the normal population, equal to or lower than the $70^{th}$ percentile in the normal population, equal to or lower than the $80^{th}$ percentile in the normal population, equal to or lower than the $90^{th}$ percentile in the normal population, and equal to or lower than the $95^{th}$ percentile in the normal population. The "increased" c-MAF gene expression levels can then preferably be assigned to samples wherein the c-MAF gene expression levels are equal to or greater than the $50^{th}$ percentile in the normal population including, for example, expression levels equal to or greater than the $60^{th}$ percentile in the normal population, equal to or greater than the $70^{th}$ percentile in the normal population, equal to or greater than the $80^{th}$ percentile in the normal population, equal to or greater than the $90^{th}$ percentile in the normal population, and equal to or greater than the $95^{th}$ percentile in the normal population.

In a particular embodiment, the degree of amplification or gain of the c-MAF gene can be determined by means of determining the amplification or gain of a chromosome region containing said gene. Preferably, the chromosome region the amplification or gain of which is indicative of the existence of amplification or gain of the c-MAF gene is the locus 16q22-q24 which includes the c-MAF gene. The locus 16q22-q24 is located in chromosome 16, in the long arm of said chromosome and in a range between band 22 and band 24. This region corresponds in the NCBI database with the contigs NT_010498.15 and NT_010542.15. In an embodiment, the degree of amplification or gain of the c-MAF gene can be determined by means of using a probe specific for said gene.

When copy number is measured, the control sample refers to a tumor sample of a subject with breast cancer who has not suffered metastasis or that correspond to the median value of the c-MAF gene copy number measured in a tumor tissue collection in biopsy samples of subjects with breast cancer who have not suffered metastasis. Said reference sample is typically obtained by combining equal amounts of samples from a subject population. If the c-MAF gene copy number is increased with respect to the copy number of said gene in the control sample, then subject has a positive diagnosis for metastasis or a greater tendency to develop metastasis. In embodiments, the copy number is determined as the average copy number per cell.

In some embodiments, the amplification or gain is in region at the 16q23 locus. In some embodiments, the amplification or gain is in any part of the chromosomal region between Chr. 16-79,392,959 bp to 79,663,806 bp (from centromere to telomere). In some embodiments, the amplification or gain is in the genomic region between Chr. 16—79,392,959 bp to 79,663,806 bp, but excluding DNA repeating elements. In some embodiments, amplification or gain is measured using a probe specific for that region.

In an embodiment, the c-MAF gene is amplified with respect to a reference gene copy number when the c-MAF gene copy number is higher than the copy number that a reference sample or control sample has. In one example, the c-MAF gene is said to be "amplified" if the genomic copy number or the average genomic copy number of the c-MAF gene is increased by at least about 2-, 3-, 4-, 5-, 6-, 7-, 8-, 9-, 10-, 15-, 20-, 25-, 30-, 35-, 40-, 45-, or 50-fold in a test sample relative to a control sample. In another example, a c-MAF gene is said to be "amplified" if the genomic copy number or the average genomic copy number of the c-MAF gene per cell is at least about 2.1, 2.2, 2.3, 2.4, 2.5, 2.6, 2.7, 2.8, 2.9, 3, 4, 5, 6, 7, 8, 9, 10, 11, 12, 13, 14, 15, 16, 17, 18, 19, 20, 21, 22, 23, 24, 25, 26, 27, 28, 29, 30, and the like.

In another embodiment, the reference gene copy number is the gene copy number in a sample of breast cancer from a subject who has not suffered bone metastasis.

In another embodiment, the amplification or gain is determined by means of in situ hybridization or PCR.

In another embodiment and as described in the present invention, given that the chr16q22-24, including the c-MAF gene, is amplified in breast cancer cells is related to the presence of metastasis, relapse or recurrence the chr16q22-24, including the c-MAF gene, amplification or gain allow making decisions in terms of the most suitable therapy for the subject suffering said cancer.

The determination of the amplification of the c-MAF gene needs to be correlated with values of a control sample or reference sample that correspond to the level of amplification of the c-MAF gene measured in a tumor tissue sample of a subject with breast cancer who has not suffered metastasis or that correspond to the median value of the amplification of the c-MAF gene measured in a tumor tissue collection in biopsy samples of subjects with breast cancer who have not suffered metastasis. Said reference sample is typically obtained by combining equal amounts of samples from a subject population.

In general, the typical reference samples will be obtained from subjects who are clinically well documented and in whom the absence of metastasis is well characterized. The sample collection from which the reference level is derived will preferably be made up of subjects suffering the same type of cancer as the patient object of the study. Once this median value has been established, the level of amplification of c-MAF in tumor tissues of patients can be compared with this median value, and thus, if there is amplification, the subject has a positive diagnosis of metastasis or a greater tendency to develop metastasis.

In another aspect, the invention relates to determining if the c-MAF gene is translocated in a sample of said subject.

In some embodiments, the translocated gene is from the region at the 16q23 locus. In some embodiments, the translocated gene is from any part of the chromosomal region between Chr. 16-79,392,959 bp to 79,663,806 bp (from centromere to telomere). In some embodiments, the translocated gene is from the genomic region between Chr. 16—79,392,959 bp to 79,663,806 bp, but excluding DNA repeating elements. In some embodiments, the translocation is measured using a probe specific for that region.

In a particular embodiment, the translocation of the c-MAF gene can be determined by means of determining the translocation of a chromosome region containing said gene. In one embodiment, the translocation is the t(14,16) translocation. In another embodiment, the chromosome region that is translocated is from locus 16q22-q24. The locus 16q22-q24 is located in chromosome 16, in the long arm of said chromosome and in a range between band 22 and band 24. This region corresponds in the NCBI database with the contigs NT_010498.15 and NT_010542.15. In an embodiment, the c-MAF gene translocates to chromosome 14 at the locus 14q32, resulting in the translocation t(14,16)(q32, q23). This translocation places the MAF gene next to the strong enhancers in the IgH locus, which, in some cases, leads to overexpression of MAF. (Eychène, A., Rocques, N., and Puoponnot, C., A new MAFia in cancer. 2008. *Nature Reviews: Cancer.* 8: 683-693.)

In an embodiment, the translocation of the c-MAF gene can be determined by means of using a probe specific for said translocation.

One embodiment of the invention comprises a method in which in a first step it is determined if the c-MAF gene is translocated in a sample of a subject. In an embodiment, the sample is a tumor tissue sample.

In a particular embodiment, a method of the invention for the prognosis of the tendency to develop bone metastasis in a subject with breast cancer comprises determining the c-MAF gene copy number in a sample of said subject wherein the c-MAF gene is translocated and comparing said copy number with the copy number of a control or reference sample, wherein if the c-MAF copy number is greater with respect to the c-MAF copy number of a control sample, then the subject has a greater tendency to develop bone metastasis.

Methods for determining whether the c-MAF gene or the chromosome region 16q22-q24 is translocated are widely known in the state of the art and include those described previously for the amplification of c-MAF. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, the gain, the copy number, or the translocation can be determined by counting the number of fluorescent points, colored points or points with silver in the chromosomes or in the nucleus. In other embodiments, the detection of copy number alterations and translocations can be detected through the use of whole genome sequencing, exome sequencing or by the use of any PCR derived technology. For instance, PCR can be performed on samples of genomic DNA to detect translocation. In one embodiment, quantitative PCR is used. In one embodiment, PCR is performed with a primer specific to the c-MAF gene and a primer specific to the IGH promoter region; if a product is produced, translocation has occurred.

In some embodiments, the amplification, gain and copy number of the c-MAF gene are determined after translocation of the c-MAF gene is determined. In some embodiments, a probe is used to determine if the cell is polyploid for the c-MAF gene. In some embodiments, a determination of polyploidy is made by determining if there are more than 2 signals from the gene of interest. In some embodiments, polyploidy is determined by measuring the signal from the probe specific for the gene of interest and comparing it with a centromeric probe or other probe.

Methods of Measuring c-MAF Expression, Copy Number, Amplification, Gain and Translocation In some embodiments, the c-MAF gene expression level, copy number, amplification, gain or translocation is measured using any method known in the art or described herein.

The c-MAF protein expression level can be quantified by any conventional method that allows detecting and quantifying said protein in a sample from a subject. By way of non-limiting illustration, said protein levels can be quantified, for example, by using antibodies with c-MAF binding capacity (or a fragment thereof containing an antigenic determinant) and the subsequent quantification of the complexes formed. The antibodies used in these assays may or may not be labeled. Illustrative examples of markers that can be used include radioactive isotopes, enzymes, fluorophores, chemiluminescence reagents, enzyme substrates or cofactors, enzyme inhibitors, particles, dyes, etc. There is a wide range of known assays that can be used in the present invention which use unlabeled antibodies (primary antibody) and labeled antibodies (secondary antibody); these techniques include Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies or assays based on colloidal precipitation in formats such as dipsticks. Other ways for detecting and quantifying said c-MAF protein include affinity chromatography techniques, ligand binding assays, etc. When an immunological method is used, any antibody or reagent that is known to bind to the c-MAF protein with a high affinity can be used for detecting the amount thereof. This would include, but is not limited to, the use of an antibody, for example, polyclonal sera, supernatants of hybridomas or monoclonal antibodies, antibody fragments, Fv, Fab, Fab' and F(ab')2, scFv, humanized diabodies, triabodies, tetrabodies, antibodies, nanobodies, alphabodies, stapled peptides, and cyclopeptides. There are commercial anti-c-MAF protein antibodies on the market which can be used in the context of the present invention, such as for example antibodies ab427, ab55502, ab55502, ab72584, ab76817, ab77071 (Abcam plc, 330 Science Park, Cambridge CB4 0FL, United Kingdom), the 075444 monoclonal antibody (Mouse Anti-Human MAF Azide free Monoclonal antibody, Unconjugated, Clone 6b8) of AbD Serotec, etc. There are many commercial companies offering anti-c-MAF antibodies, such as Abnova Corporation, Bethyl Laboratories, Bioworld Technology, GeneTex, etc.

In some embodiments, the c-MAF protein levels are detected by an antigen binding member or fragment thereof. In some embodiments, the binding member is an antigen binding molecule or fragment thereof that binds to human c-MAF, wherein the antibody binding molecule or fragment thereof comprises a heavy chain CDR1 at least about 70%, about 75%, about 80%, about 85%, about 90%, about 95%, about 99% or about 100% identical to the amino acid sequence of SEQ ID NO: 21, and/or a heavy chain CDR2 at least about 70%, about 75%, about 80%, about 85%, about 90%, about 95%, about 99% or about 100% identical to the amino acid sequence of SEQ ID NO: 22, and/or a heavy chain CDR3 at least about 70%, about 75%, about 80%, about 85%, about 90%, about 95%, about 99% or about 100% identical to the amino acid sequence of SEQ ID NO: 23; and/or comprising a light chain CDR1 at least about 70%, about 75%, about 80%, about 85%, about 90%, about 95%, about 99% or about 100% identical to the amino acid sequence of SEQ ID NO: 18, and/or a light chain CDR2 at least about 70%, about 75%, about 80%, about 85%, about 90%, about 95%, about 99% or about 100% identical to the amino acid sequence of SEQ ID NO: 19 and/or a light chain CDR3 at least about 70%, about 75%, about 80%, about 85%, about 90%, about 95%, about 99% or about 100% identical to the amino acid sequence of SEQ ID NO: 20.

In some embodiments, the antibody or fragment thereof comprises a VH domain with a sequence that is at least about 70%, at least about 75%, at least about 80%, at least about 85%, at least about 90%, at least about 95%, at least about 99%, or at least about 100% identical to the amino acid sequence of SEQ ID NO: 15.

In some embodiments, the antigen binding molecule or fragment thereof comprises a VL domain with a sequence that is at least about 70%, at least about 75%, at least about 80%, at least about 85%, at least about 90%, at least about 95%, at least about 99%, or at least about 100% identical to the amino acid sequence of SEQ ID NO: 17.

In some embodiments, the antibody or fragment thereof comprises a heavy chain sequence that is at least about 70%, at least about 75%, at least about 80%, at least about 85%, at least about 90%, at least about 95%, at least about 99%, or at least about 100% identical to the amino acid sequence of SEQ ID NO: 14.

In some embodiments, the antibody or fragment thereof comprises a light chain sequence that is at least about 70%, at least about 75%, at least about 80%, at least about 85%, at least about 90%, at least about 95%, at least about 99%, or at least about 100% identical to the amino acid sequence of SEQ ID NO: 16.

In some embodiments, the antigen binding molecule or fragment thereof is an antibody. In some embodiments, the antibody is a rabbit antibody, a mouse antibody, a chimeric antibody or a humanized antibody. In one aspect, the present invention is directed to a binding member, functional fragment, antibody or variant thereof that specifically binds to the epitope encoded by SEQ ID NO: 24. In some embodiments, the antibody is any antibody described in Int'l. Appl. No. PCT/IB2015/059562, which is incorporated herein by reference in its entirety.

In a particular embodiment, the c-MAF protein levels are quantified means of western blot, immunohistochemistry, ELISA or a protein array.

As understood by the person skilled in the art, the gene expression levels can be quantified by measuring the messenger RNA levels of said gene or of the protein encoded by said gene. In some embodiment, the gene expression level can be quantified by any means known in the art.

For this purpose, the biological sample can be treated to physically or mechanically break up the tissue or cell structure, releasing the intracellular components into an aqueous or organic solution for preparing nucleic acids. The nucleic acids are extracted by means of commercially available methods known by the person skilled in the art (Sambroock, J., et al., "Molecular cloning: a Laboratory Manual", 3rd ed., Cold Spring Harbor Laboratory Press, N.Y., Vol. 1-3.)

Thus, the c-MAF gene expression level can be quantified from the RNA resulting from the transcription of said gene (messenger RNA or mRNA) or, alternatively, from the complementary DNA (cDNA) of said gene. Therefore, in a particular embodiment of the invention, the quantification of the c-MAF gene expression levels comprises the quantification of the messenger RNA of the c-MAF gene or a fragment of said mRNA, complementary DNA of the c-MAF gene or a fragment of said cDNA or the mixture thereof.

Virtually any conventional method can be used within the scope of the invention for detecting and quantifying the mRNA levels encoded by the c-MAF gene or of the corresponding cDNA thereof. By way of non-limiting illustration, the mRNA levels encoded by said gene can be quantified using conventional methods, for example, methods comprising mRNA amplification and the quantification of said mRNA amplification product, such as electrophoresis and staining, or alternatively, by Southern blot and using suitable probes, Northern blot and using specific probes of the mRNA of the gene of interest (c-MAF) or of the corresponding cDNA thereof, mapping with S1 nuclease, RT-PCR, hybridization, microarrays, etc., preferably by means of real time quantitative PCR using a suitable marker. Likewise, the cDNA levels corresponding to the mRNA encoded by the c-MAF gene can also be quantified by means of using conventional techniques; in this case, the method of the invention includes a step for synthesizing the corresponding cDNA by means of reverse transcription (RT) of the corresponding mRNA followed by the amplification and quantification of said cDNA amplification product. Conventional methods for quantifying expression levels can be found, for example, in Sambrook et al., 2001. (cited ad supra). These methods are known in the art and a person skilled in the art would be familiar with the normalizations necessary for each technique. For example, the expression measurements generated using multiplex PCR should be normalized by comparing the expression of the genes being measured to so called "housekeeping" genes, the expression of which should be constant over all samples, thus providing a baseline expression to compare against or other control genes whose expression are known to be modulated with cancer.

In a particular embodiment, the c-MAF gene expression levels are quantified by means of quantitative polymerase chain reaction (PCR) or a DNA, RNA array, or nucleotide hybridization technique.

In addition, the c-MAF gene expression level can also be quantified by means of quantifying the expression levels of the protein encoded by said gene, e.g., the c-MAF protein (c-MAF) [NCBI, accession number 075444], or any functionally equivalent variant of the c-MAF protein. There are two c-MAF protein isoforms, the a isoform (NCBI, NP_005351.2) made up of 403 amino acids (SEQ ID NO: 4) and the R isoform (NP_001026974.1) made up of 373 amino acids (SEQ ID NO: 5). The c-MAF gene expression level can be quantified by means of quantifying the expression levels of any of the c-MAF protein isoforms. Thus, in a particular embodiment, the quantification of the levels of the protein encoded by the c-MAF gene comprises the quantification of the c-MAF protein.

Methods for determining whether the c-MAF gene or the chromosome region 16q22-q24 is amplified are widely known in the state of the art. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, gain or the copy number can be determined by counting the number of fluorescent points, colored points or points with silver in the chromosomes or in the nucleus.

The fluorescence in situ hybridization (FISH) is a cytogenetic technique which is used for detecting and locating the presence or absence of specific DNA sequences in chromosomes. FISH uses fluorescence probes which only bind to some parts of the chromosome with which they show a high degree of sequence similarity. In a typical FISH method, the DNA probe is labeled with a fluorescent molecule or a hapten, typically in the form of fluor-dUTP, digoxigenin-dUTP, biotin-dUTP or hapten-dUTP which is incorporated in the DNA using enzymatic reactions, such as nick translation or PCR. The sample containing the genetic material (the chromosomes) is placed on glass slides and is denatured by a formamide treatment. The labeled probe is then hybridized with the sample containing the genetic material under suitable conditions which will be determined by the person skilled in the art. After the hybridization, the sample is viewed either directly (in the case of a probe labeled with fluorine) or indirectly (using fluorescently labeled antibodies to detect the hapten).

In the case of CISH, the probe is labeled with digoxigenin, biotin or fluorescein and is hybridized with the sample containing the genetic material in suitable conditions.

Methods for determining whether the c-MAF gene or the chromosome region 16q22-q24 is translocated are widely known in the state of the art and include those described previously for the amplification of c-MAF. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification, the gain, the copy number, or the translocation can be determined by counting the number of fluorescent points, colored points or points with silver in the chromosomes or in the nucleus. In other embodiments, the detection of copy number alterations and translocations can be detected through the use of whole genome sequencing, exome sequencing or by the use of any PCR derived technology. For instance, PCR can be performed on samples of genomic DNA to detect translocation. In one embodiment, quantitative PCR is used. In one embodiment, PCR is performed with a primer specific to the c-MAF gene and a primer specific to the IGH promoter region; if a product is produced, translocation has occurred.

Any marking or labeling molecule which can bind to a DNA can be used to label the probes used in the methods of the invention, thus allowing the detection of nucleic acid molecules. Examples of labels for the labeling include, although not limited to, radioactive isotopes, enzyme substrates, cofactors, ligands, chemiluminescence agents, fluorophores, haptens, enzymes and combinations thereof. Methods for labeling and guideline for selecting suitable labels for different purposes can be found, for example, in Sambrook et al. (Molecular Cloning: A Laboratory Manual, Cold Spring Harbor, New York, 1989) and Ausubel et al. (In Current Protocols in Molecular Biology, John Wiley and Sons, New York, 1998).

In some embodiments, a probe of the invention is a dual color probe. In some embodiments, a probe of the invention is a dual fusion probe. In some embodiments, a probe of the invention is a dual color, dual fusion probe. In some embodiments, two separate probes are used.

In another embodiment, one of the following probes is used to measure the c-MAF gene (including translation of the c-MAF gene): the Vysis LSI IGH/MAF Dual Color dual fusion probe (http://www.abbottmolecular.com/us/products/analyte-specific-reagent/fish/vysis-lsi-igh-maf-dual-color-dual-fusion-probe.html; last accessed Nov. 5, 2012), which comprises a probe against 14q32 and 16923; a Kreatech diagnostics MAF/IGH gt(14;16) Fusion probe (https://www.leicabiosystems.com/fileadmin/img_uploads/kreatech/ifu/PI-KI-10610_D2.1.pdf; last accessed May 18, 2017), an Abnova MAF FISH probe (http://www.abnova.com/products/products_detail.asp?Catalog_id=FA0375; last accessed Nov. 5, 2012), a Cancer Genetics Italia IGH/MAF Two Color, Two Fusion translocation probe (http://www.cancer-geneticsitalia.com/dna-fish-probe/ighmaf/; last accessed Nov. 5, 2012), a Creative Bioarray IGH/MAF-t(14;16)(q32;q23) FISH probe (http://www.creative-bioarray.com/products.asp?cid=35&page=10; last accessed Nov. 5, 2012), a Arup Laboratories multiple myeloma panel by FISH (http://www.aruplab.com/files/technical-bulletins/Multiple %20Myeloma %20%28MM %29%20by %20FISH.pdf; last accessed Nov. 5, 2012), an Agilent probe specific to 16q23 or 14q32 (http://www.genomics.agilent.com/ProductSearch.aspx?chr=16&start=79483700&end=79754340; last accessed Nov. 5, 2012; http://www.genomics.agilent.com/ProductSearch.aspx?Pageid=3000&ProductID=637; last accessed Nov. 5, 2012), a Dako probe specific to 16q23 or 14q32 (http://www.dako.com/us/ar42/psg42806000/baseproducts_surefish.htm?setCountry=true&purl=ar42/psg42806000/baseproducts_surefish.htm?undefined&submit=Accept %20country; last accessed Nov. 5, 2012), a Cytocell IGH/MAF Translocation, Dual Fusion Probe (http://www.zentech.be/uploads/docs/products_info/prenatalogy/cytocell %202012-2013%20catalogue %5B3%5D.pdf, last accessed Nov. 5, 2012), a Metasystems XL IGH/MAF Translocation—Dual Fusion Probe (http://www.metasystems-international.com/index.php?option=com_joodb&view=article&joobase=5&id=12%3Ad-5029-100-og&Itemid=272; last accessed Nov. 5, 2012), a Zeiss FISH Probes XL, 100 µl, IGH/MAFB (https://www.micro-shop.zeiss.com/?s=440675675 dedc6&l=en&p=uk&f=r&i=5000&o=&h=25&n=1&sd=00 0000-0528-231-uk; last accessed Nov. 5, 2012) or a Genycell Biotech IGH/MAF Dual Fusion Probe (http://www.google.com/url?sa=t&rct=j&q=&esrc=s& source=web&cd=1&ved=0CCQQFjAA&url=http %3A %2F %2Fwww.genycell.es %2Fimages %2Fproductos %2Fbrochures %2Flphmie6__86.ppt&ei= MhGYUOi3GKWH0QGlt4DoDw&usg=AFQjCNEq QMbT8vQGjJbi9riEf31VgoFTFQ&sig2=V5IS8juE MVHB18Mv2Xx_Ww; last accessed Nov. 5, 2012)

In some embodiments, the label on the probe is a fluorophore. In some embodiments, the fluorophore on the probe is orange. In some embodiments, the fluorophore on the probe is green. In some embodiments, the fluorophore on the probe is red. In some cases, the fluorophore on the probe is yellow. In some embodiments, one probe is labeled with a red fluorophore, and one with a green fluorophore. In some embodiments, one probe is labeled with a green fluorophore and one with an orange fluorophore. In some cases, the fluorophore on the probe is yellow. For instance, if the MAF-specific probe is labeled with a red fluorophore, and the IGH-specific probe is labeled with a green fluorophore, if white is seen it indicates that the signals overlap and translocation has occurred.

In some embodiments, the fluorophore is SpectrumOrange. In some embodiments, the fluorophore is SpectrumGreen. In some embodiments, the fluorophore is DAPI. In some embodiments, the fluorophore is PlatinumBright405 In some embodiments, the fluorophore is PlatinumBright415. In some embodiments, the fluorophore is PlatinumBright495. In some embodiments, the fluorophore is PlatinumBright505. In some embodiments, the fluorophore is PlatinumBright550. In some embodiments, the fluorophore is PlatinumBright547. In some embodiments, the fluorophore is PlatinumBright570. In some embodiments, the fluorophore is PlatinumBright590. In some embodiments, the fluorophore is PlatinumBright647. In some embodiments, the fluorophore is PlatinumBright495/550. In some embodiments, the fluorophore is PlatinumBright415/495/550. In some embodiments, the fluorophore is DAPI/PlatinumBright495/550. In some embodiments, the fluorophore is FITC. In some embodiments, the fluorophore is Texas Red. In some embodiments, the fluorophore is DEAC. In some embodiments, the fluorophore is R6G. In some embodiments, the fluorophore is Cy5. In some embodiments, the fluorophore is FITC, Texas Red and DAPI. In some embodiments, a DAPI counterstain is used to visualize the translocation, amplification, gain or copy number alteration.

Agents and Therapies for Use in Methods for Treatment or Prevention of Breast Cancer In some embodiments, the methods of the invention herein include treating subjects with agents for avoiding, treating or preventing bone remodeling. As used herein, an "agent for avoiding, treating or preventing bone remodeling" refers to any molecule capable of treating or stopping bone degradation either by stimulating the osteoblast proliferation or inhibiting the osteoclast proliferation, including agents for avoiding, treating or preventing bone degradation. In embodiments, the agent for avoiding or preventing bone remodeling is a bone modifying agent and/or an agent that avoids, treats or prevents bone degradation. In embodiments, the agents for avoiding, treating or preventing bone remodeling are used as adjuvant therapies. In other embodiments, the agents for avoiding, treating or preventing bone remodeling are used as neoadjuvant therapies. Illustrative examples of agents used for avoiding, treating and/or preventing bone degradation include those agents disclosed in U.S. application Ser. No. 14/391,085, U.S. Prov. Appl. No. 61/801,769, U.S. Prov. application Ser. No. 14/776,390, U.S. application Ser. No. 14/776,412, U.S. application Ser. No. 14/405,724, U.S. application Ser. No. 14/050,262, U.S. application Ser. No. 14/435,128, U.S. application Ser. No. 15/027,946 U.S. application Ser. No. 15/014,916, U.S. application Ser. No. 15/534,893 and U.S. application Ser. No. 14/776,453 and Int'l Appl. No. PCT/IB2017/053094 including the following agents: Bisphosphonates: are a group of medicinal products used for the prevention and the treatment of diseases with bone resorption and reabsorption such as osteoporosis and cancer with bone metastasis, the latter being with or without hypercalcemia, associated to breast cancer. Examples of bisphosphonates which can be used in the therapy designed by means of any method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.). In a particular embodiment, the bisphosphonate is zoledronic acid. In a different embodiment, the bisphosphonate is clodronate. In one embodiment, the bisphosphonate is alendronate, risedronate, or ibandronate. The use of bisphosphonates, zoledronic acid, clodronate, alendronate, risedronate, or ibandronate as adjuvant treatments in early breast cancer, including clinical trial data, can be found in Hadji et al., *Annals of Oncology,* 27: 379-390 (2016); Paterson et al., J. Clin. Med. 2(4): 263-301 (2013). In embodiments, various aspects of clodronate are covered by, for example, U.S. Pat. No. 4,859,472 and Int'l Appl. No. WO1995013054 (the entire contents of each of which are hereby incorporated by reference in their entirety). In embodiments, clodronate is represented by the following formula:

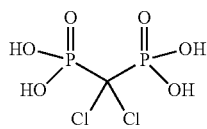

Guidelines for the adjuvant use of bisphosphonates can be found DHESY-THIND, S., et al., *J Clin Oncol* 35, American Society of Clinical Oncology, United States, 22 pages (published online before print Mar. 6, 2017) (the entire contents of which are hereby incorporated by reference). A clinical trial describing the use of clodronate as an adjuvant treatment is described in PATERSON, A. H. G., et al., *The Lancet Oncology* 13(7):734-742, (2012) (the entire contents of which is hereby incorporated by reference). A clinical trial describing the use of zoledronic acid is described in AZURE Trial Protocol for: COLEMAN, R. E., et al., *The New England Journal of Medicine* 365(15):1396-1405, (2011) and COLEMAN, R. E., et al., *The New England Journal of Medicine* 365(15):1396-1405, (2011) (the entire contents of which are hereby incorporated by reference). In embodiments, the bisphosphonate is administered intravenously. In other embodiments, the bisphosphonate is administered orally.

"RANKL inhibitors" as used herein refer to any compound which is capable of reducing the RANK activity.

In one embodiment, the RANKL inhibitor is a RANKL specific antibody. In a specific embodiment, the anti-RANKL antibody is a monoclonal antibody. In a yet more specific embodiment, the anti-RANKL antibody is Denosumab (Pageau, Steven C. (2009). mAbs 1 (3): 210-215, CAS number 615258-40-7) (the entire contents of which are hereby incorporated by reference). Denosumab is a fully human monoclonal antibody which binds to RANKL and prevents its activation (it does not bind to the RANK receptor). In embodiments, various aspects of Denosumab are covered by U.S. Pat. Nos. 6,740,522; 7,411,050; 7,097, 834; 7,364,736; 7,411,050; 7,744,886; 7,923,008; 8,058, 418; 8,333,963; 8,377,690; and 8,409,578 (the entire contents of each of which are hereby incorporated by reference in their entirety). Canadian guidelines for the use of Denosumab can be found in Paterson et al., J. Clin. Med. 2(4): 263-301 (2013) (the entire contents of which is hereby incorporated by reference). A clinical trial describing the use of denosumab can be found in https://clinicaltrials.gov/ct2/show/NCT01077154 (last visited Aug. 25, 2017) (the entire contents of which is hereby incorporated by reference). In another embodiment, the RANKL inhibitor is an antibody, antibody fragment, or fusion construct that binds the same epitope as Denosumab. In embodiments, the Denosumab is administered subcutaneously.

In an embodiment, the agent preventing the bone degradation is selected from the group consisting of zoledronic acid, clodronate, and denosumab.

Alternatively a combined treatment can be carried out in which more than one agent from those mentioned above or one or more agents disclosed herein or disclosed in U.S. application Ser. No. 14/391,085, U.S. Prov. Appl. No. 61/801,769, U.S. Prov. application Ser. No. 14/776,390, U.S. application Ser. No. 14/776,412, U.S. application Ser. No. 14/405,724, U.S. application Ser. No. 14/050,262, U.S. application Ser. No. 14/435,128, U.S. application Ser. No. 15/027,946 U.S. application Ser. No. 15/014,916, U.S. application Ser. No. 15/534,893, U.S. application Ser. No. 14/776,453 and Int'l Appl. No. PCT/IB2017/053094, each of which is incorporated herein by reference in its entirety, are combined to treat and/or prevent the metastasis, relapse or recurrence or said agents can be combined with other supplements, such as calcium or vitamin D or combined with a hormone treatment.

In embodiments, patients are treated in the adjuvant setting with any therapy to improve the outcome of the patients. These therapies include any therapy disclosed herein or one or more agents disclosed herein or disclosed in U.S. application Ser. No. 14/391,085, U.S. Prov. Appl. No. 61/801,769, U.S. Prov. application Ser. No. 14/776,390, U.S. application Ser. No. 14/776,412, U.S. application Ser. No. 14/405,724, U.S. application Ser. No. 14/050,262, U.S. application Ser. No. 14/435,128, U.S. application Ser. No. 15/027,946 U.S. application Ser. No. 15/014,916, U.S. application Ser. No. 15/534,893 and U.S. application Ser. No. 14/776,453 and Int'l Appl. No. PCT/IB2017/053094, each of which is incorporated herein by reference in its entirety, including agents for avoiding, treating or preventing bone remodeling, agents to improve disease free survival or overall survival, c-MAF inhibitory agents, chemotherapy, hormone therapy, m-Tor inhibitors, CDK4/6 inhibitors, Radium-223, a CCR5 antagonist, a Src kinase inhibitor, or a COX-2 inhibitor and combinations thereof.

When the cancer has metastasized, systemic treatments including but not limited to chemotherapy, hormone treatment, immunotherapy, or a combination thereof are used. Additionally, radiotherapy and/or surgery can be used. The choice of treatment generally depends on the type of primary cancer, the size, the location of the metastasis, the age, the general health of the patient and the types of treatments used previously.

The systemic treatments are those that reach the entire body:
Chemotherapy is the use of medicaments to destroy cancer cells. The medicaments are generally administered through oral or intravenous route. In other embodiments, the treatment is chemotherapy. In some embodiments, the chemotherapy is any chemotherapy that is known in the art. In particular embodiments, the chemotherapy is adjuvant chemotherapy. In certain embodiments, the chemotherapy is a taxane. In further embodiments, the taxane is Paclitaxel (Taxol), docetaxel (Taxotere) or Cabazitaxel. The medicaments are generally administered through oral or intravenous route. Sometimes, chemotherapy is used together with radiation treatment. Hormone therapy is based on the fact that some hormones promote cancer growth. For example, estrogen in women produced by the ovaries sometimes promotes the breast cancer growth. There are several ways for stopping the production of these hormones. A way is to remove the organs producing them: the ovaries in the case of women, the testicles in the case of the men. More frequently, medicaments to prevent these organs from producing the hormones or to prevent the hormones from acting on the cancer cells can be used. In embodiments, the treatment is hormone therapy. In certain embodiments, the hormone therapy is Tamoxifen and/or an aromatase inhibitor.
Immunotherapy is a treatment that aids the immune system itself of the patient to combat cancer. There are several types of immunotherapy which are used to treat metastasis patients. These include but are not limited to cytokines, monoclonal antibodies and antitumor vaccines.

The agents for avoiding, treating or preventing bone remodelling are typically administered in combination with a pharmaceutically acceptable carrier.

The term "carrier" refers to a diluent or an excipient whereby the active ingredient is administered. Such pharmaceutical carriers can be sterile liquids such as water and oil, including those of a petroleum, animal, plant or synthetic origin such peanut oil, soy oil, mineral oil, sesame oil and the like. Water or aqueous saline solutions and aqueous dextrose and glycerol solutions, particularly for injectable solutions, are preferably used as carriers. Suitable pharmaceutical carriers are described in "Remington's Pharmaceutical Sciences" by E. W. Martin, 1995. Preferably, the carriers of the invention are approved by the state or federal government regulatory agency or are listed in the United States Pharmacopeia or other pharmacopeia generally recognized for use thereof in animals and more particularly in human beings.

The carriers and auxiliary substances necessary for manufacturing the desired pharmaceutical dosage form of the pharmaceutical composition of the invention will depend, among other factors, on the pharmaceutical dosage form chosen. Said pharmaceutical dosage forms of the pharmaceutical composition will be manufactured according to the conventional methods known by the person skilled in the art. A review of the different methods for administering active ingredients, excipients to be used and processes for producing them can be found in "Tratado de Farmacia Galénica", C. Fauli i Trillo, Luzán 5, S.A. 1993 Edition. Examples of pharmaceutical compositions include any solid composition (tablets, pills, capsules, granules, etc.) or liquid composition (solutions, suspensions or emulsions) for oral, topical or parenteral administration. Furthermore, the pharmaceutical composition may contain, as deemed necessary, stabilizers, suspensions, preservatives, surfactants and the like.

For use in medicine, the bone remodelling agents can be found in the form of a prodrug, salt, solvate or clathrate, either isolated or in combination with additional active agents and can be formulated together with a pharmaceutically acceptable excipient. Excipients preferred for use thereof in the present invention include sugars, starches, celluloses, rubbers and proteins. In a particular embodiment, the pharmaceutical composition of the invention will be formulated in a solid pharmaceutical dosage form (for example tablets, capsules, pills, granules, suppositories, sterile crystal or amorphous solids that can be reconstituted to provide liquid forms etc.), liquid pharmaceutical dosage form (for example solutions, suspensions, emulsions, elixirs, lotions, ointments etc.) or semisolid pharmaceutical dosage form (gels, ointments, creams and the like). The pharmaceutical compositions of the invention can be administered by any route, including but not limited to the oral route, intravenous route, intramuscular route, intraarterial route, intramedulary route, intrathecal route, intraventricular route, transdermal route, subcutaneous route, intraperitoneal route, intranasal route, enteric route, topical route, sublingual route or rectal route. A review of the different ways for administering active ingredients, of the excipients to be used and of the manufacturing processes thereof can be found in Tratado de Farmacia Galénica, C. Fauli i Trillo, Luzán 5, S.A., 1993 Edition and in Remington's Pharmaceutical Sciences (A. R. Gennaro, Ed.), $20^{th}$ edition, Williams & Wilkins PA, USA (2000). Examples of pharmaceutically acceptable carriers are known in the state of art and include phosphate buffered saline solutions, water, emulsions such as oil/water emulsions, different types of wetting agents, sterile solutions, etc. The compositions comprising said carriers can be formulated by conventional processes known in the state of the art.

The bone remodelling-avoiding and preventing agents or the pharmaceutical compositions containing them can be administered at a dose of less than 10 mg per kilogram of body weight, preferably less than at least about 50, 40, 30, 20, 10, 5, 2, 1, 0.5, 0.1, 0.05, 0.01, 0.005, 0.001, 0.0005, 0.0001, 0.00005 or 0.00001 mg per kg of body weight. The unit dose can be administered by injection, inhalation or topical administration. In particular embodiments, the agent is administered at its approved dose.

The dose depends on the severity and the response of the condition to be treated and it may vary between several days and months or until the condition subsides. The optimal dosage can be determined by periodically measuring the concentrations of the agent in the body of the patient. The optimal dose can be determined from the EC50 values obtained by means of previous in vitro or in vivo assays in animal models. The unit dose can be administered once a day or less than once a day, preferably less than once every 2, 4, 8 or 30 days. Alternatively, it is possible to administer a starting dose followed by one or several maintenance doses, generally of a lesser amount than the starting dose. The maintenance regimen may involve treating the patient with a dose ranging between 0.01 µg and 1.4 mg/kg of body weight per day, for example 10, 1, 0.1, 0.01, 0.001, or 0.00001 mg per kg of body weight per day. The maintenance doses are preferably administered at the most once every 5, 10 or 30 days. The treatment must be continued for a time that will vary according to the type of disorder the patient suffers, the severity thereof and the condition of the patient. After treatment, the progress of the patient must be monitored to determine if the dose should be increased in the event that the disease does not respond to the treatment or the dose is reduced if an improvement of the disease is observed or if unwanted side effects are observed.

In embodiments, the terms "treatment" and "therapy" are used interchangeably.

In certain embodiments, the treatment is zoledronic acid. In embodiments, the zoledronic acid is administered in accordance with any dosing schedule in AZURE Trial Protocol for: COLEMAN, R. E., et al., *The New England Journal of Medicine* 365(15):1396-1405, (2011); COLEMAN, R. E., et al., *The New England Journal of Medicine* 365(15):1396-1405, (2011); Hadji et al., *Annals of Oncology*, 27: 379-390 (2016); or Paterson et al., *J. Clin. Med.* 2(4): 263-301 (2013) (the entire contents of which are hereby incorporated by reference).

In embodiments, the zoledronic acid is administered at a dose of about 1 mg to about 10 mg zoledronic acid, about 2 mg to about 9 mg of zoledronic acid, about 2 mg to about 8 mg of zoledronic acid, about 2 mg to about 7 mg of zoledronic acid, about 2 mg to about 6 mg of zoledronic acid, about 2 mg to about 5 mg of zoledronic acid, or about 3 mg to about 5 mg of zoledronic acid. The subject is administered about 1 mg, about 2 mg, about 3 mg, about 4 mg, about 5 mg, about 6 mg, about 7 mg, about 8 mg, about 9 mg, about 10 mg, about 12 mg, about 14 mg, or about 16 mg of zoledronic acid. In embodiments, the subject is administered about 4 mg of zoledronic acid.

In embodiments, the zoledronic acid is administered once about every 2 weeks, 3 weeks, 4 weeks, 5 weeks, 6 weeks, 8 weeks, 10 weeks, 12 weeks, 2 months, 3 months, 4 months, 5 months, 6 months, or 1 year. In certain embodiments, the zoledronic acid is administered once about every 3 weeks. In other embodiments, the zoledronic acid is administered once about every 4 weeks.

In some embodiments, the zoledronic acid is administered once about every 3 weeks for at least six initial doses. In other embodiments, the zoledronic acid is administered once about every 4 weeks for at least six initial doses. In certain embodiments, the initial dose of zoledronic acid is 4 mg.

In embodiments, the zoledronic acid is administered once about every 3 months for at least eight maintenance doses following the initial doses. In further embodiments, the zoledronic acid is administered once about every 6 months for up to five maintenance doses following the initial maintenance doses. In certain embodiments, the maintenance doses are about 4 mg of zoledronic acid.

In some embodiments, the zoledronic acid is administered at a dose of 4 mg once about every 3 weeks for at least six initial doses, followed by 4 mg once about every 3 months for at least eight maintenance doses, followed by 4 mg about every 6 months for up to five maintenance doses. In other embodiments, the zoledronic acid is administered at a dose of 4 mg once about every 3 weeks for at least six initial doses, followed by 4 mg once about every 3 months for at least eight maintenance doses, followed by 4 mg every 6 months for up to five maintenance doses.

In certain embodiments, the zoledronic acid is administered as an adjuvant therapy. In other embodiments, the zoledronic acid is administered as a neoadjuvant therapy. In certain embodiments, the zoledronic acid is administered with an additional therapy. In embodiments, the additional therapy is any therapy disclosed or referenced herein. In further embodiments, the zoledronic acid is administered prior to, concurrently with, or after the additional therapy. In embodiments, those patients treated with zoledronic acid injection have serum creatinine assessed prior to each treatment. In certain embodiments, patients administered zoledronic acid are also administered calcium and/or vitamin D.

In embodiments, the treatment is alendronate administered at a dose of about 50 mg to about 100 mg. In certain embodiments, the alendronate is administered at a dose of about 50 mg, about 60 mg, about 70 mg, about 80 mg, about 90 mg, or about 100 mg weekly. In certain embodiments, the alendronate is administered at a dose of about 70 mg weekly. In particular embodiments, the alendronate is administered orally. In certain embodiments, the alendronate is administered as an adjuvant therapy. In other embodiments, the alendronate is administered as a neoadjuvant therapy. In certain embodiments, the alendronate is administered with an additional therapy. In embodiments, the additional therapy is any therapy disclosed or referenced herein. In further embodiments, the alendronate is administered prior to, concurrently with, or after the additional therapy. In certain embodiments, patients administered alendronate are also administered calcium and/or vitamin D.

In embodiments, the treatment is risedronate administered at a dose of about 20 mg to about 50 mg. In certain embodiments, the risedronate is administered at a dose of about 20 mg, about 25 mg, about 30 mg, about 35 mg, about 40 mg, about 45 mg, or about 50 mg weekly. In certain embodiments, the risedronate is administered at a dose of about 35 mg weekly. In particular embodiments, the risedronate is administered orally. In certain embodiments, the risedronate is administered as an adjuvant therapy. In other embodiments, the risedronate is administered as a neoadjuvant therapy. In certain embodiments, the risedronate is administered with an additional therapy. In embodiments, the additional therapy is any therapy disclosed or referenced herein. In further embodiments, the risedronate is administered prior to, concurrently with, or after the additional therapy. In certain embodiments, patients administered risedronate are also administered calcium and/or vitamin D.

In embodiments, the treatment is ibandronate administered at a dose of about 100 mg to about 200 mg. In certain embodiments, the ibandronate is administered at a dose of about 100 mg, about 110 mg, about 120 mg, about 130 mg, about 140 mg, about 150 mg, about 160 mg, about 170 mg, about 180 mg, about 190 mg, or about 200 mg monthly. In certain embodiments, the ibandronate is administered at a dose of about 150 mg monthly. In particular embodiments, the ibandronate is administered orally. In certain embodiments, the ibandronate is administered as an adjuvant therapy. In other embodiments, the ibandronate is administered as a neoadjuvant therapy. In certain embodiments, the ibandronate is administered with an additional therapy. In embodiments, the additional therapy is any therapy disclosed or referenced herein. In further embodiments, the ibandronate is administered prior to, concurrently with, or after the additional therapy. In certain embodiments, patients administered ibandronate are also administered calcium and/or vitamin D.

In embodiments, the treatment is clodronate. In certain embodiments, the clodronate is administered in any dosing schedule described in Hadji et al., *Annals of Oncology*, 27: 379-390 (2016); Paterson et al., *J. Clin. Med.* 2(4): 263-301 (2013) or PATERSON, A. H. G., et al., *The Lancet Oncology* 13(7) (the entire contents of which are hereby incorporated by reference).

In embodiments, the clodronate is administered at a dose of about 1000 mg to about 2000 mg, about 1200 mg to about 2000 mg, about 1200 mg to about 1800 mg, about 1300 mg to about 1800 mg, or about 1400 mg to about 1800 mg. In particular embodiments, the clodronate is administered at a dose of about 1000 mg, about 1100 mg, about 1200 mg, about 1250 mg, about 1300 mg, about 1400 mg, about 1500 mg, about 1600 mg, about 1700 mg, about 1750 mg, about 1800 mg, about 1900 mg, or about 2000 mg. In certain embodiments, the clodronate is administered at a dose of about 1600 mg.

In certain embodiments, the clodronate is administered about once a day, about twice a day, about once a week, about once every two weeks, or about once a month. In particular embodiments, the clodronate is administered about once a day. In particular embodiments, the clodronate is administered orally at a dose of about 1600 mg about once a day.

In certain embodiments, the clodronate is administered orally. In certain embodiments, the clodronate administered as an adjuvant therapy. In other embodiments, the clodronate is administered as a neoadjuvant therapy. In certain embodiments, the clodronate is administered with an additional therapy. In embodiments, the additional therapy is any therapy disclosed or referenced herein. In further embodiments, the clodronate is administered prior to, concurrently with, or after the additional therapy. In certain embodiments, patients administered clodronate are also administered calcium and/or vitamin D.

In certain embodiments, the treatment is denosumab. In certain embodiments, the denosumjab is administered at any dosing schedule disclosed in Paterson et al., *J. Clin. Med.* 2(4): 263-301 (2013), Pageau, Steven C. (2009). mAbs 1 (3): 210-215, CAS number 615258-40-7, or https://clinicaltrials.gov/ct2/show/NCT01077154 (last visited Aug. 25, 2017) (the entire contents of which are hereby incorporated by reference).

In embodiments, the denosumab is administered at a dose of about 10 mg to about 300 mg, about 20 mg to about 300 mg, about 50 mg to about 300 mg, about 50 mg to about 250 mg, about 75 mg to about 250 mg, about 100 mg to about 250 mg, about 100 mg to about 200 mg, or about 100 mg to about 150 mg. In particular embodiments, the denosumab is administered at a dose of about 20 mg, about 30 mg, about 50 mg, about 75 mg, about 100 mg, about 110 mg, about 120 mg, about 130 mg, about 150 mg, about 175 mg, about 200 mg, about 225 mg, about 250 mg, about 275 mg, or about 300 mg. In embodiments, the denosumab is administered at a dose of the denosumab is administered at a dose of about 120 mg. In embodiments, the denosumab is administered at a dose of about 30 mg. In embodiments, the denosumab is administered at a dose of about 60 mg. In embodiments, the denosumab is administered at a dose about 180 mg.

In certain embodiments, the denosumab is administered once at least about every 1 week, 2 weeks, 3 weeks, 4 weeks, 1 month, 2 months, 3 months, 12 weeks, 4 months, 6 months or 1 year. In one embodiment, the denosumab is administered at a dose of once about every month for at least 6 months. In one embodiment, the denosumab is administered at a dose of 120 mg once about every month for at least 6 months. In a further embodiment, the denosumab is administered at a dose of 120 mg once about every month for at least 6 months, followed by a dose of 120 mg once about every 3 months for at least about 1 year, 2 years, 3 years, 4 years, 5 years or longer. In embodiments, the denosumab is administered at a dose of about 30 mg about once every 4 weeks. In other embodiments, the denosumab is administered at a dose of 120 mg about once every 4 weeks. In yet other embodiments, the denosumab is administered at a dose of 180 mg about once every 4 weeks. In further embodiments, the denosumab is administered at a dose of about 60 mg about once every 12 weeks. In other embodiments, the denosumab is administered at a dose of 180 mg about once every 12 weeks. In embodiments, the denosumab is administered subcutaneously. In certain embodiments, patients administered denosumab are also administered calcium and/or vitamin D.

In certain embodiments, the subject is additionally administered calcium. In embodiments, the calcium is administered once about every day. In embodiments, the calcium is administered orally. In certain embodiments, the calcium is administered at a dose of about 100 mg, about 200 mg, about 300 mg, about 400 mg, about 500 mg, about 600 mg, about 700 mg, about 800 mg, about 900 mg or about 1000 mg. In particular embodiments, the calcium is administered at a dose of at least about 500 mg. In some embodiments, the subject is additionally administered vitamin D. In particular embodiments, the vitamin D is administered once about every day. In embodiments the vitamin D is administered at a dose of about 100 IU, about 200 IU, about 300 IU, about 400 IU, and 500 IU, about 600 IU, about 700 IU, or about 800 IT. In particular embodiments, the vitamin D is administered at a dose of at least about 400 IU. In embodiments, the patient receiving the vitamin D and/or calcium is postmenopausal.

In some embodiments, the treatment is from a plastic bag or an IV bag. In embodiments, the drug is already diluted and corresponds to each dose. In other embodiments, the treatment has to be diluted. For example, see Ministry of Health, Social Services and Equality, Data Sheet of "Zoledronic acid Kern Pharma 4 mg/100 mL Solution for Infusion EFG," Text Revised July 2016, Machine-translated Jul. 6, 2017, 38 pages (Ministerio de Sanidad, Servicios Sociales e Igualdad, Ficha Tecnica de "Acido Zoledronico Kern Pharma 4 mg/100 ml Solucion Para Perfusion EFG"). Each plastic bag with 100 ml of solution contains 4 mg zoledronic acid, equivalent to 4.264 mg of monohydrate zoledronic acid. Each ml of the solution contains 0.04 mg of zoledronic acid, equivalent to 0.042 mg of monohydrate zoledronic acid. Each plastic bag of 100 ml solution contains 342.9 mg (14.9 mmol) of sodium.

In embodiments, treatments from the plastic bags are administered to the patients via IV. In some embodiments, the treatment are administered via intravenous perfusion. In certain embodiments, the perfusion occurs over a period of about 10 minutes to about 45 minutes. In other embodiments, the perfusion occurs over a period of about 10 minutes, about 15 minutes, about 20 minutes, about 25 minutes, about 30 minutes, about 40 minutes, about 45 minutes, or longer. In some embodiments, the perfusion occurs over a period of about 15 to 20 minutes.

In embodiments, the solutions in the plastic bags include excipients. In certain embodiments, these excipients include: Mannitol (E421), Sodium citrate (E331) or sodium citrate dihydrate, sodium chloride and/or water for injectable preparations.

In some embodiments, the treatments are in prefilled syringes. In other embodiments, the treatments are in prefilled vials. In certain embodiments, the prefilled vials must be further diluted for administration. In some embodiments, a prefilled vial is diluted by adding a sterile sodium chloride or dextrose solution (e.g., 100 ml of 0.9% Sodium Chloride, USP or 5% Dextrose Injection, USP).

'The following examples illustrate the invention and do not limit the scope thereof.

EXAMPLES

Example 1: Validation of c-MAF as a Metastasis Marker

The IHC and FISH assays used to test c-MAF in the AZURE samples were analytically validated. An overview of the assay validation parameters can be seen in FIG. 1.

The MAF FISH assay was produced by Kreatech for Inbiomotion based on Kreatech proprietary FISH technology. The probe set contains two probes: a MAF 16q23 probe plus a D16Z3 probe as control of chromosome 16 centromeric region. The assay was validated using a 16q23/D16Z3 probe (Inbiomotion) and Poseidon Tissue Digestion Kit from Kreatech. The scoring criteria were defined in a fact sheet and as follows: two FISH evaluable results per patient, and the highest value was selected. The scoring algorithm was as follows: 20 cells counted for target and centromere amplification, if the gene count is >2 and ≤3, then 50 cells were counted.

The MAF IHC assay was based on a recombinant monoclonal antibody (described in Int'l Appl. No. PCT/IB2015/059562, which is incorporated herein by reference in its entirety). The antibody was selected based on IHC. The assay was validated using MAF RecMab (Inbiomotion) with DAKO AS LINK platform and protocol on control specimens provided by Inbiomotion. The scoring criterion was defined upfront in a fact sheet, and there was one single IHC Hscore per patient. The scoring algorithm was the H-score.

Figure 3:
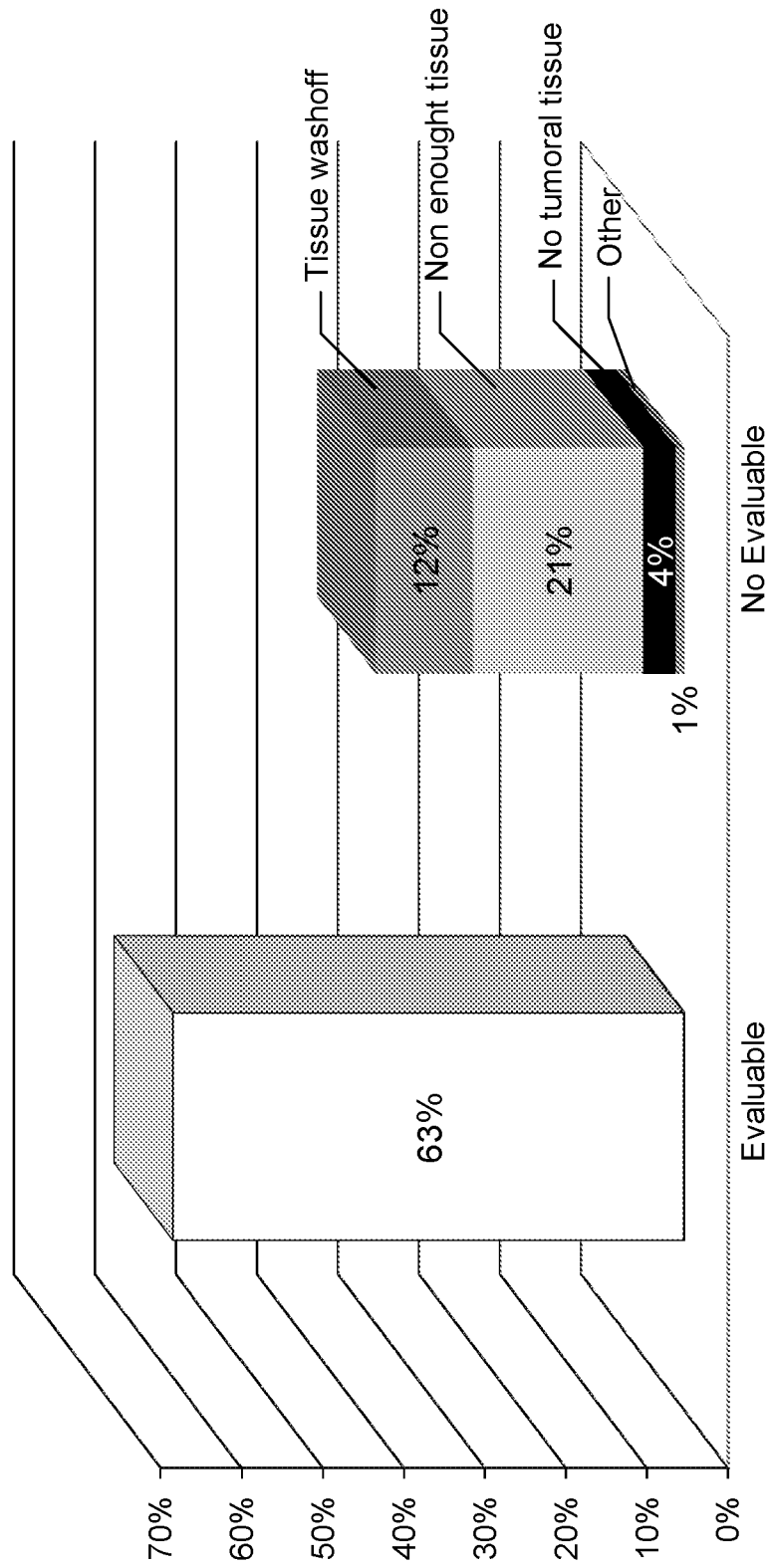
FIG. 3. H&E analysis of AZURE samples. Evaluable and non-evaluable samples are indicated.

An overview of the AZURE clinical trial (Coleman et al N Eng J Med 2011; 365: 1396-1405 and AZURE Current Controlled Trials number, ISRCTN79831382 and ClinicalTrials.gov identifier NCT00072020) study design, whose patients were used to validate MAF, is provided in FIG. 2. MAF was validated in a retrospective analysis of the AZURE trial using patient tumor sample prospectively collected under regulatory compliant conditions. Out of the 3,360 patients recruited, 1,769 donated tumor tissue (52.4%). There were 13 TMAs (tissue micro array) (150 patient samples each) (1,769 patients). There were 4 replicas of each TMA using different tissue cores (6,326 (4× patient)). One TMA had only 1 replica and two TMAs had three replicas. Based on the H&E analysis (hematoxylin and eosin) (FIG. 3) (6,326): 3,978 cores were evaluable (63%) and 2,348 were nonevaluable.

For the FISH assay, there were 2,067 FISH evaluable cores (56%). There were 865 patients (49%) with two FISH evaluable cores (26% of the AZURE patients) and 1,202 patients had a single FISH score (68%). 567 patients were nonevaluable by FISH in any of the 4 replicas (32%).

Figure 4A:
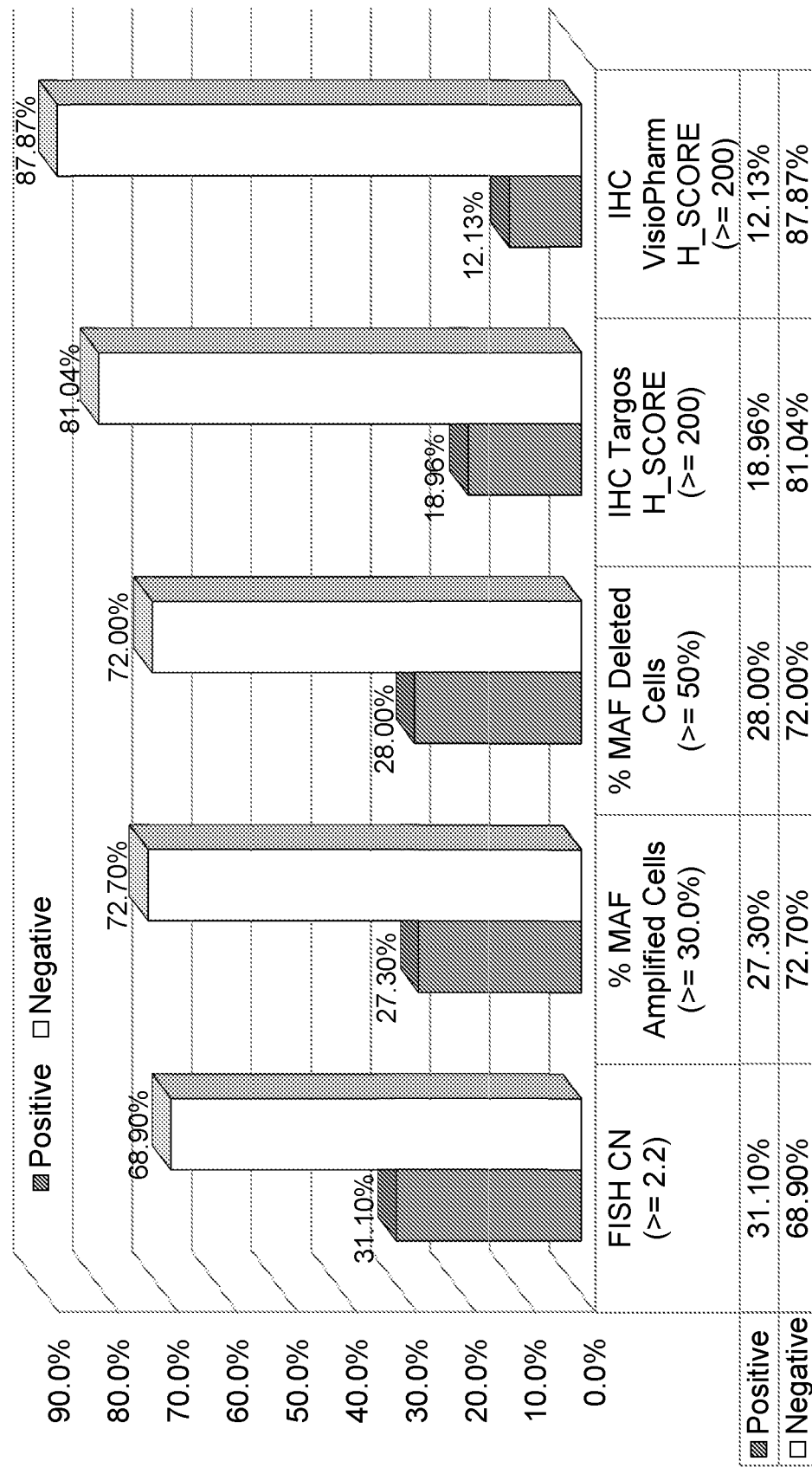
FIGS. 4A-4B. MAF positivity rate.
Figure 4B:
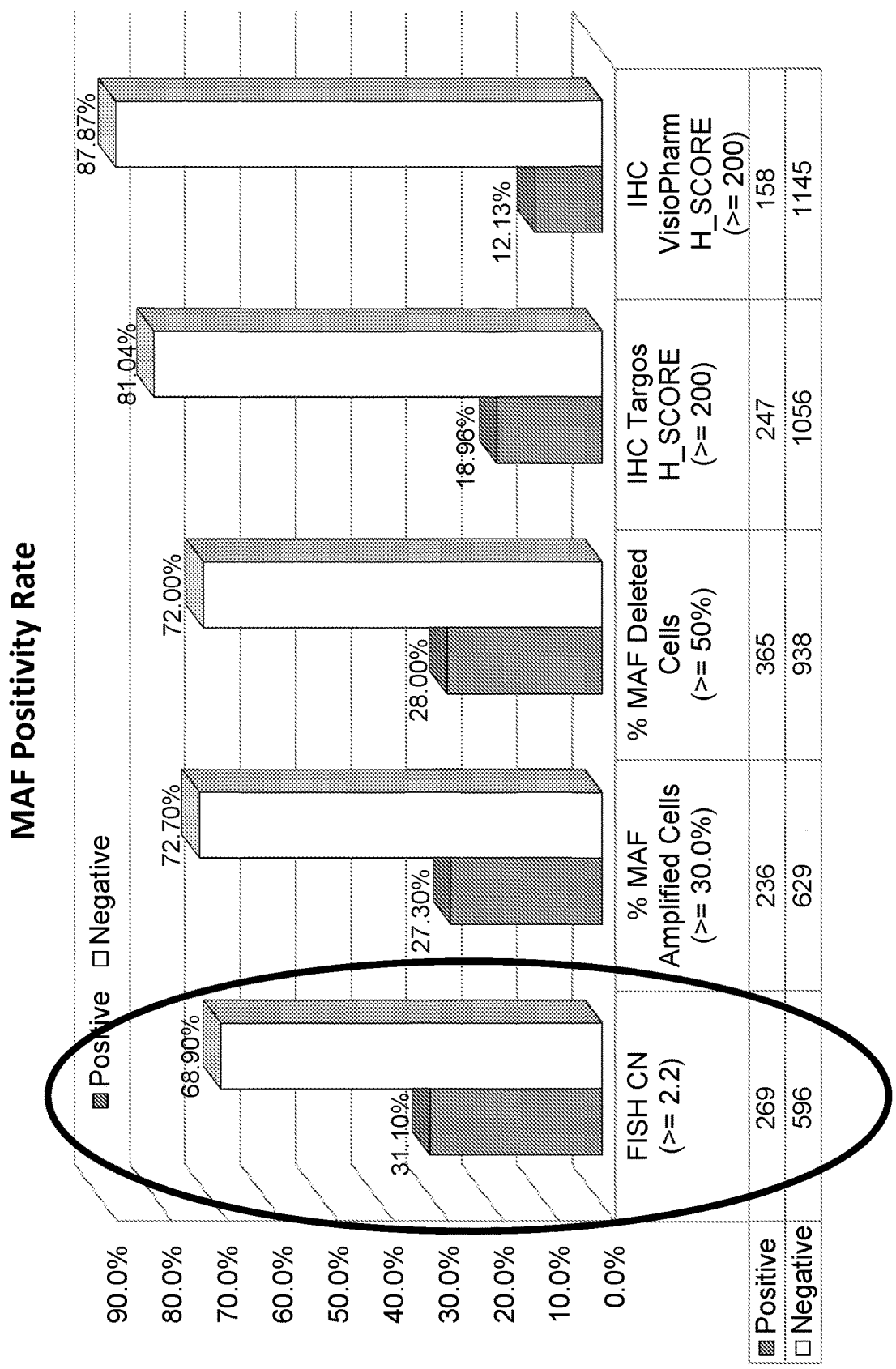

For the IHC assay, a pathologist evaluation and a VisioPharm computer assisted evaluation were performed. For the pathologist evaluation, 2,232 cores were evaluated (59% evaluable for HScore). There were 1,390 patients with an IHC HScore (74%), representing 39% of the total AZURE patients. There were 460 patients that were non-evaluable by IHC in any of the four replicas. In the VisioPharm computer assisted IHC staining evaluation, 1299 IHC patients were evaluated out of 1,309 scored by pathologists for HScore and mean staining per nuclei. The MAF positivity rate can be seen in FIGS. 4A and 4B.

The cut-off optimized FISH data can be seen in FIG. 5 and were calculated as described in Vipery et al JCO 2014 DOI: 10.1200/JCO.2013.53.3604.

With regard to molecular variables, for FISH analysis: MAF copy number: numerical and categorical (+/−cut-off>=2.5) variable; % of nucleic MAF amplified (MAF CN>2):numberical+categorical (cut-off TBD). For the IHC analysis: IHC H-Score: numerical+categorical (cut-off>=200), IHC OD: numerical+categorical (cut-off tBD). The following clinical variables were analyzed: disease-free survival (DFS), invasive disease-free survival (IDFS), overall survival (OS), first recurrence in bone, bone recurrence at any time, time to first DFS event in bone, time to first DFS event not in bone, response to zoledronic acid treatment.

In analyzing the MAF FISH prognostic value, the patients from the control and treatment arms were pooled for the initial analysis. Optimized cut-offs for each variable to be analyzed were used when indicated. Death as a competing event was used in time to bone metastasis, anytime. The following clinical variables were analyzed: time to bone metastasis (anytime), time to bone metastasis (as first event), IDFS (including ipsilateral invasive breast tumor recurrence, regional invasive breast cancer recurrence, metastatic disease-breast cancer, death attributable to any cause, including breast cancer, contralateral invasive breast cancer, second primary non-breast invasive cancer), and overall survival.

Figure 6:
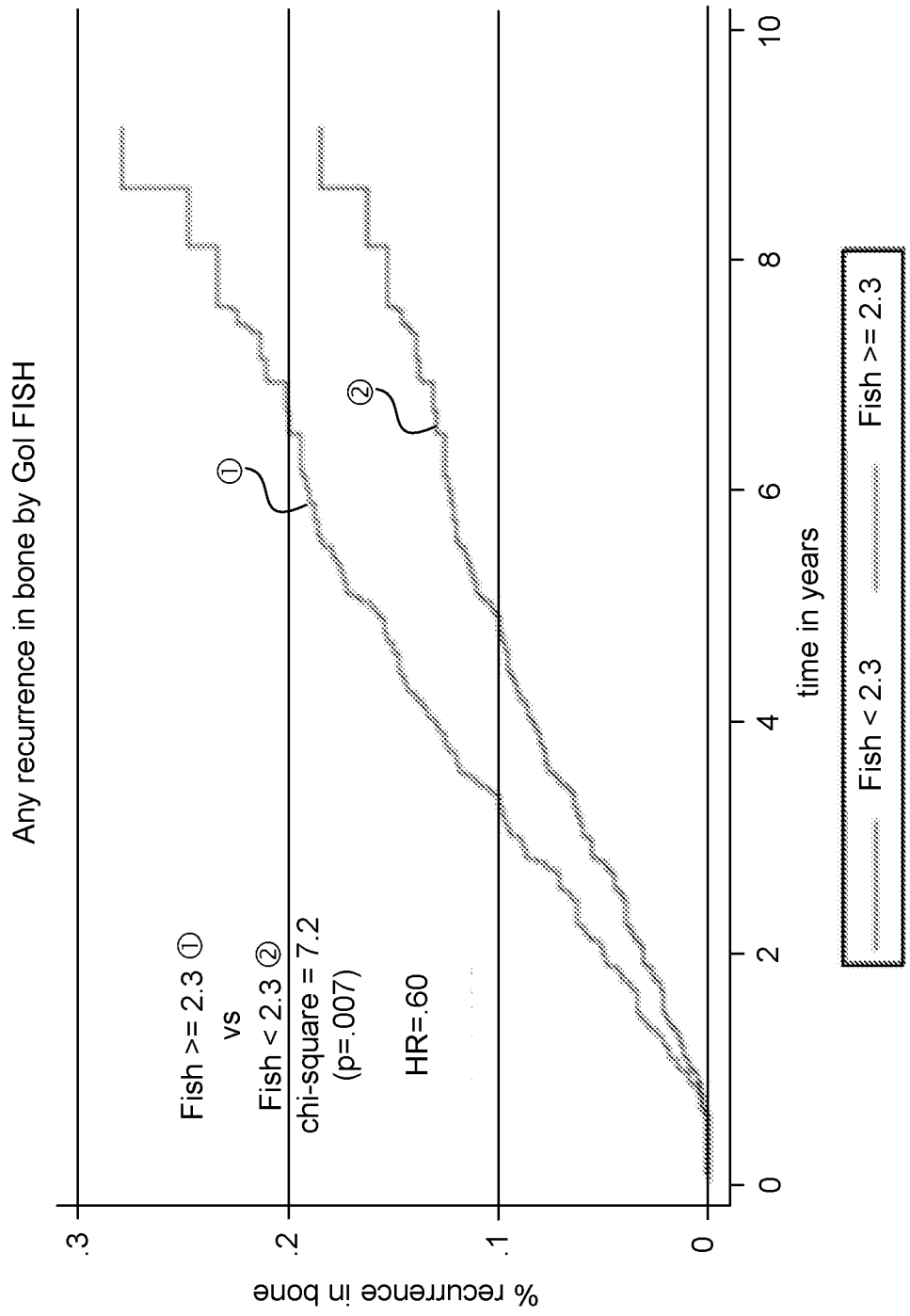
FIG. 6. Risk of bone recurrence based on MAF FISH value.
Figure 7:
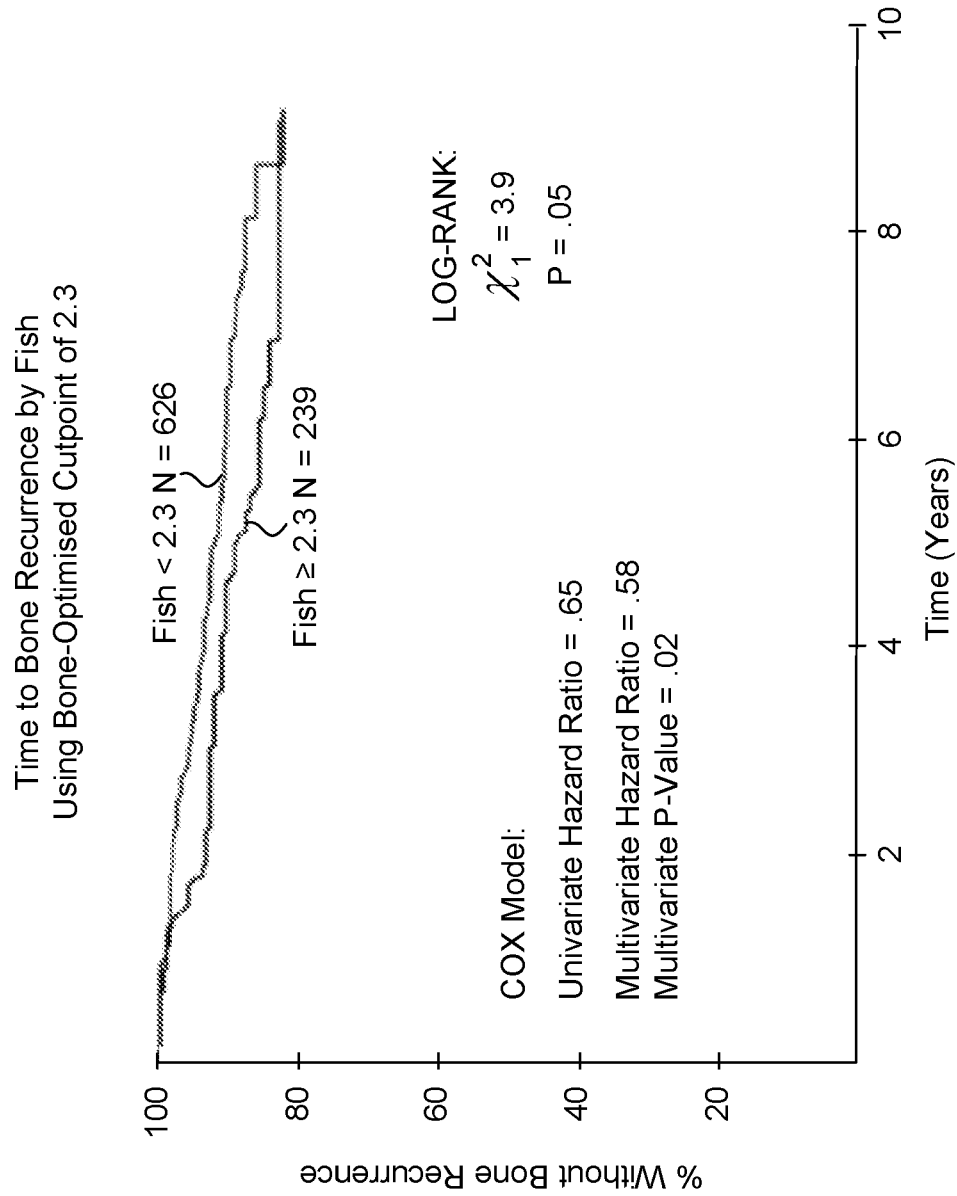
FIG. 7. Time to bone recurrence by MAF FISH value using a bone-optimized cutoff of 2.3.
Figure 8:
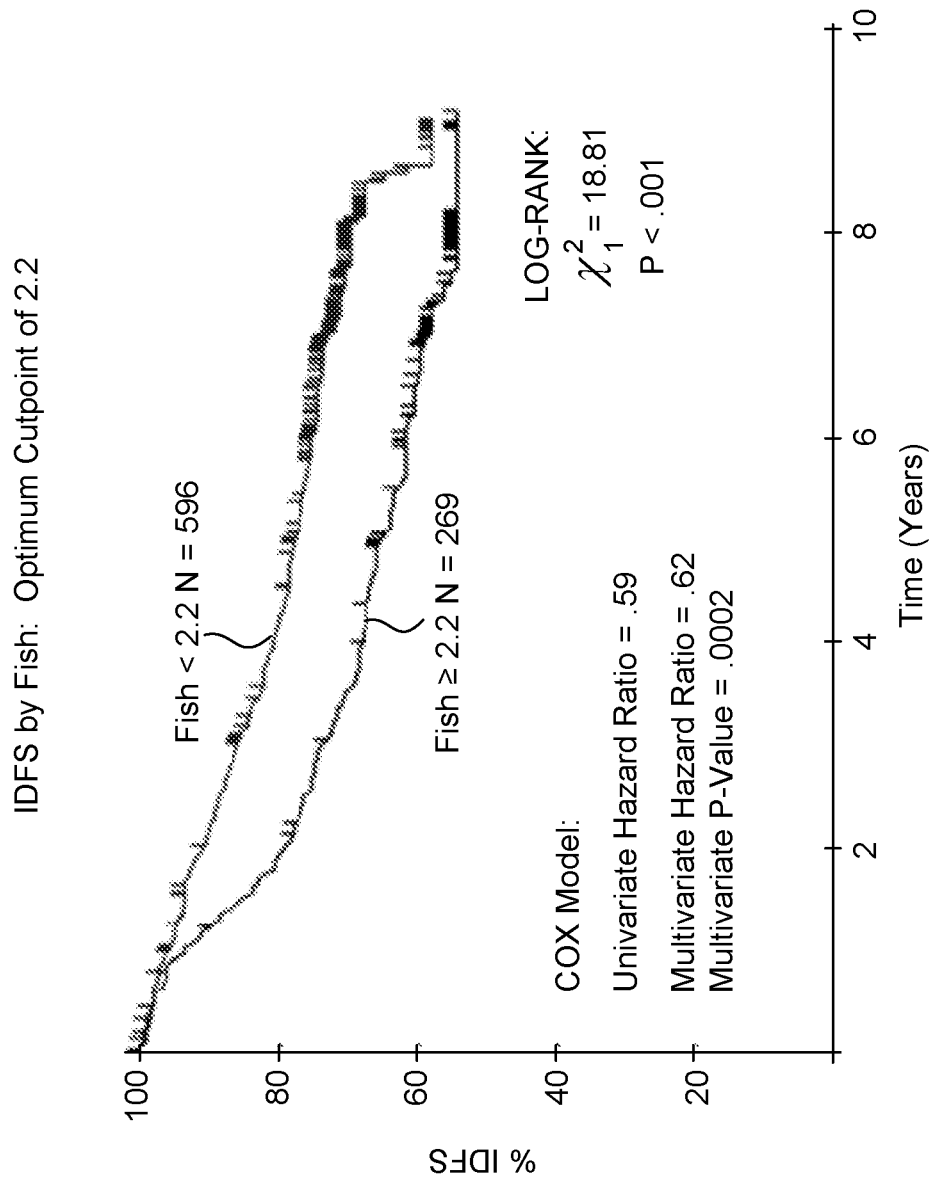
FIG. 8. Percent IDFS by FISH. An optimum cutoff of 2.2 was used.
Figure 9:
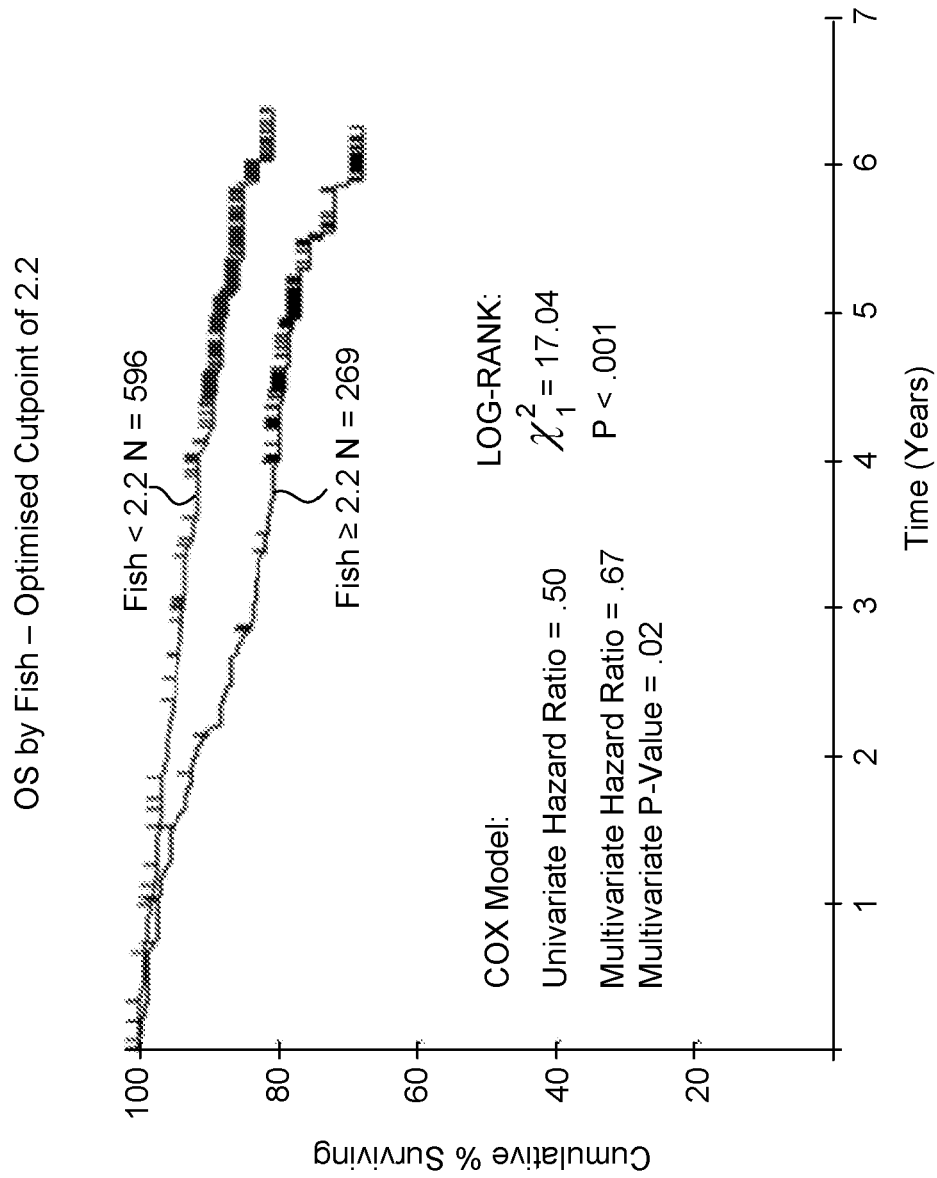
FIG. 9. Overall survival by FISH. An optimum cutoff of 2.2 was used.

FIG. 6 shows that the risk for of bone metastasis was 40% higher in MAF FISH positive patients (>=2.3)(p=0.007) when all patients are analyzed (death as a competing event is used in time to bone metastasis (anytime)). FIG. 7 shows that there was a 42% higher risk for bone as the first metastasis site in MAF FISH positive patients (>=2.3) (p=0.02, multivariate analysis). As seen in FIG. 8, the risk for IDFS was 38% higher in MAF FISH positive patients (>=2.2) (p=0.0002, multivariate analysis) (there is a very early separation by two years then the curves parallel). FIG. 9 shows that overall survival was 33% lower in MAF FISH positive patients (>=2.2) (p=0.02, multivariate analysis) (there is an early separation by three years for the overall survival).

Figure 10:
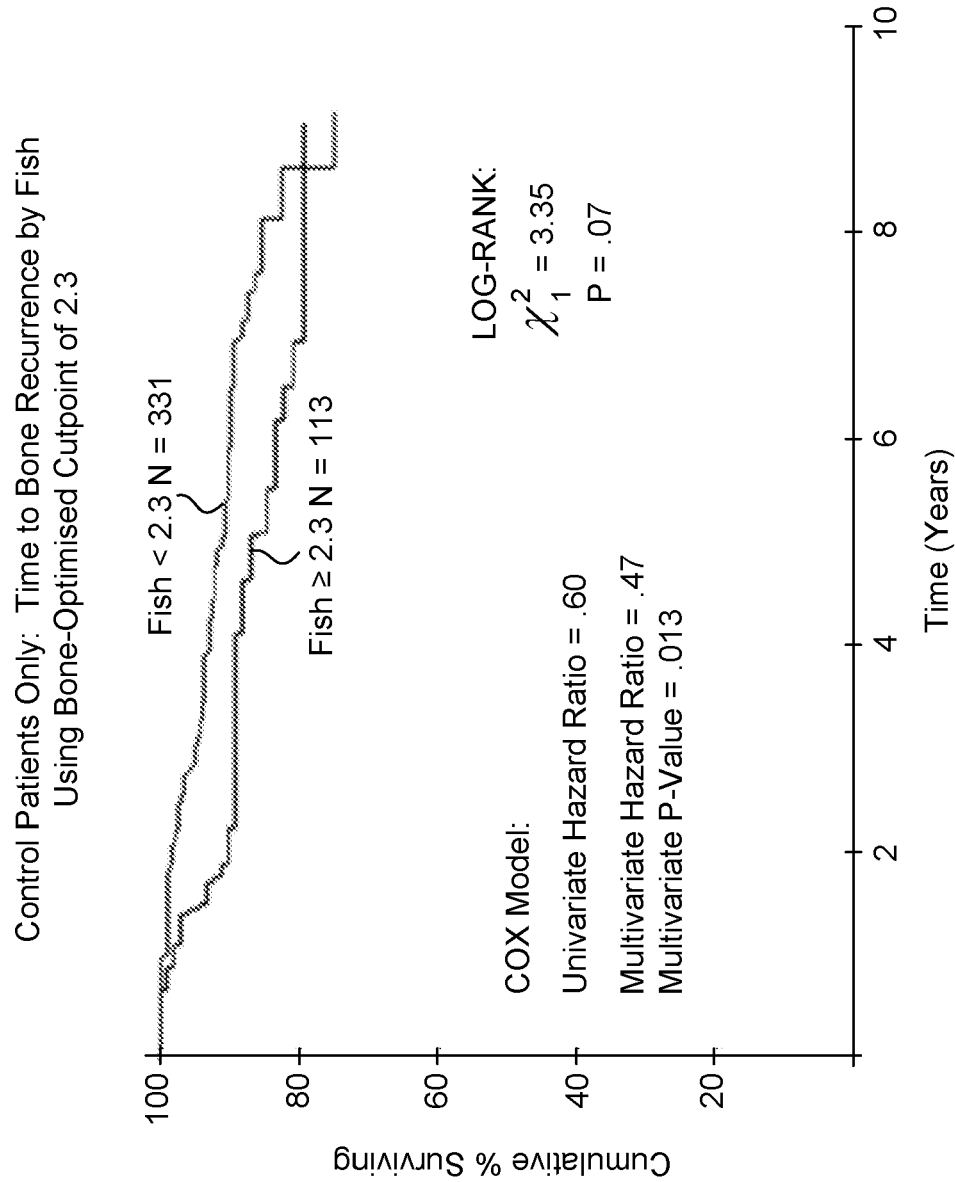
FIG. 10. Time to bone recurrence by FISH in AZURE control patients only. A bone-optimized cutoff of 2.3 was used.

As seen in FIG. 10, there was a shorter time to bone as the first recurrence in MAF FISH positive patients (>=2.3) of the control arm, with a significant difference in the multivariate analysis (HR=0.47, p=0.013).

Figure 11:
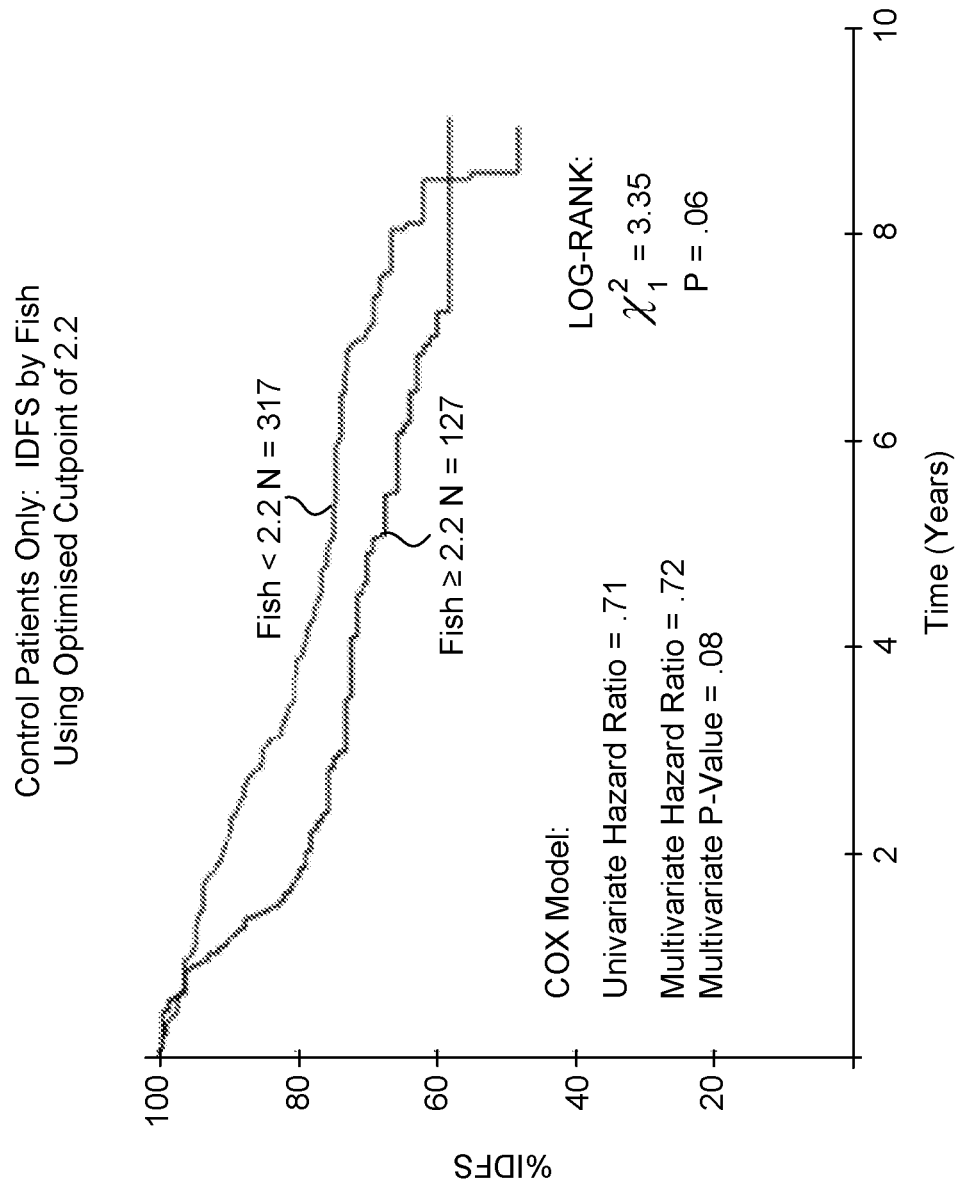
FIG. 11. IDFS by FISH in AZURE control patients only. An optimized cutoff of 2.2 was used.
Figure 12:
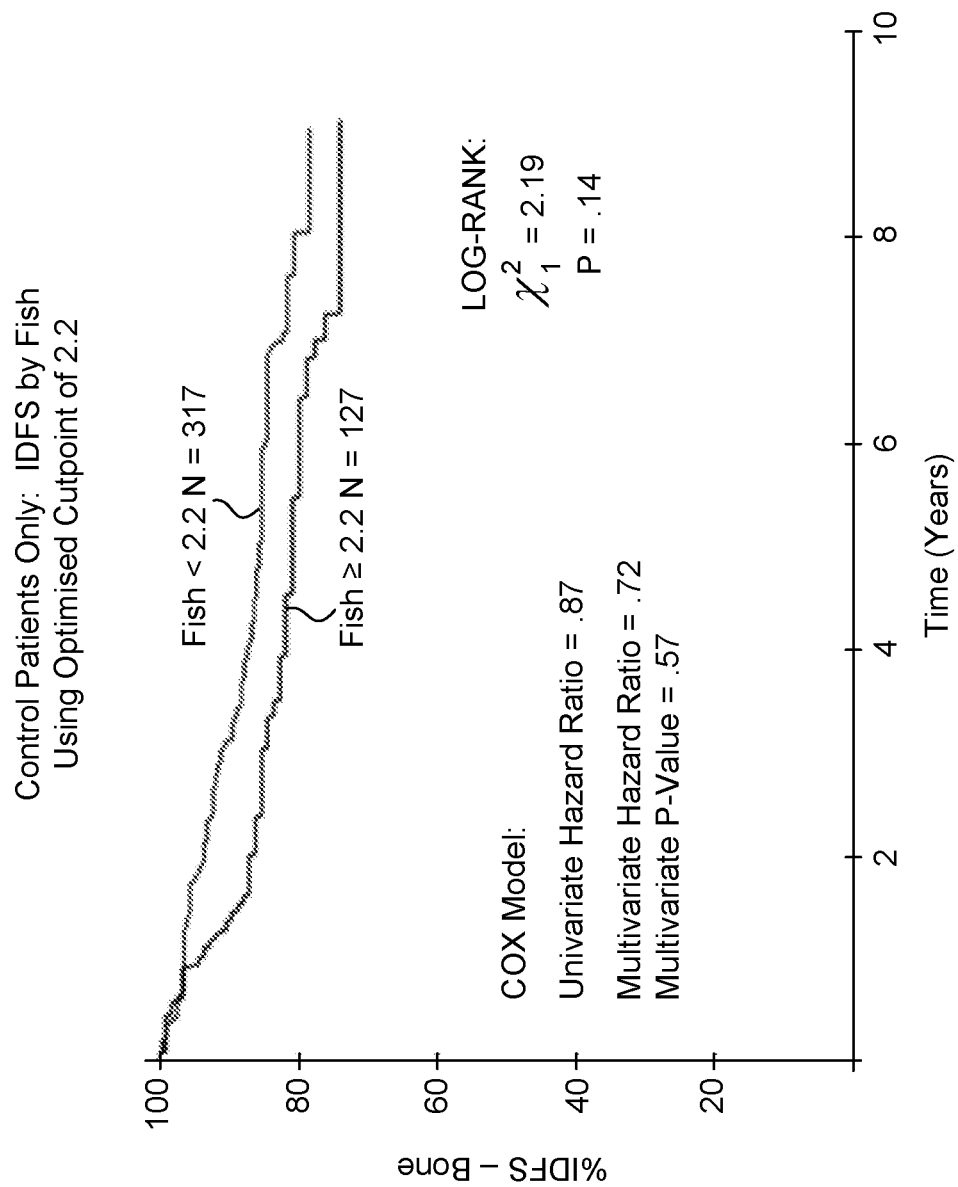
FIG. 12. Time to IDFS (excluding bone recurrence) by FISH in AZURE control patients only. An optimized cutoff of 2.2 was used.

As seen in FIG. 11, there was a trend to a shorter time to recurrence in untreated MAF positive patients (>=2.2) (HR=0.72, p=0.08, multivariate analysis) compared with untreated MAF not positive patients. FIG. 12 shows the time to IDFS (excluding bone recurrence) by FISH in AZURE control patients only. An optimized cutoff of 2.2 was used.

In summary, the predefined cut off to stratify patients according to their MAF FISH level was very close to the optimized computer based defined cutoffs. The threshold effect allows for the delineation of clear groups for appropriate (related) treatment (or avoidance of treatment). Based on the prognosis of the MAF FISH positive patients of the control arm, we saw a shorter time to bone as the first metastasis (HR=0.53, multivariate p=0.03) and a trend to a shorter time to recurrence (invasive disease) (HR=0.72, p=0.08).

Example 2: Evaluation of the Zoledronic Acid Treatment Effect According to MAF FISH Stratification The control and zoledronic acid treatment arms from the AZURE study described in Example 1 were evaluated to determine the effect of zoledronic acid treatment on MAF-stratified patients.

Figure 13:
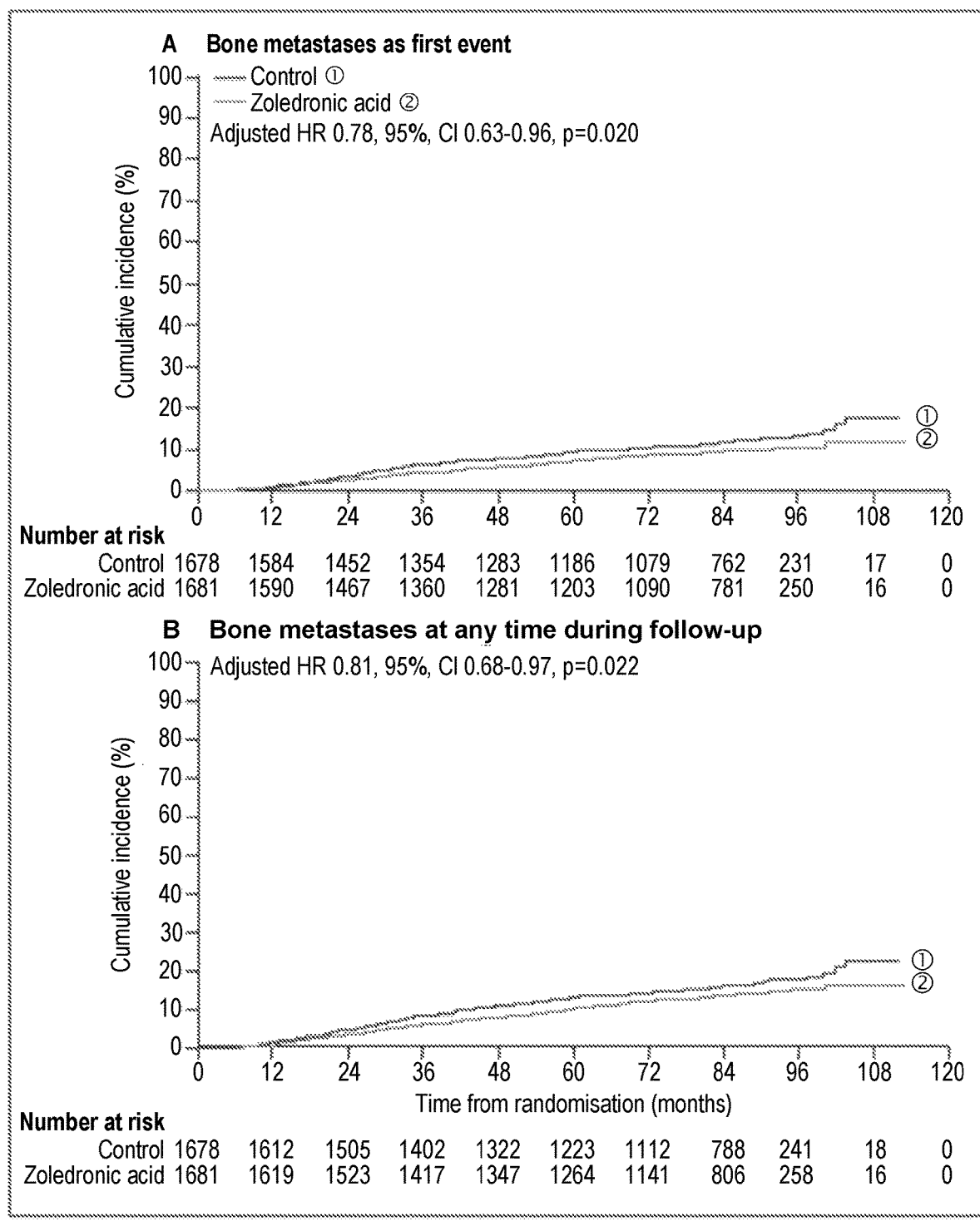
FIGS. 13A-13B. Time to bone metastasis in patients in the control arm and in the zoledronic acid treatment arm. Cumulative incidence of bone metastasis (A) as a first event and (B) at any time during follow-up. Analyses were by intention to treat. HR-hazard ratio.
Figure 14:
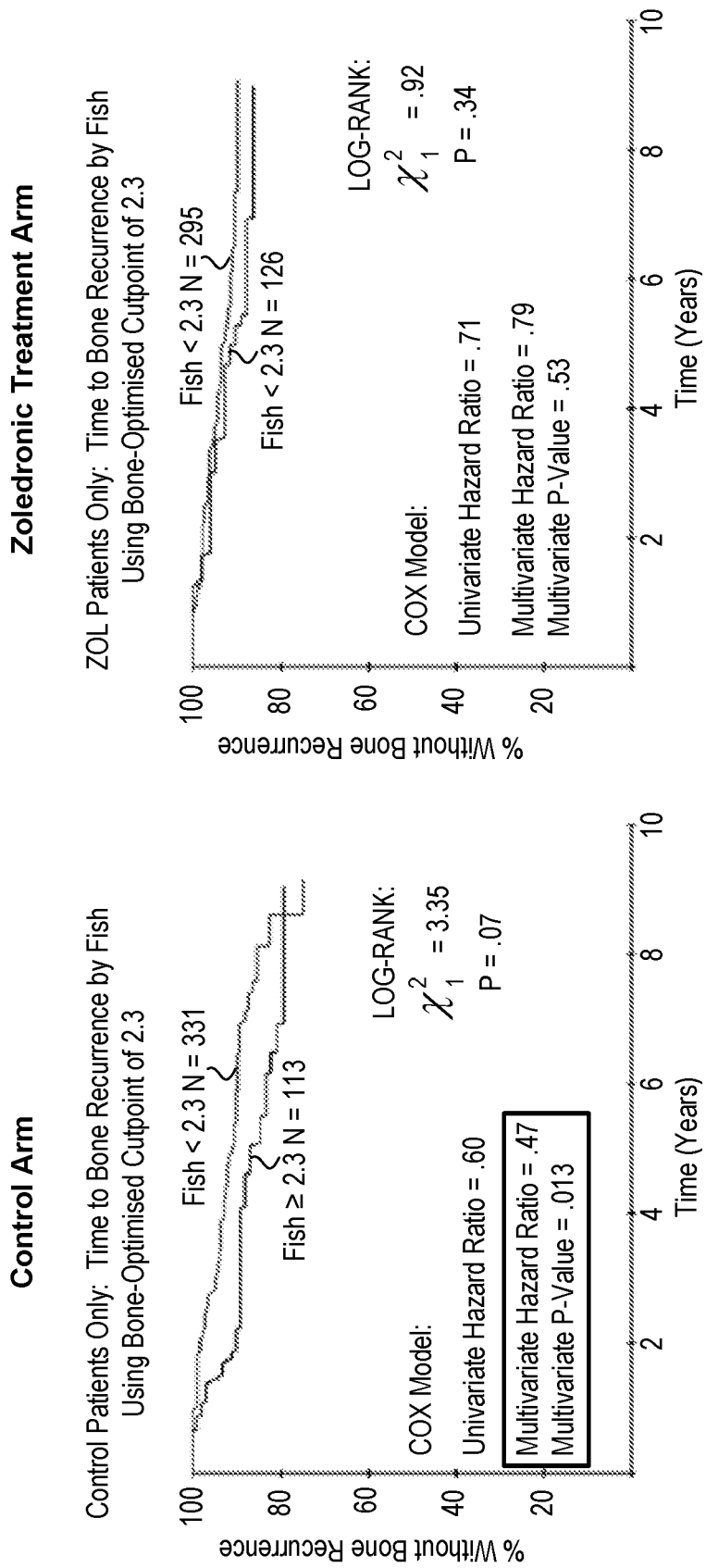
FIG. 14. Evaluation of the time to bone metastasis as a first event in AZURE control patients and zoledronic acid treated patients. A bone-optimized cutoff of 2.3 was used.

FIGS. 13A-13B (Coleman et al., Lancet Oncol 2014; 15: 997-1006, FIG. 3) shows the time to bone metastasis in patients in the control arm and in the zoledronic acid treatment arm of the AZURE trial. FIG. 14 shows an evaluation of the time to bone metastasis as a first event. As can be seen in FIG. 14, there was a shorter time to bone as first recurrence in MAF FISH positive (>=2.3) patients of the control arm, with a significant difference in the multivariate analysis (HR=0.47, p=0.013, multivariate analysis). Zoledronic acid treatment reduced the differences in incidence of bone as first site of recurrence between MAF positive and non-positive patients, and there was no significant difference in the risk of bone metastasis at any time in MAF positive compared to MAF non-positive patients treated with zoledronic acid.

Figure 15:
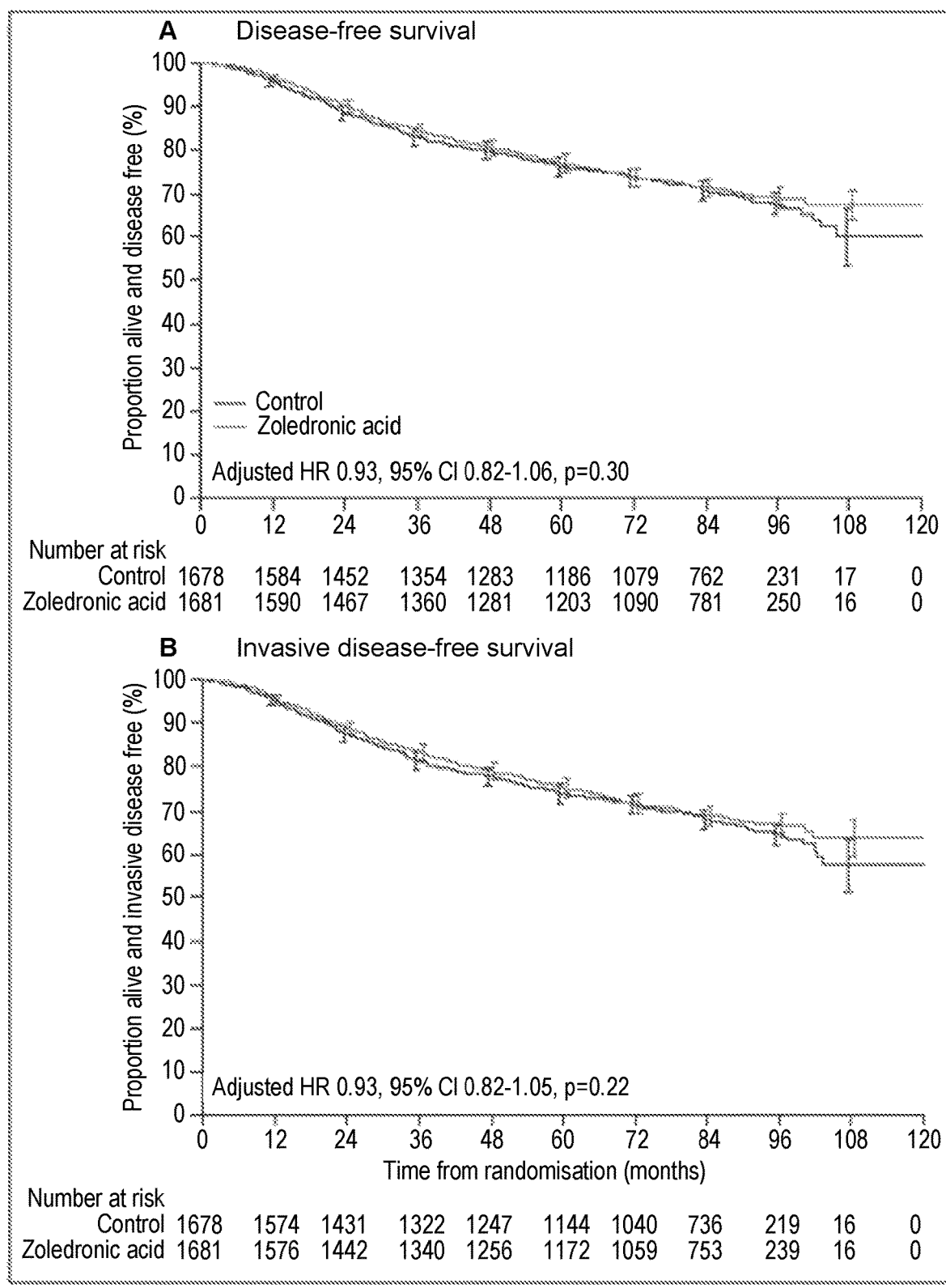
FIGS. 15A-15B. Disease (DFS) and invasive disease (IDFS) free survival between the control arm and the zoledronic acid treated patients. Kaplan-Meier curves of (A) disease-free-survival and (B) invasive disease-free survival. Analyses were by intention to treat. HR=hazard ratio.

FIG. 15 (Coleman et al Lancet Oncol 2014; 15: 997-1006, FIG. 2) shows an analysis of disease (DFS) and invasive disease (IDFS) free survival between the control arm and the zoledronic acid treated patients in the AZURE trial.

Figure 16:
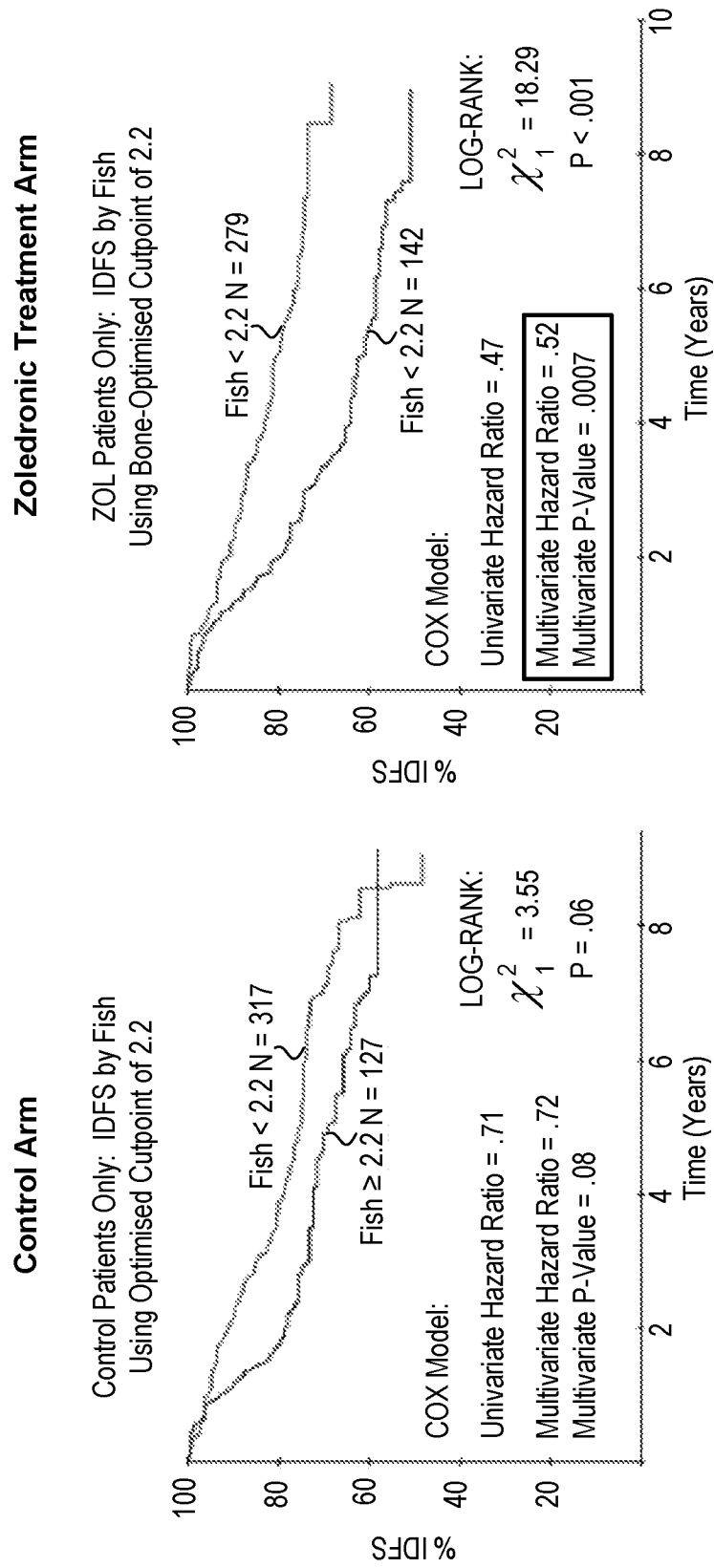
FIG. 16. Time to distant recurrence between the control arm and the zoledronic acid treated patients.

FIG. 16 shows the time to distant recurrence between the control arm and the zoledronic acid treated patients. There was a trend to a shorter time to distant recurrence in untreated MAF positive patients (>=2.2) (HR=0.72, p=0.08, multivariate analysis). There was a significantly shorter time to recurrence (invasive disease) in MAF positive patients in the zoledronic acid treatment arm (HR=0.52, p<0.001, multivariate analysis). Treatment with zoledronic acid worsened IDFS compared to untreated MAF positive patients.

Figure 17:
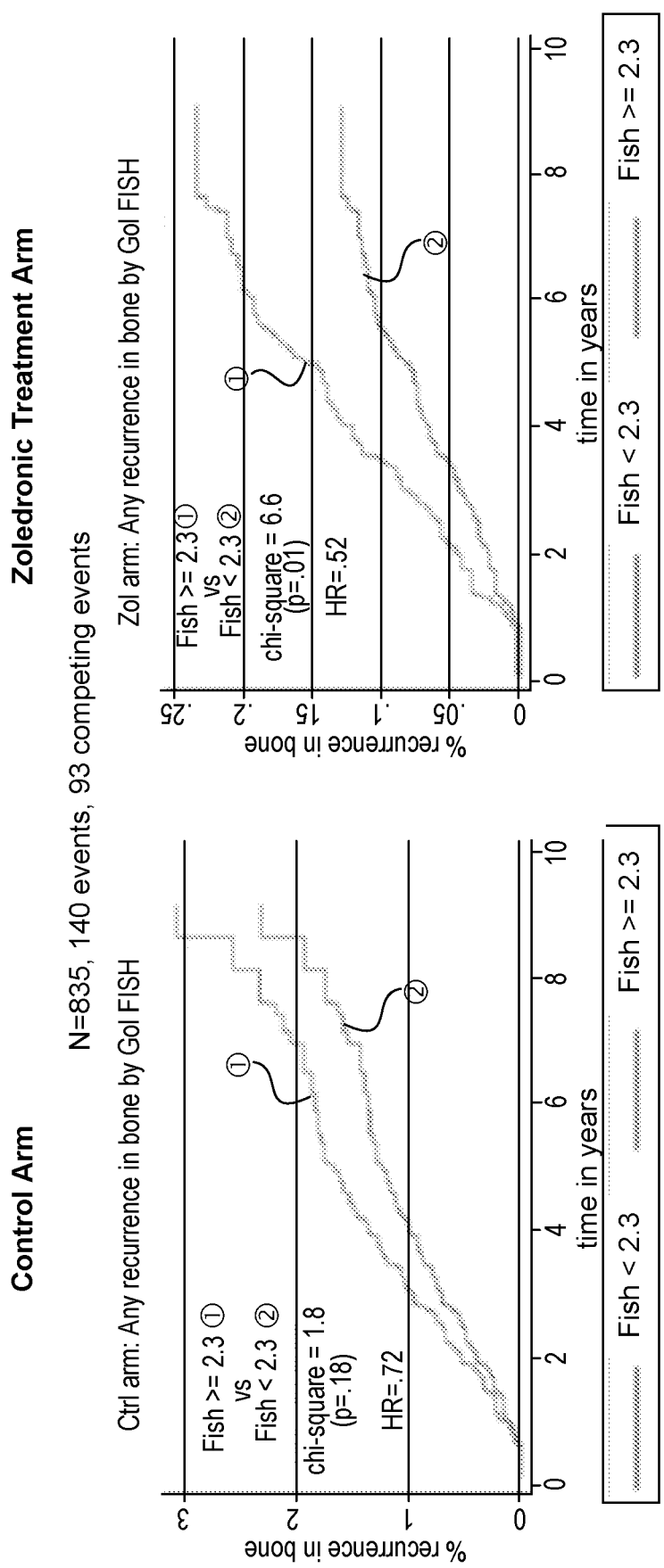
FIG. 17. Time to a bone metastatic event (anytime) according to treatment. Death as a competing event is used in time to bone metastasis (anytime).

FIG. 17 shows the time to a bone metastatic event (anytime) according to treatment. Death as a competing event is used in time to bone metastasis (anytime). There was a non-significant increased risk of bone metastasis in MAF FISH positive patients (>=2.3) of the control arm (HR=0.72, p=0.18). Zoledronic acid treatment significantly reduced the risk of bone metastasis at any time in MAF FISH not positive patients (<2.3) (HR=0.52, p=0.01) compared to MAF FISH positive patients.

Figure 18:
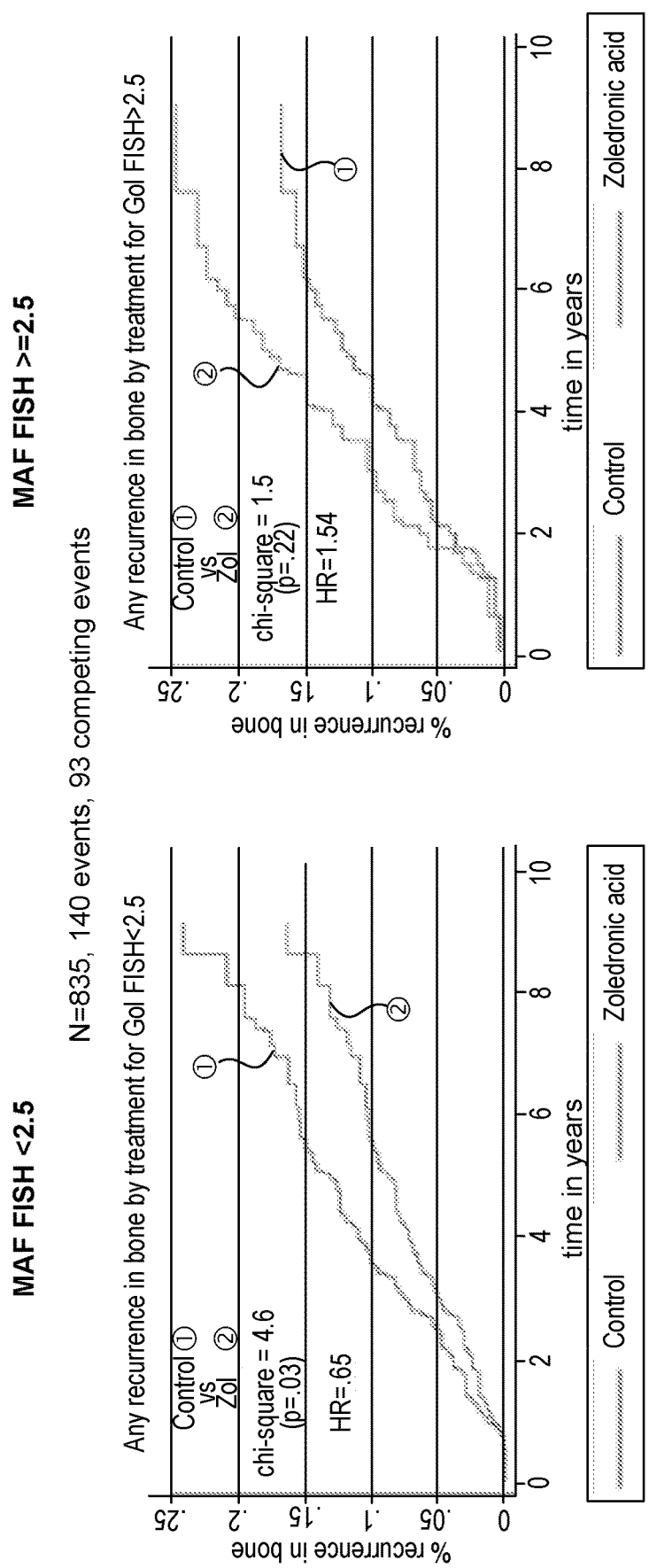
FIG. 18. Time to a bone metastatic event (anytime) according to MAF copy number (according to pre-specified MAF cut off of 2.5).

FIG. 18 shows the time to a bone metastatic event (anytime) according to MAF copy number (according to pre-specified MAF cut off of 2.5). Death as a competing event is used in time to bone metastasis (anytime). Zoledronic acid treatment significantly reduced the risk of bone metastasis in MAF FISH not positive patients (HR=0.65, p=0.03). Zoledronic acid treatment showed a trend to an increased risk of bone metastasis in MAF positive patients. The difference was non-significant (HR=1.54, p=0.22).

Figure 19:
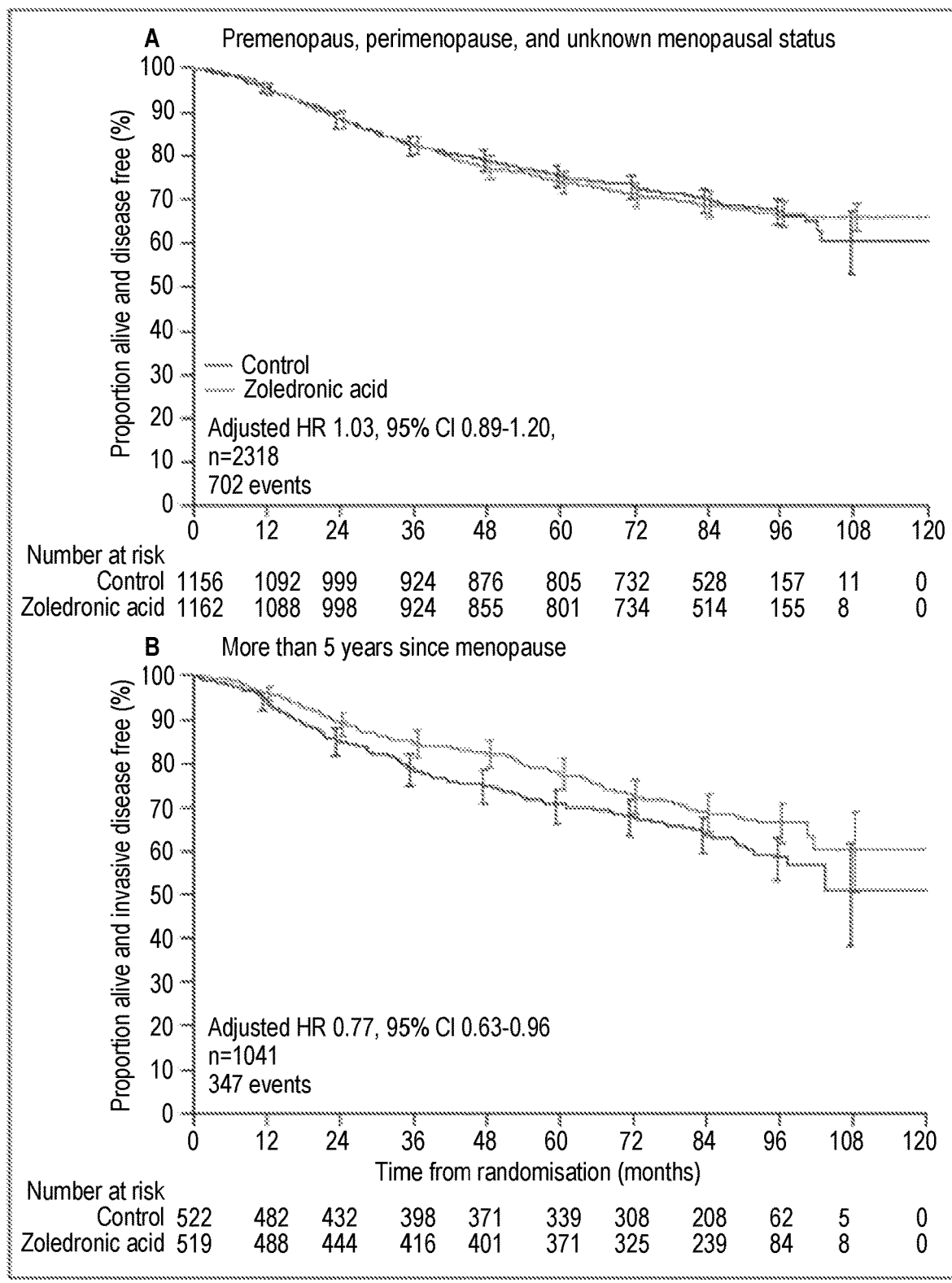
FIGS. 19A-19B. IDFS by menopausal status of the AZURE trial. Kaplan-Meir curve of invasive disease-free survival by menopausal status. (A) premenopause, perimenopause, and unknown menopausal status and (B) more than 5 years since menopause. Test of heterogeneity by menopausal status $\chi^2_1$ 4.71; p=0.03.

FIG. 19 shows the IDFS by menopausal status of the AZURE trial when patients are not stratified according to MAF (Coleman et al Lancet Oncol 2014; 15: 997-1006, FIG. 5).

Figure 20:
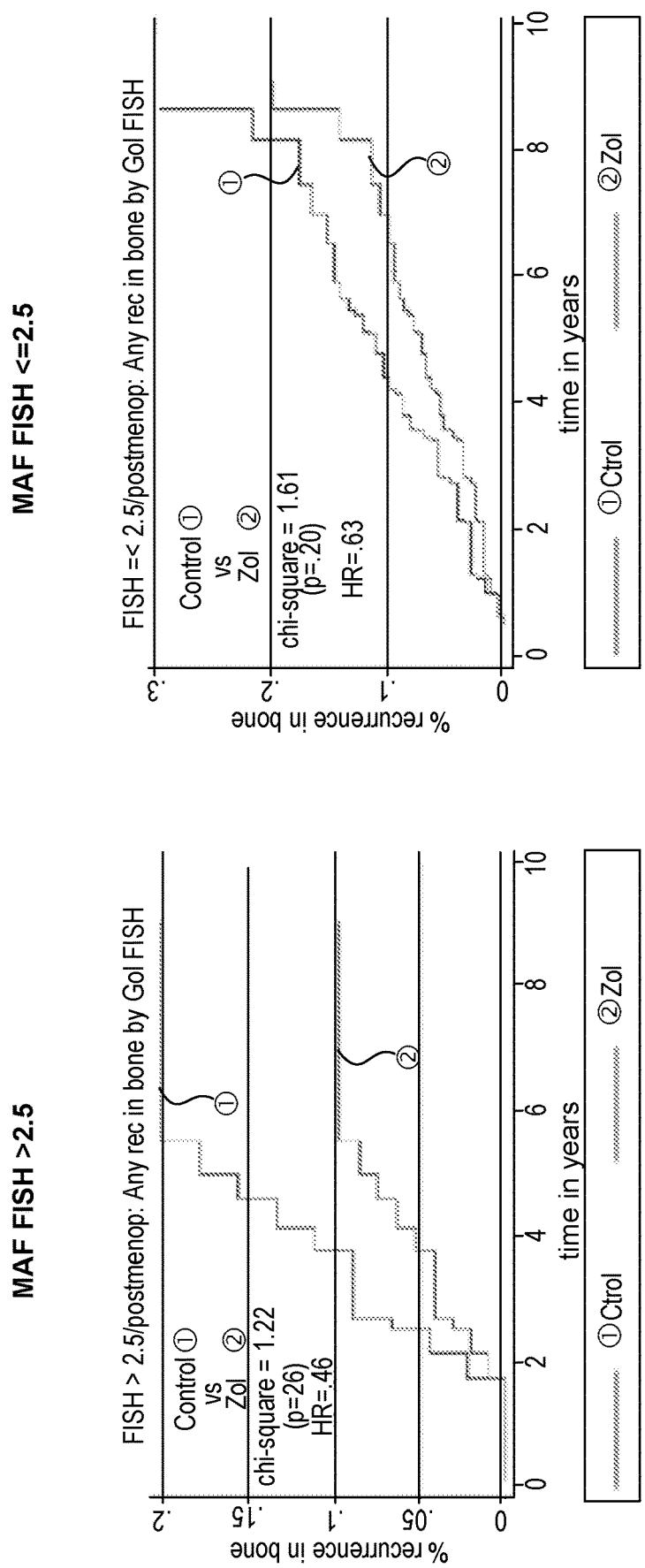
FIG. 20. Time to a bone metastatic event (anytime) according to MAF copy number (data according to a pre-specified cut off of 2.5) in post menopausal patients.

FIG. 20 shows the time to a bone metastatic event (anytime) using death as a competing event according to MAF copy number (data according to a pre-specified cut off of 2.5) in postmenopausal patients. The treatment outcome in MAF positive postmenopausal patients (>2.5) showed a trend to reduce the number of bone metastasis events (HR=0.46, p=0.26, with a limited number of events). The treatment outcome in MAF non-positive postmenopausal patients treated with zoledronic acid was less effective than in MAF positive postmenopausal patients (HR=0.63 vs HR=0.46, with a limited number of events) suggesting a clear benefit of zoledronic acid treatment to prevent bone metastasis in the MAF positive postmenopausal patients.

Figure 21:
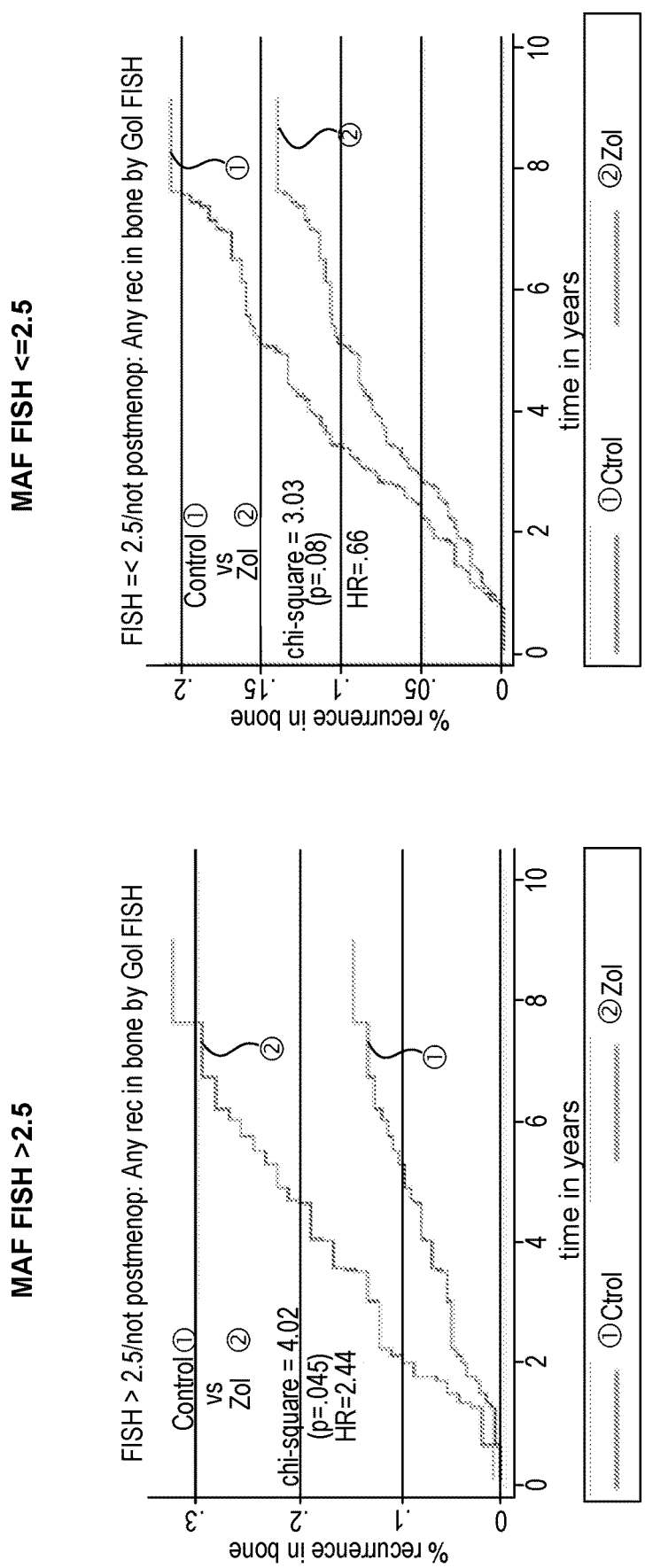
FIG. 21. Time to a bone metastatic event (anytime) according to MAF copy number (data according to a pre-specified cut off of 2.5) in non-post menopausal patients.

FIG. 21 shows the time to a bone metastatic event (anytime) according to MAF copy number (data according to a pre-specified cut off of 2.5) in non-post menopausal patients. There was a significantly worse zoledronic acid treatment outcome in MAF positive non-post-menopausal patients causing an increase in bone metastatic events (HR=2.44, p=0.045). There was a trend to a better outcome with zoledronic acid treatment in MAF non-positive non-post-menopausal patients (HR=0.66, p=0.08).

Figure 22:
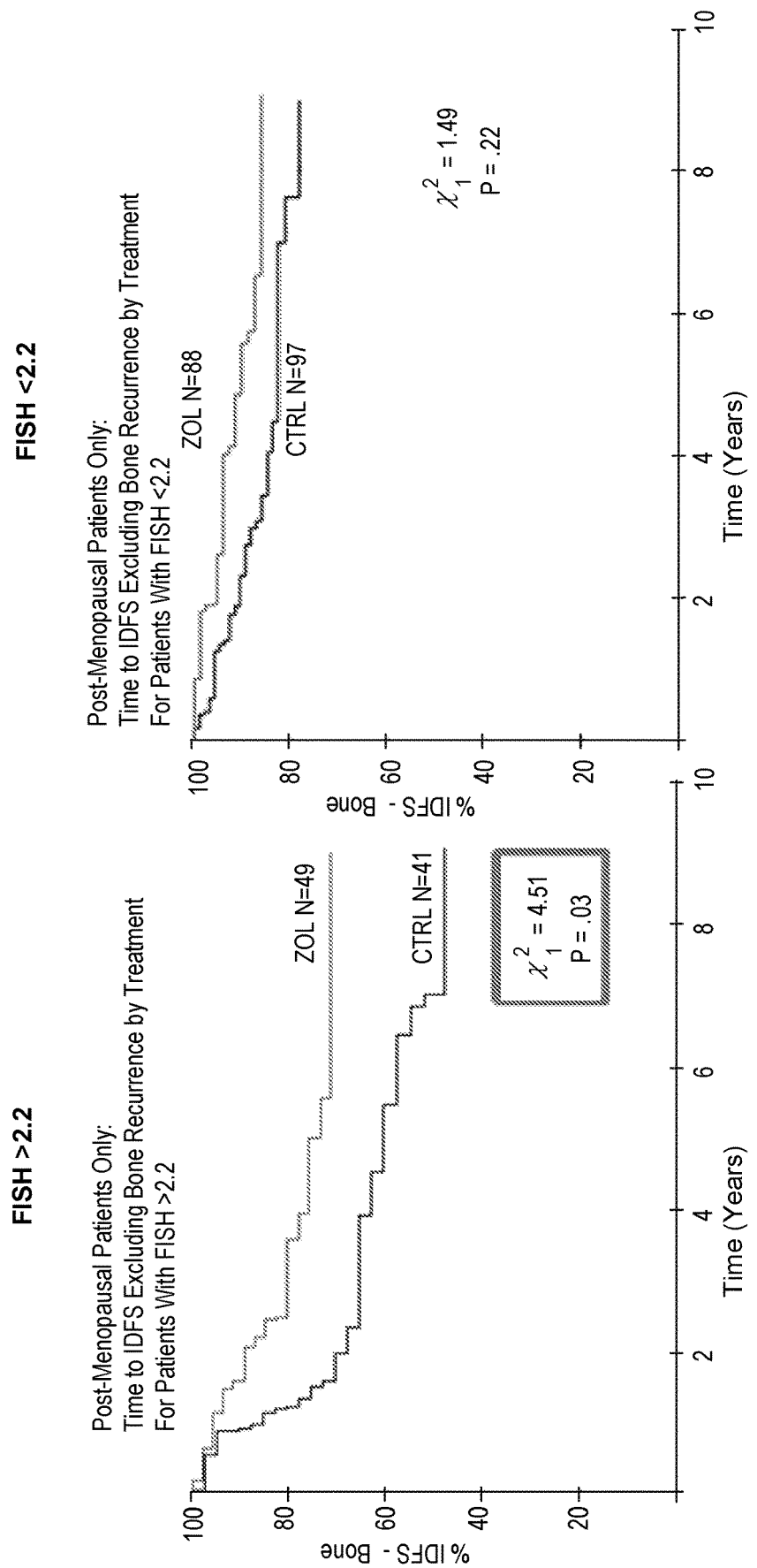
FIG. 22. IDFS of the zoledronic acid treatment arm and the control arm, excluding bone metastasis of post-menopausal women.

FIG. 22 shows the IDFS of the zoledronic acid treatment arm and the control arm, excluding bone metastasis of post-menopausal women. As seen in FIG. 22, the treatment of post-menopausal patients with zoledronic acid significantly improved the IDFS (excluding bone) of MAF FISH positive patients (>=2.2) reducing the number of invasive disease events, and there was no difference in the IDFS (excluding bone) of MAF non-positive patients.

Figure 23:
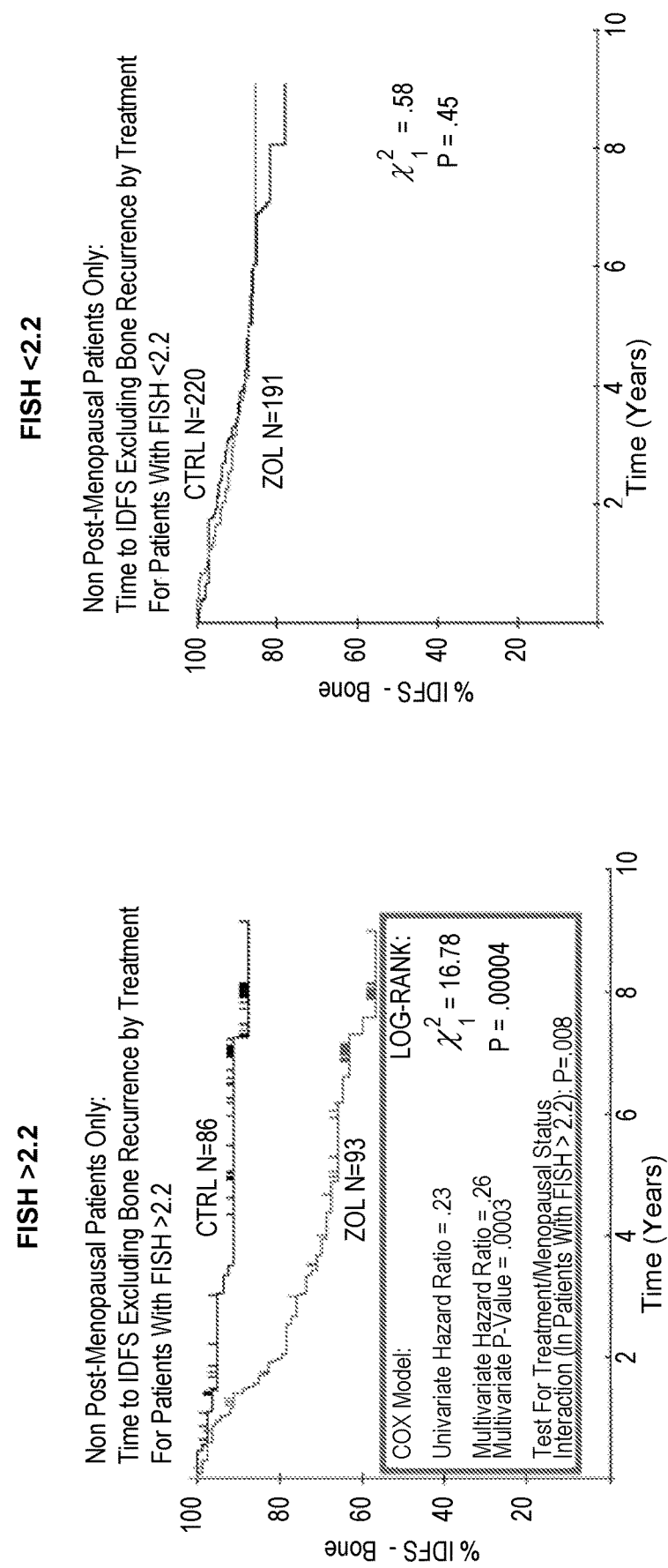
FIG. 23. IDFS of the zoledronic acid treatment arm and the control arm, excluding bone metastasis of non-post-menopausal women.

FIG. 23 shows the IDFS of the zoledronic acid treatment arm and the control arm, excluding bone metastasis of non-post-menopausal women. As seen in FIG. 23, the treatment of non-post menopausal women with zoledronic acid significantly worsens the IDFS (excluding bone) of MAF FISH positive patients (>=2.2), and no difference was seen in the IDFS (excluding bone) of the MAF FISH non-positive patients.

Figure 24:
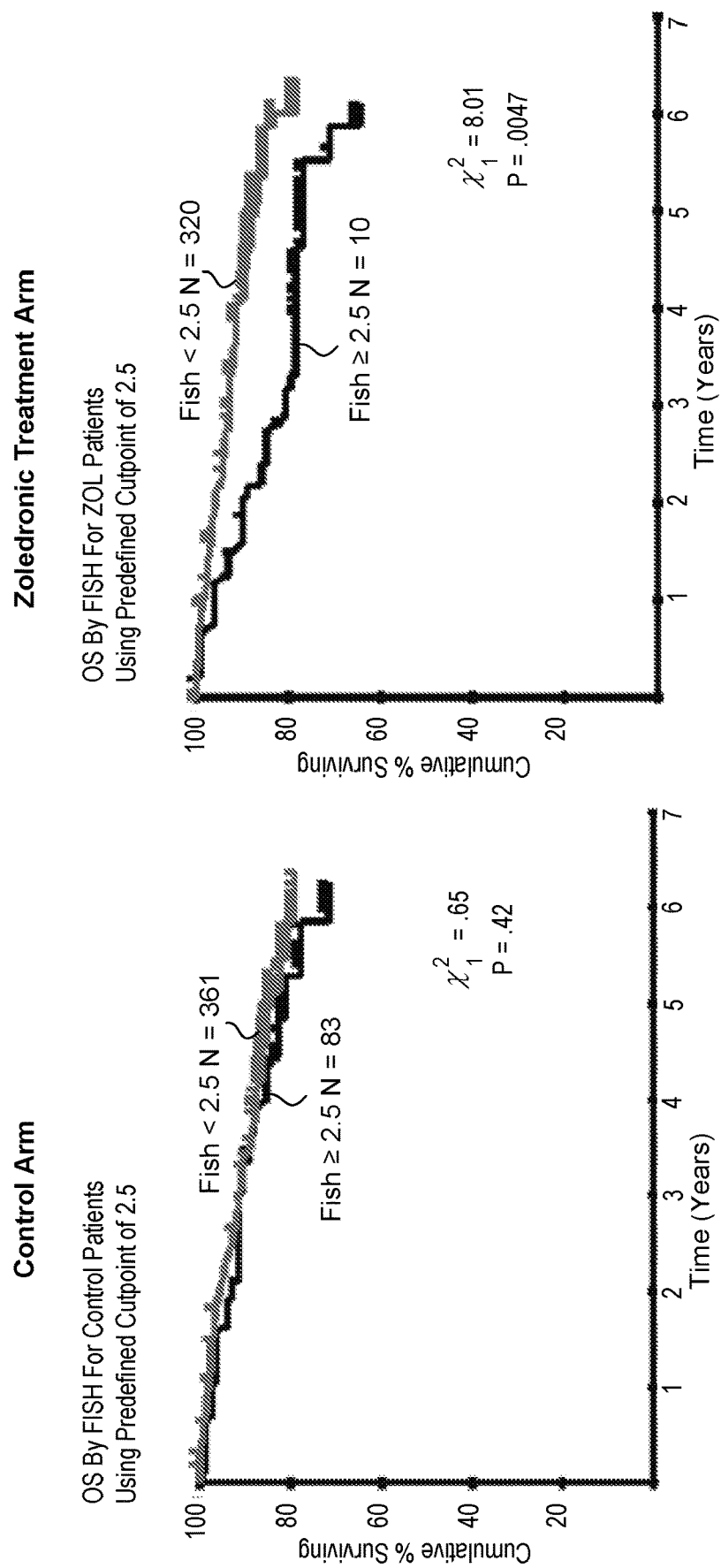
FIG. 24. Overall survival (OS) by treatment arm. Treatment of MAF FISH positive patients with zoledronic acid significantly impacted the OS.

FIG. 24 shows the overall survival (OS) by treatment arm. Treatment of MAF FISH positive patients with zoledronic acid significantly impacted the OS.

Figure 25:
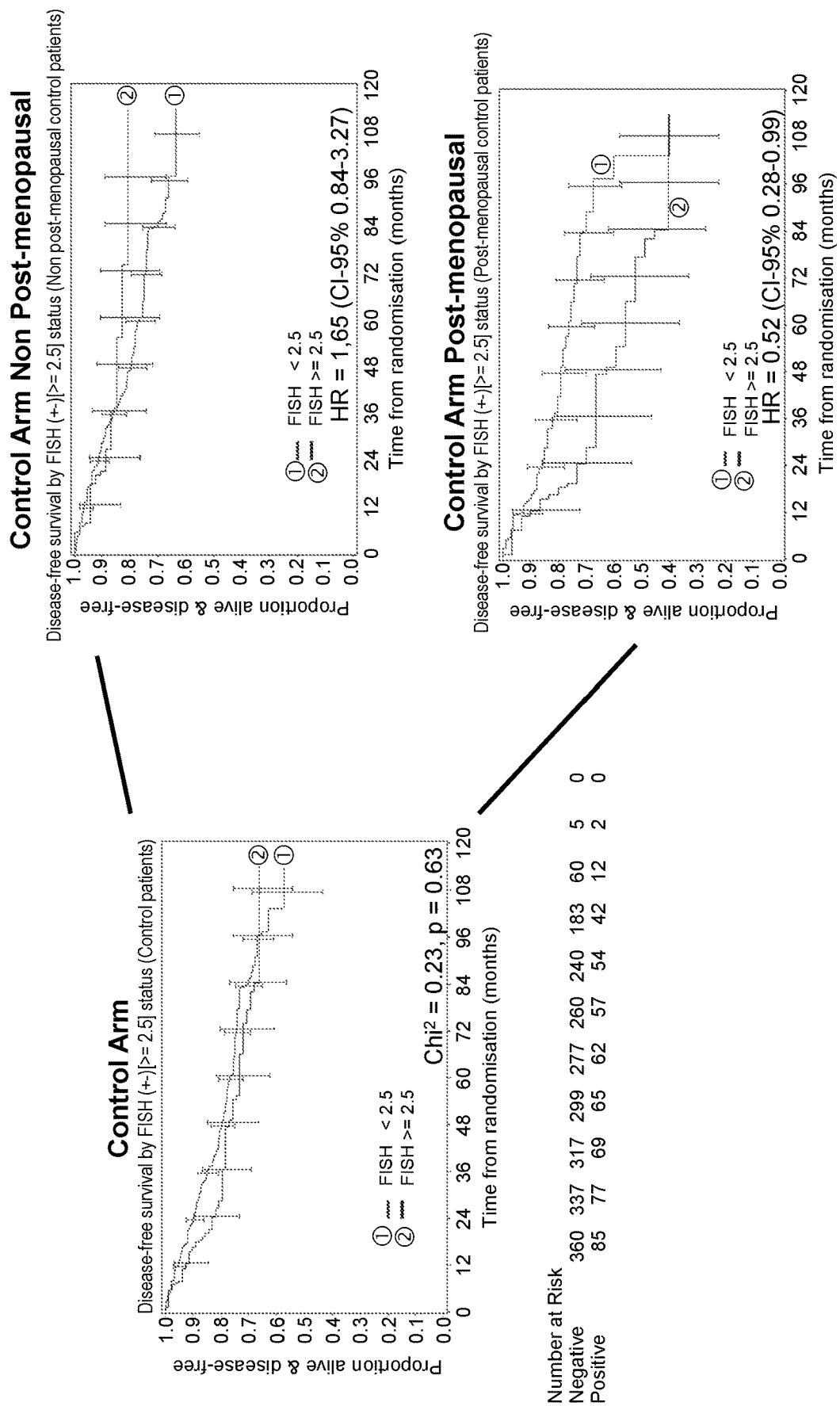
FIG. 25. Prognostic value of MAF FISH for disease free survival (DFS) in the AZURE control arm.
Figure 26:
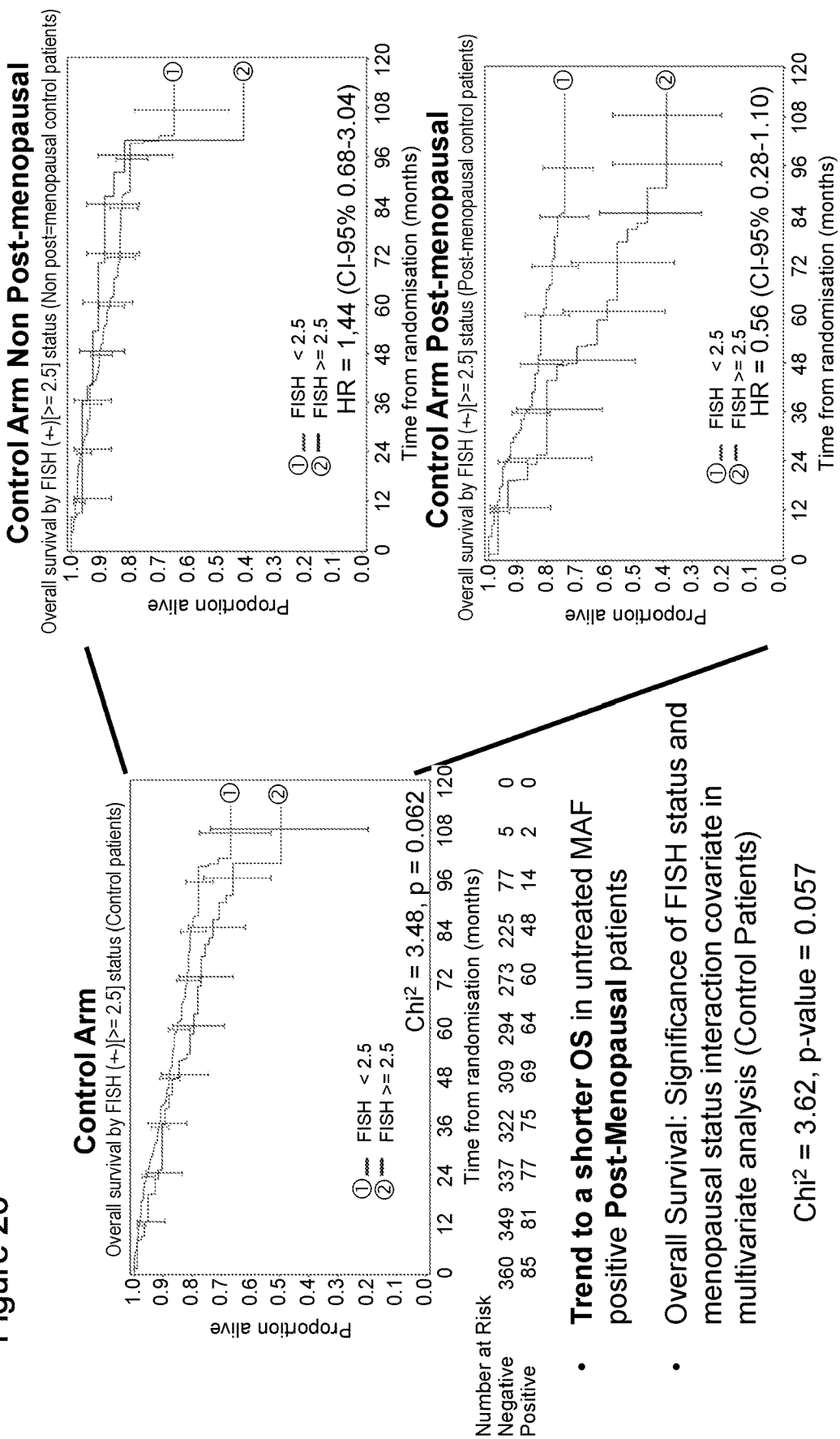
FIG. 26. Prognostic value of MAF FISH for overall survival (OS) in the AZURE control arm.
Figure 27:
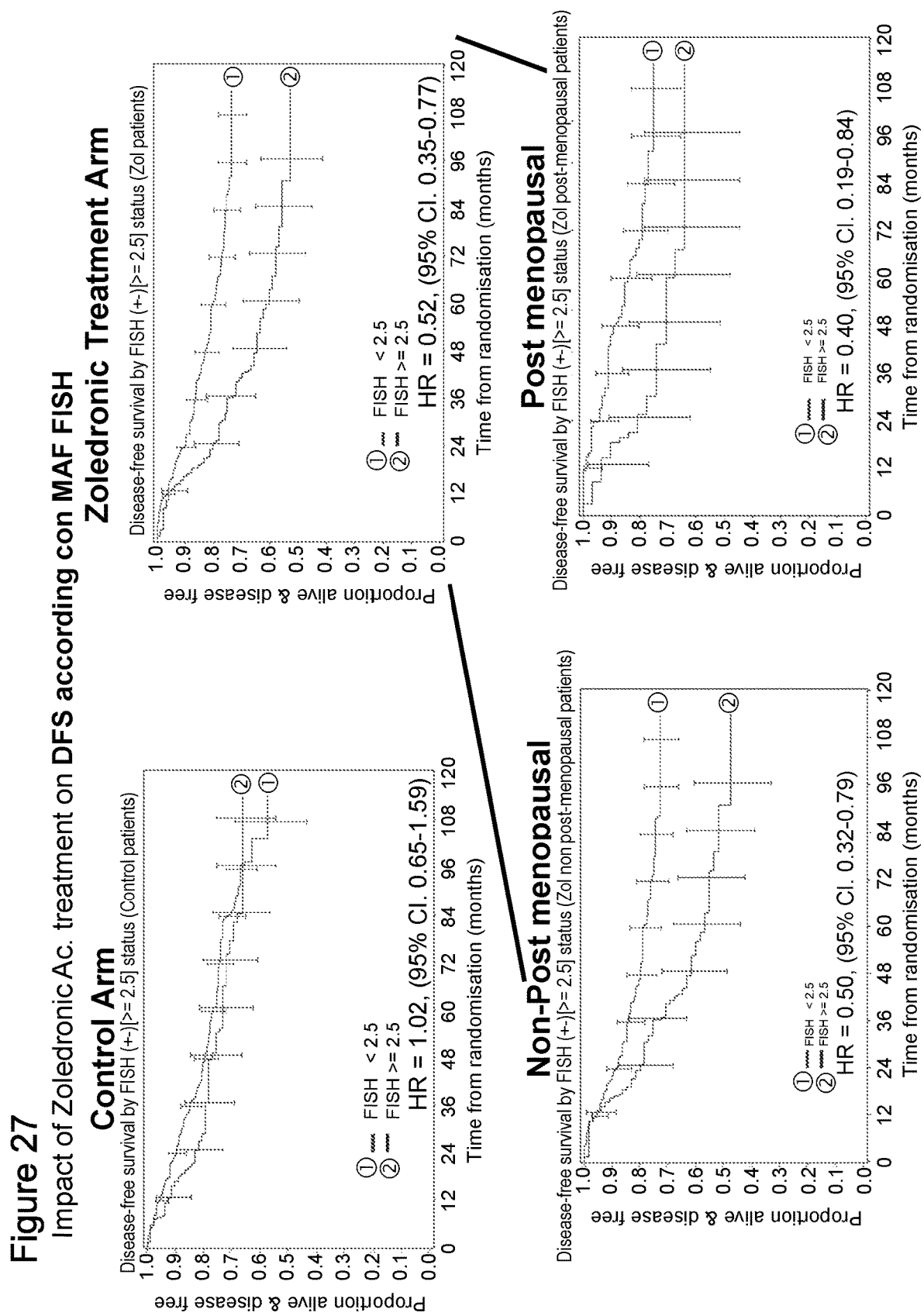
FIG. 27. Predictive value of MAF FISH for the effect of zoledronic acid treatment on the disease free survival (DFS) outcome.

FIG. 25 shows the prognosis of disease free survival (DFS) in the AZURE control arm. As can be seen in FIG. 25, there is a significantly lower disease free survival in untreated MAF positive post-menopausal patients. With regard to disease free survival: the significance of FISH status and menopausal status interaction covariate in multivariate analysis (in control patients); $Chi^2=6.23$, p-value=0.013. FIG. 26 shows the prognosis of overall survival in AZURE control arm patients. There is a trend to a shorter OS in untreated MAF positive post-menopausal patients. With regard to OS: the significance of FISH status and menopausal status interaction covariate in multivariate analysis (in control patients); $Chi^2=3.62$, p-value=0.057. FIG. 27 shows the impact of zoledronic acid treatment on DFS according to the MAF FISH value. As can be seen in FIG. 27, zoledronic acid treatment produces a differential DFS outcome between MAF FISH positive and negative patients, and these differences take place in post and non-post menopausal women.

Figure 29:
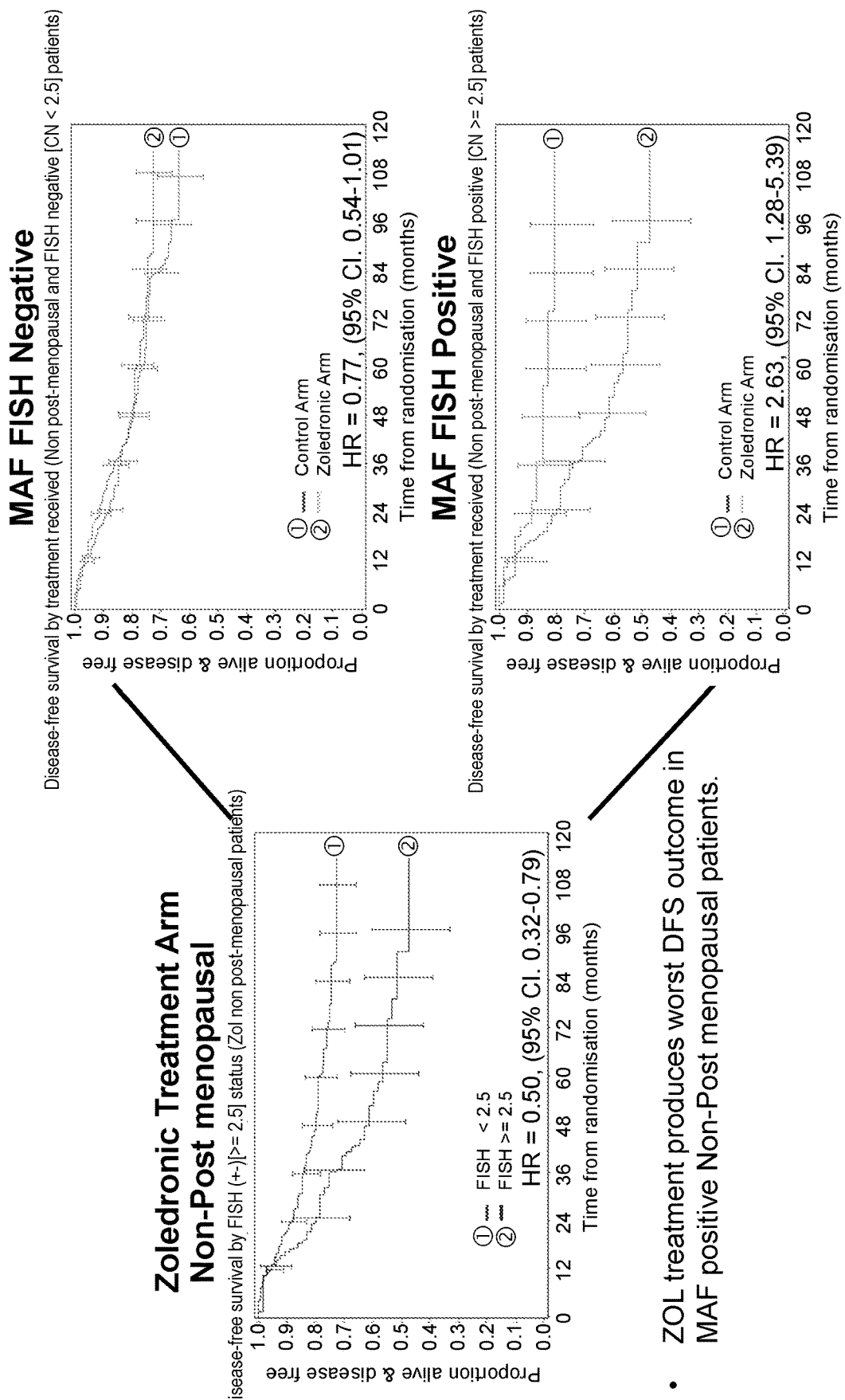
FIG. 29. Predictive value of MAF FISH for the effect of zoledronic acid treatment on the disease free survival (DFS) outcome on non-post menopausal patients.
Figure 32:
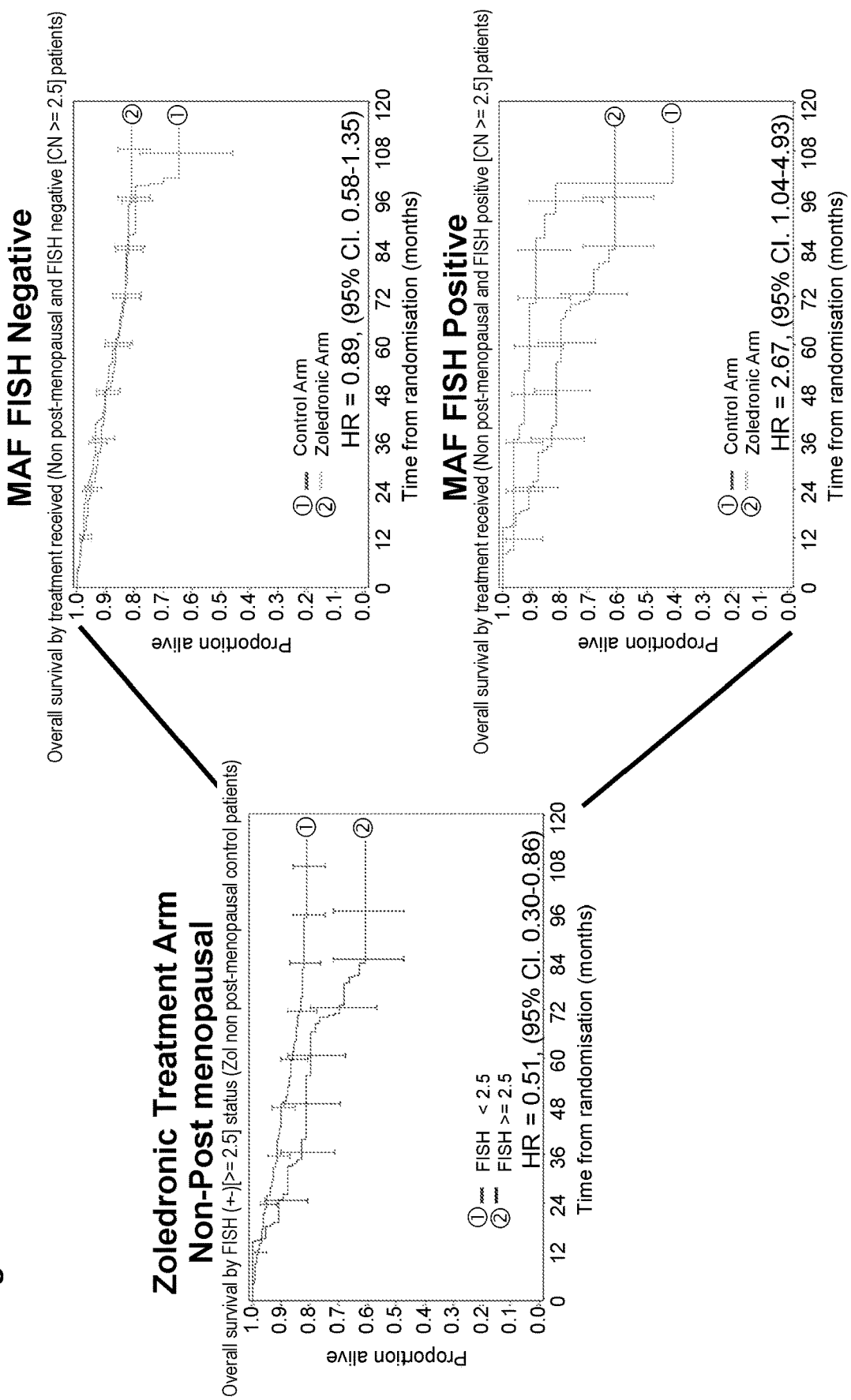
FIG. 32. Predictive value of MAF FISH for the effect of zoledronic acid treatment on the OS outcome in non-post menopausal patients.

FIG. 28 shows the impact of zoledronic acid treatment on DFS according to the MAF FISH value on postmenopausal patients. As can be seen in FIG. 28, zoledronic acid treatment produces a better DFS outcome in MAF negative post menopausal patients (HR=0.56, (95% CI., 0.33-0.95). FIG. 29 shows the impact of zoledronic acid treatment on the DFS of non-post menopausal women. As can be seen in FIG. 29, zoledronic acid treatment produces the worst DFS outcome in MAF positive non-post-menopausal patients. FIG. 30 shows the impact of zoledronic acid treatment on overall survival according to the MAF FISH value. As can be seen in FIG. 30, zoledronic acid treatment produces a significantly shorter overall survival in MAF positive patients. These differences take place in post and non-post menopausal women. FIG. 31 shows the impact of zoledronic acid treatment on overall survival according to MAF FISH levels in post menopausal patients. As can be seen in FIG. 31, zoledronic acid treatment shows a trend to a better overall survival outcome in MAF negative post menopausal patients. HR=0.56, (95% CI., 0.31-1.01), but a larger effect in zoledronic FISH positive patients. FIG. 32 shows the impact of zoledronic acid treatment on the overall survival of non-postmenopausal women according to MAF FISH value. As can be seen in FIG. 32, zoledronic acid treatment produces the worst overall survival outcome in MAF positive non-post menopausal patients.

A summary of the predictive value of the gene of interest (GOI) MAF on the risk of the patients for DFS and OS broken according to menopausal status is seen in Table 1.

TABLE 1

Hazard ratio for predictive power of MAF based on menopausal status

| | Hazard ratio (HR) | Lower limit of 95% CI for HR | Upper limit of 95% CI for HR |
|---|---|---|---|
| GOI status: negative v. positive for pre-menopausal patients | 3.134 | 0.913 | 10.760 |
| GOI status: negative v. positive for less than or equal to 5 years since menopause patients | 0.667 | 0.202 | 2.200 |
| GOI status: negative v. positive for more than 5 years since menopause patients | 0.552 | 0.280 | 1.089 |
| GO status: negative v. positive for menstrual status unknown patients | 0.656 | 0.121 | 3.559 |

As can be seen, MAF is predictive in postmenopausal, unknown and perimenopausal patients at risk of a shorter DFS or worst OS. However in premenopausal women, MAF positive patients are those at less risk and are more likely to have a longer DFS and better OS.

In summary, there is a significant increased risk of bone metastasis as first site of recurrence in MAF FISH positive v. non positive patients of the control arm. (HR=0.47, p=0.013 with a cutoff=2.3) and this difference is reduced upon treatment with zoledronic acid. In addition, zoledronic acid treatment significantly reduced the risk of bone metastasis at any time on MAF FISH non positive patients (HR=0.65, p=0.03, cutoff=2.5). Zoledronic acid treatment shows an increased risk of bone metastasis at any time on MAF positive patients. The difference is non-significant (HR=1.54, p=0.22, cutoff=2.5). This effect is driven by menopausal status and shows the largest effect in the non-postmenopausal group. Zoledronic acid improves the outcome of MAF FISH positive postmenopausal patients significantly. However, zoledronic acid worsens the outcome of MAF FISH positive non-postmenopausal patients. The effect is dependent on an increase in invasive disease (reduced IDFS) upon treatment with Zoledronic acid (suggesting that prevention of metastasis to the bone may facilitate metastasis elsewhere in non postmenopausal patients and eventually lead to metastasis to the bone as a secondary event).

MAF FISH positive patients who are not treated with zoledronic acid have a higher risk of bone metastasis and Invasive Disease (reduced IDFS including and excluding bone events). In patients treated with zoledronic acid, MAF positive patients have a worse outcome compared to untreated patients in terms of bone metastasis at any time, IDFS (including an excluding bone events) and overall survival. MAF negative patients treated with zoledronic acid have a better outcome compared to untreated patients with regard to bone metastasis at any time risk. With regard to post-menopausal women, there is a better outcome with regard to IDFS (excluding bone) in MAF positive patients treated with zoledronic acid. In non-postmenopausal women there is a worse outcome with regard to IDFS (excluding bone) in MAF positive patients treated with zoledronic acid.

Example 3: Effect of MAF Amplification on Treatment Outcomes with Adjuvant Zoledronic Acid in Early Cancer MAF amplification was investigated as a predictor of the likelihood of benefit from adjuvant zoledronic acid in primary tumors.

Methods

Study Design and Patients 3,360 patients from 174 centers worldwide were recruited to the AZURE trial between Sep. 4, 2003, and Feb. 16, 2006. Eligible patients had histologically confirmed invasive stage II or III breast cancer of any subtype, with either pathologically involved axillary lymph node metastasis or a T3 or T4 primary tumor treated with curative intent and complete resection of the primary tumor (or planned resection if patients were being treated with neoadjuvant chemotherapy). Other inclusion criteria were age 18 years or older, Karnofsky performance status score 80 or more, and not being pregnant or breastfeeding. Patients were excluded if they had clinical or imaging evidence of distant metastases, current or recent (<1 year) use of bisphosphonates, or pre-existing bone disease likely to require bone-targeted treatment. All patients gave written informed consent. In the UK, patients also provided voluntary specific consent for use of biological materials (primary tumor and blood samples). Before randomization, patients underwent hematological, renal, hepatic function, and staging imaging tests according to institutional protocols. Those confirmed to be eligible were randomly assigned (1:1) to standard adjuvant systemic treatment alone or with zoledronic acid from a central computer-generated schedule held at the Clinical Trials Research Unit, University of Leeds, Leeds, UK. A minimization process that took into account the number of involved axillary lymph nodes, clinical tumor stage, estrogen receptor status, type and timing of systemic therapy, menopausal status, statin use, and treating center was used.

Procedures

Drug Treatment

Patients received standard systemic therapy with (neo-)adjuvant chemotherapy, endocrine therapy, or both, alone (control group) or with 4 mg zoledronic acid given intravenously every 3-4 weeks for the first six doses, every 3 months for eight doses, and every 6 months for five doses to complete 5 years of treatment (zoledronic acid group). Oral calcium and vitamin D supplements were recommended for all patients in the first 6 months of treatment, and continued thereafter at the discretion of the treating physician. Adjuvant systemic treatments and locoregional radiotherapy were used in accordance with the standard protocols of each participating institution.

The follow-up schedule was similar in both study groups, and included clinical assessments, monitoring of adverse events, and hematological, renal, and hepatic function tests. Routine follow-up imaging was not mandated, but investigations were done for clinically suspected recurrence if deemed appropriate by the treating physician. Recurrence was defined by the date on which it was first suspected, to reduce the risk of ascertainment bias. 91% of recurrences were independently validated by either on-site or telephone based monitoring. After treatment with zoledronic acid was completed, patients were followed up annually for disease and safety endpoints.

Measurement of MAF Amplification

5 μm thick slices were cut from each TMA block and oriented to match the TMA map to allow identification of each tissue core. The slices were mounted onto Superfrost plus glass slides (Thermo Fisher Scientific, Waltham, MA, USA) and stained with hematoxylin and eosin to confirm the presence of assessable tumor. MAF amplification was assessed with the validated MAFTEST fluorescence in situ hybridization (FISH) with the MAF/D16Z3 probe (Inbiomotion, Barcelona, Spain). A central laboratory (Targos Molecular Pathology, Kassel, Germany) validated the analytical and diagnostic performance of the assay, established acceptance criteria, included appropriate quality controls for each assay, and performed the analyses masked to treatment assignment. Briefly, TMA sections were rehydrated in ethanol series, washed with water, and pretreated at 98° C. for 15 min. Samples were digested with pepsin in a Poseidon Tissue Digestion Kit (Kreatech, Amsterdam, Netherlands) for 30 min, dehydrated in ethanol series, and dried. After adding 10 μL MAF/D16Z3 probe, slides were denatured at 80° C. and placed overnight in a hybridiser at 37° C. After hybridization, FISH slides were washed in Poseidon Tissue Digestion Kit Wash Buffer I at 72° C. for 2 min and then Wash Buffer II for 1 min at room temperature. After dehydration and air-drying, slides were incubated with 15 μL 4,6-diamidino-2-phenylindole solution (0.03 mg/mL) and stored at 4° C. in the dark until scoring.

Mean MAF copy number per nucleus was scored in 20 nuclei from the region of the tumor with the highest amplification, by laboratory staff who were masked to treatment group. If the mean copy number was between 2·0 and 3·0, 30 more nuclei were scored. To keep the effect of tumor heterogeneity in such small fragments to a minimum, duplicate results were mandated for each patient. Thus, replica cores were scored until two FISH amplification values were obtained for each tumor, of which the highest per patient was used in the statistical analysis. The TMAs were analyzed by FISH without optimization or repetition, as stipulated in the study protocol. Patients for whom the mean MAF copy number was 2·5 or greater in at least one replica were deemed to be MAF positive. This threshold was based on studies in a retrospective cohort and judged unlikely to be artificially affected by rapid tumor cell proliferation.

Results 1,739 (64%) of 2,710 patients enrolled at eligible UK sites gave consent and had primary tumor samples sent for central analysis. Samples were processed between September 2003 and March 2006, and TMAs were prepared in 2007 and 2008. 3,978 (63%) of 6,326 TMA cores had sufficient invasive tumor for FISH analysis. The MAFTEST FISH assay could be reliably assessed in 2,067 (56%) of these 3,978 tissues cores. 865 (50%) of 1,739 patients had two assessable FISH results (445 in the control group and 420 in the zoledronic acid group), and of these, 184 (21%) had MAF-positive tumors (85 in the control group and 99 in the zoledronic acid group).

The median follow-up was 84·6 months (IQR 72·0-95·8). 282 (33%) of 865 patients had an invasive-disease-free survival event (147 in the control group and 135 in the zoledronic acid group), 60 had a first event in bone (39 and 21), and 193 had died (102 and 91). 5-year invasive-disease free-survival was 74·1% (95% CI 69·8-78·3) in the zoledronic acid group and 73·7% (69·6-77·8) in the control group; values were similar to those in the overall AZURE trial population.

Figure 33:
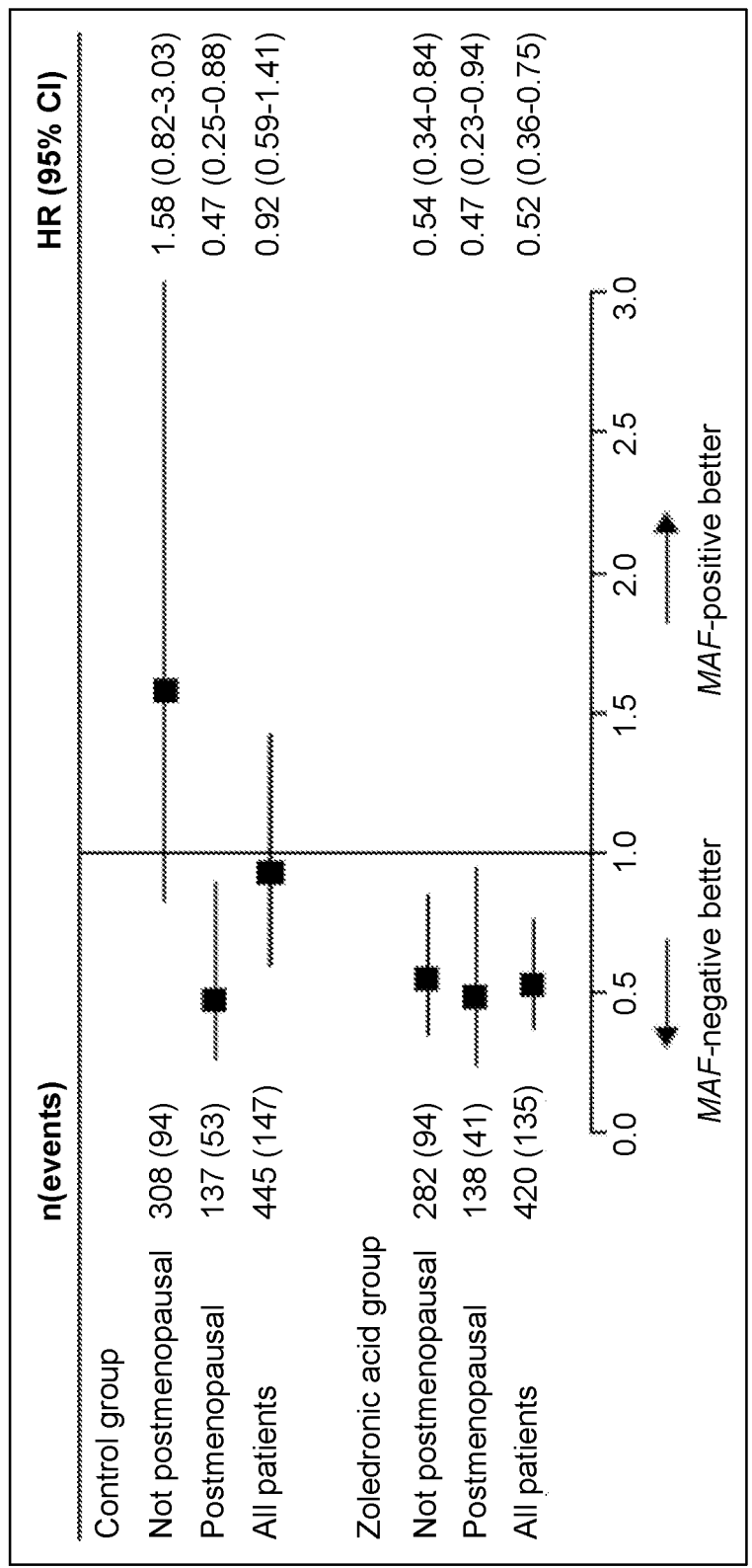
FIG. 33. The effect of MAF copy number on invasive-disease-free survival. HRs and 95% CIs are based on Cox multivariable analysis. HR=hazard ratio.

Among patients in the control group, 118 (33%) of 360 with MAF-negative tumors and 29 (34%) of 85 with MAF-positive tumors had an invasive-disease-free survival event, suggesting that MAF status was not prognostic for this endpoint (FIG. 33). This result, however, is not fully representative of the data because the effect of MAF status on disease outcome was dependent on menopausal status at the start of treatment ($\chi^2$=7·34, degree of freedom [df] 1, pinteraction=0·009). Among postmenopausal patients in the control group, MAF-negative status was associated with a shorter invasive-disease-free survival than was MAF-positive status, whereas among non-postmenopausal patients, the invasive-disease-free survival was longer for patients with MAF-negative tumors than those with MAF positive tumors (FIG. 33). In the zoledronic acid group, invasive-disease-free survival was shorter in patients with MAF-positive tumors than in those with MAF-negative tumors, meaning that MAF status provided prognostic information (FIG. 33). A similar effect was seen for overall survival. Menopausal status did not substantially alter the effect of MAF status on disease outcome in the zoledronic acid group (FIG. 33).

Figure 34:
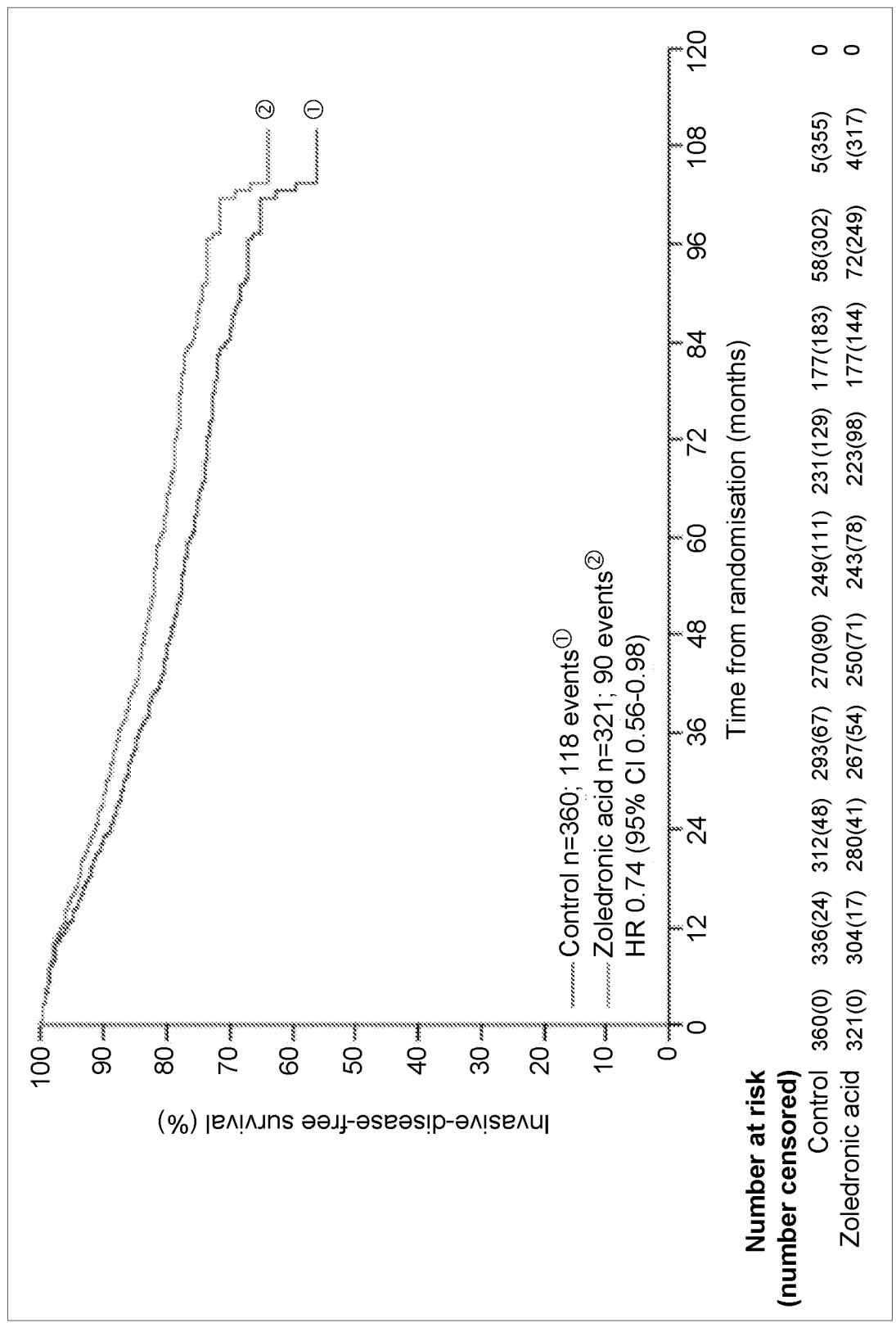
FIG. 34. Invasive-disease-free survival by treatment group in MAF-negative patients. Output from Cox multivariable model adjusted for differences in the prognostic factors between groups. HR=hazard ratio.
Figure 35:
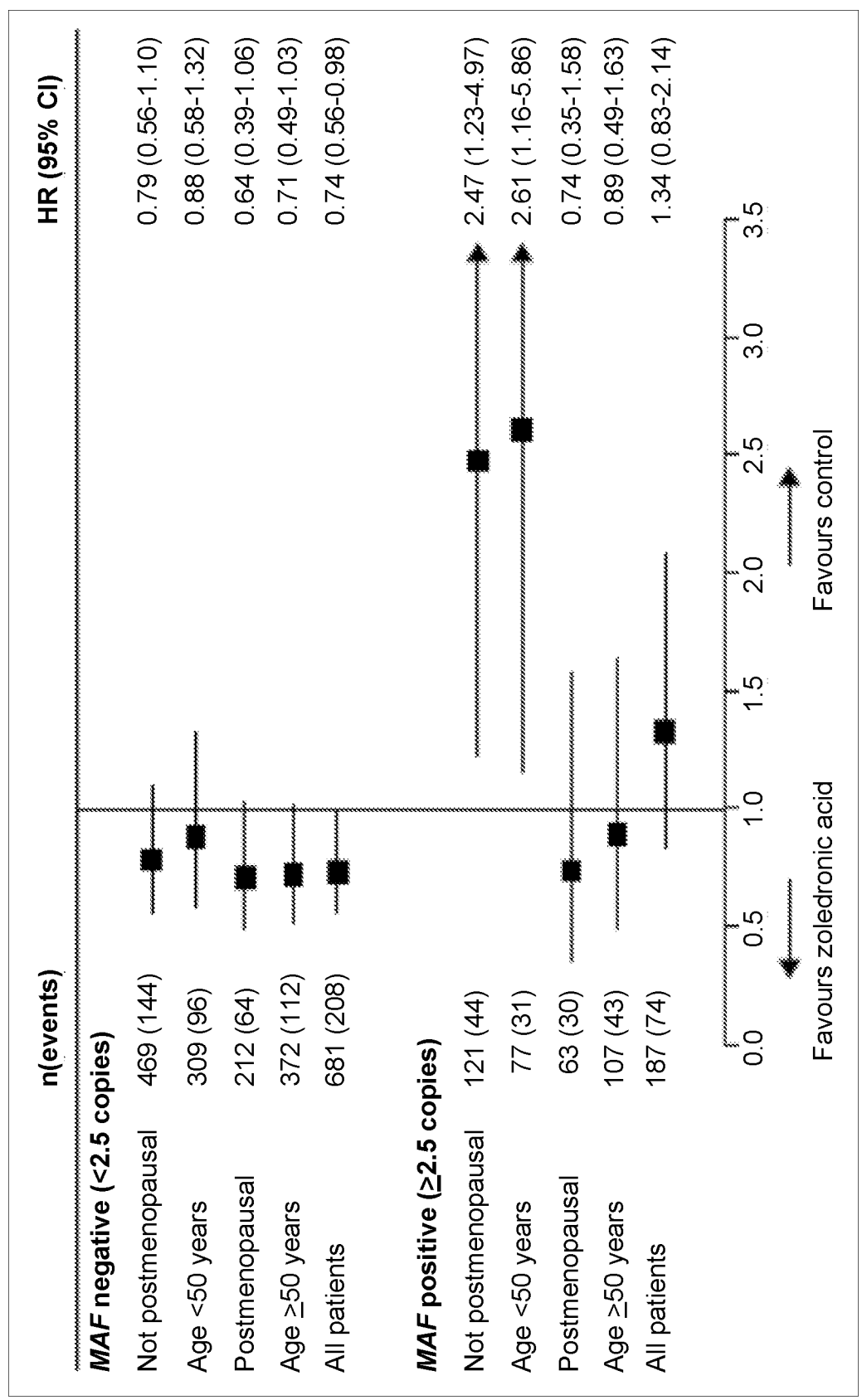
FIG. 35. The effect of MAF status on association between adjuvant zoledronic acid and invasive-disease-free survival, stratified by menopausal status and age. HR=hazard ratio.

In patients with MAF-negative tumors, treatment with zoledronic acid was associated with longer invasive-disease-free survival than standard treatment alone (FIG. 34). Treatment benefits with zoledronic acid were similar irrespective of menopausal status or age (FIG. 35). By contrast, in patients with MAF positive tumors, although zoledronic acid was not associated with longer invasive-disease-free survival, there was significant heterogeneity in the treatment effect by menopause status and age (FIG. 35). Not being postmenopausal at the start of treatment or age younger than 50 years had clear adverse effects on invasive-disease-free survival in patients treated with zoledronic acid (FIG. 35). In postmenopausal women, the number of events in those with MAF-positive tumors was insufficient to establish a definitive association between MAF status and treatment effect, although the HR was similar (albeit with wider confidence intervals) to that seen in MAF-negative women (FIG. 35).

For overall survival, a similar association between treatment, menopause, and MAF status was seen. Fewer patients with MAF-negative tumors treated with zoledronic acid died than did those in the control group (57 [18%] of 321 vs 76 [21%] of 360; HR 0·78, 95% CI 0·55-1·10). Among patients with MAF-positive tumors, no effect of zoledronic acid was seen on overall survival (34 [34%] of 99 died vs 26 [31%] of 85; HR 1·11, 95% CI 0·66-1·86). In women with MAF-positive tumors who were non-postmenopausal at the start of treatment there was, however, a clear adverse effect of zoledronic acid on overall survival (24 [36%] of 66 patients in the zoledronic acid group died vs nine [16%] of 55 patients in the control group; HR 2·27, 95% CI 1·04-4·93), which contrasts with the treatment effect of zoledronic acid on overall survival in postmenopausal women with MAF-positive tumors (ten [30%] of 33 patients in the zoledronic acid group died vs 17 [57%] of 30 in the control group; 0·62, 0·27-1·48).

Figure 36A:
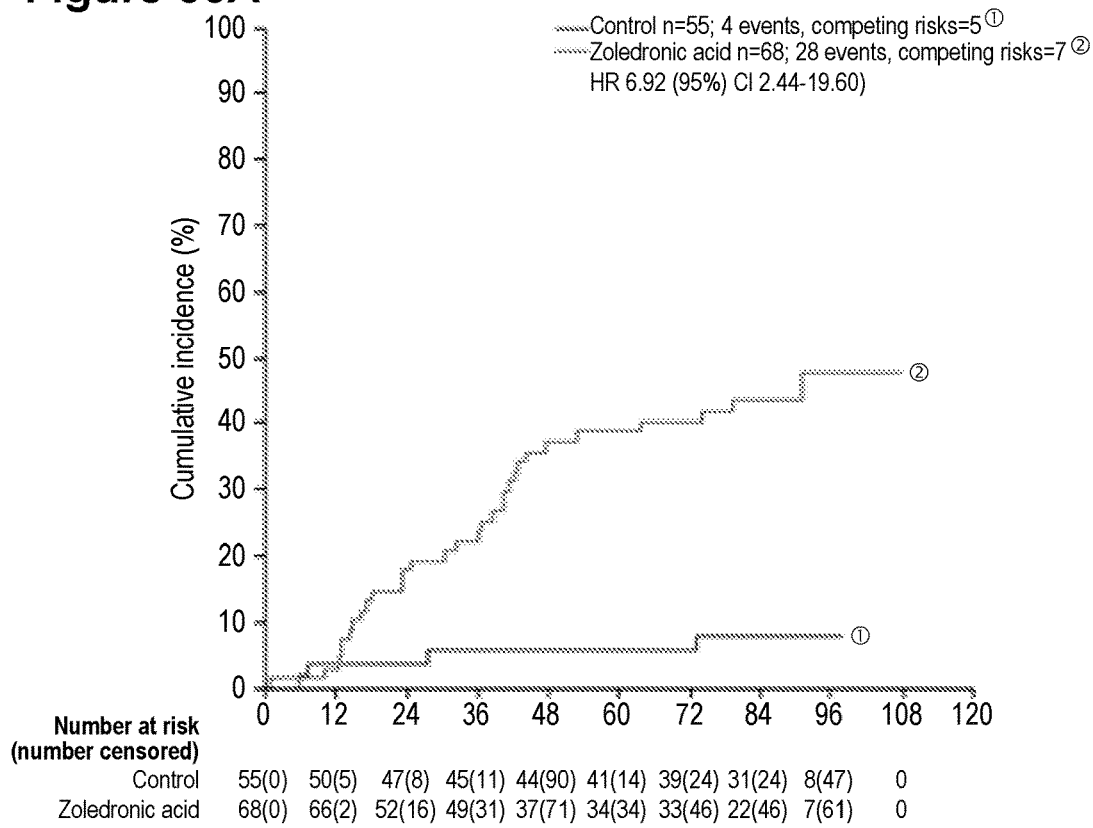
FIGS. 36A-36B. The cumulative risk of extraskeletal first recurrence in women not postmenopausal at trial entry, by treatment group.
Figure 36B:
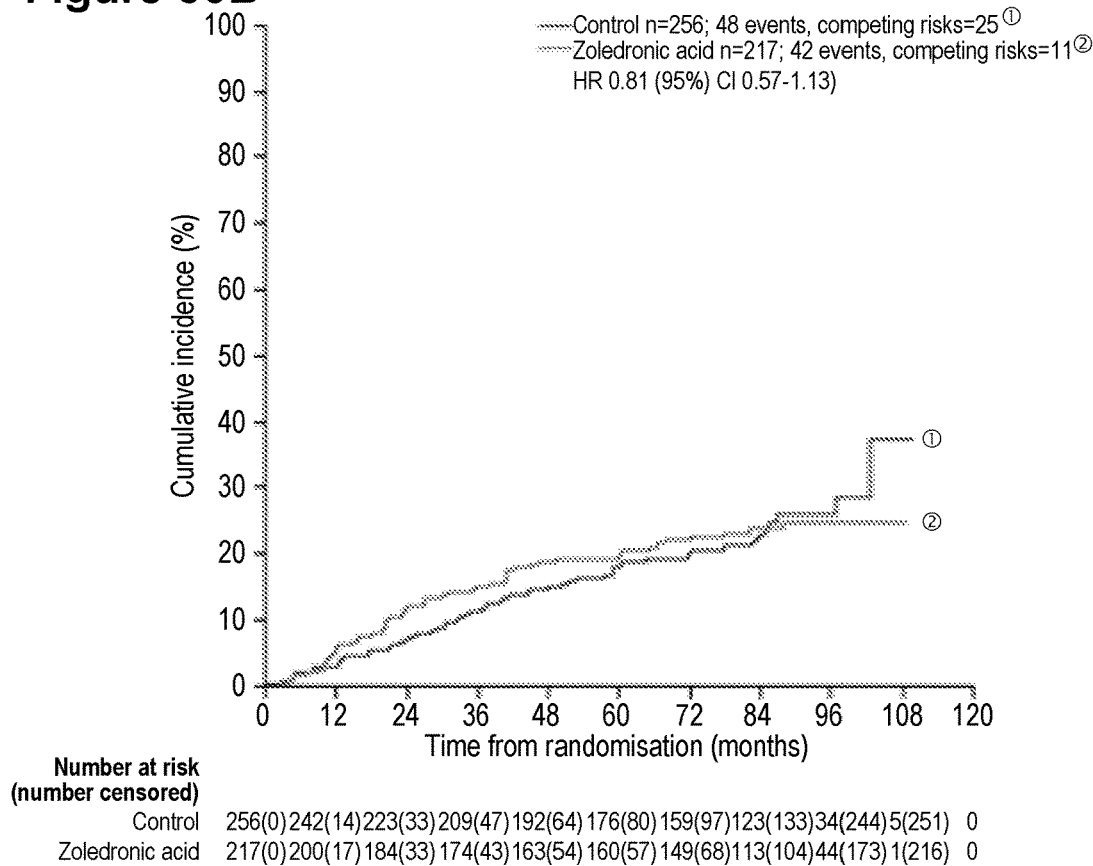

190 patients had an extraskeletal invasive-disease-free survival event (92 in the control group and 98 in the zoledronic acid group). When compared with the control group, treatment with zoledronic acid in nonpostmenopausal women with MAF-positive tumors was associated with a marked increase in relapse at extraskeletal sites (FIGS. 36A-36B). The estimated extra-skeletal invasive-disease-free survival at 60 months for patients with MAF-positive tumors was 5·7% (95% CI 1·5-14·2) in the control group and 38·8% (27·1-50·3) in the zoledronic acid group (FIGS. 36A-36B), No effect of zoledronic acid treatment on extraskeletal recurrence in patients with MAF-negative tumors who were nonpostmenopausal at the start of treatment was observed (extraskeletal invasive-disease-free survival at 60 months was 18·0%, 95% CI 13·5-23·1 in the control group and 19·8%, 14·8-25·5 in the zoledronic acid group; (FIGS. 36A-36B).

The menopausal subgroup analyses indicated that menopausal status at the start of treatment played a part in the association between MAF status and invasive disease-free survival (likelihood ratio test for the threeway interaction term between MAF status, menopausal status, and treatment: $\chi^2=5·71$, df 1; p=0·017). Heterogeneity in the treatment effect by menopausal status was found for MAF-positive tumors ($\chi^2=6·98$, df 1; p=0·008), but not MAF-negative tumors ($\chi^2=0·38$, df 1; p=0·539).

Compared with non-postmenopausal control patients with MAF-negative tumors, individual HRs were consistent with the primary analysis that invasive-disease free survival is independent of menopausal status when patients are treated with zoledronic acid (Table 2).

TABLE 2

Invasive-disease-free survival by MAF status, menopausal status and treatment.

| | Number of patients (number of events) | Hazard ratio (95% CI) |
|---|---|---|
| MAF-negative | | |
| Non-postmenopausal control group | 253 (83) | 1 |
| Postmenopausal control group | 107 (35) | 1 · 25 (0 · 80-1 · 95) |
| Non-postmenopausal zoledronic acid group | 216 (61) | 0 · 83 (0 · 59-1 · 15) |
| Postmenopausal zoledronic acid group | 105 (29) | 0 · 85 (0 · 53-1 · 36) |
| MAF-positive | | |
| Non-postmenopausal control group | 55 (11) | 0 · 63 (0 · 33-1 · 20) |
| Postmenopausal control group | 30 (18) | 2 · 68 (1 · 53-4 · 60) |
| Non-postmenopausal zoledronic acid group | 66 (33) | 1 · 61 (1 · 06-2 · 44) |
| Postmenopausal zoledronic acid group | 33 (12) | 1 · 72 (0 · 90-3 · 29) |

Heterogeneity in outcomes by menopausal status in addition to MAF status was noted in patients in the control groups, as those with MAF-positive tumors who were not postmenopausal at the start of treatment had significantly better invasive-disease-free survival than those who were postmenopausal (HR 0·26, 95% CI 0·12-0·56). Non-postmenopausal patients in the control group with MAF-positive tumors had a longer invasive-disease-free survival than patients in the control group with MAF-negative tumors (Table 2).

No difference in invasive-disease-free survival was found when age was used as a surrogate marker for menopause (Table 3), with similar beneficial effects in both age groups seen with zoledronic acid in patients with MAF negative tumors (FIG. 35).

TABLE 3

Effect of MAF status on invasive-disease-free survival, by age

| | Number of patients (number of events) | Hazard ratio (95% CI)* |
|---|---|---|
| Zoledronic acid group | | |
| <50 years | 142 (41) vs 44 (23) | 0 · 473 (0 · 281-0 · 797) |
| ≥50 years | 179 (49) vs 55 (22) | 0 · 533 (0 · 719-0 · 890) |
| Control group | | |
| <50 years | 167 (55) vs 33 (8) | 1 · 410 (0 · 666-2 · 985) |
| ≥50 years | 193 (63) vs 52 (21) | 0 · 673 (0 · 407-1 · 114) |

*MAF-negative vs MAF-positive tumours.

CONCLUSIONS

Increased tumor copy number of MAF, when measured by FISH in primary breast tumor TMAs, predicted treatment benefit and harm associated with adjuvant zoledronic acid. In addition, adjuvant zoledronic acid improved disease outcomes in the 79% of patients with MAF-negative tumors (mean copy number<2·5). This beneficial treatment effect was independent of menopausal status at study entry, which suggests that the use of adjuvant bisphosphonates could be extended to the 80% of premenopausal women who have MAF-negative tumors.

While the present application has been illustrated by the description of embodiments and examples thereof, and while the embodiments and examples have been described in detail, it is not the intention of the applicants to restrict or in any way limit the scope of the claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples and apparatuses without departing from the spirit or scope of the general inventive concept.

All publications, patents, patent applications, internet sites, and accession numbers/database sequences including both polynucleotide and polypeptide sequences cited herein are hereby incorporated by reference herein in their entirety

What is claimed is:

1. A method for the treatment of a subject having breast cancer, comprising administering to the subject alendronate at a dose of from about 50 mg to about 100 mg, administering risedronate at a dose of from about 20 mg to about 50 mg, or administering ibandronate at a dose from about 100 mg to about 200 mg, wherein the subject has been identified as having a not increased c-MAF gene expression level, copy number, amplification, or gain in a tumor sample compared to a reference value.

2. A method for the treatment of a subject having breast cancer, comprising:
   (i) quantifying the c-MAF gene expression level, copy number, amplification, or gain in a sample of said subject, and
   (ii) comparing the expression level, copy number, amplification, or gain obtained in (i) with a reference value,
   wherein said subject has a not increased c-MAF gene expression level, copy number, amplification, or gain with respect to said reference value, and said subject is administered alendronate at a dose of from about 50 mg to about 100 mg, administered risedronate at a dose of from about 20 mg to about 50 mg, or administered ibandronate at a dose from about 100 mg to about 200 mg.

3. A method for the identification of a subject having breast cancer who will benefit from treatment with alendronate, risedronate, or ibandronate, comprising:
   (i) quantifying the c-MAF gene expression level, copy number, amplification, or gain in a sample of said subject, and
   (ii) comparing the expression level, copy number, amplification, or gain obtained in (i) with a reference value,
   wherein said subject has a not increased c-MAF gene expression level, copy number, amplification, or gain with respect to said reference value, and said subject is administered alendronate at a dose of from about 50 mg to about 100 mg, administered risedronate at a dose of from about 20 mg to about 50 mg, or administered ibandronate at a dose from about 100 mg to about 200 mg.

4. An in vitro method for designing a customized therapy for a subject having breast cancer which comprises:
   (i) quantifying the c-MAF gene expression level, copy number, amplification, or gain in a sample of said subject, and
   (ii) comparing the expression level, copy number, amplification, or gain obtained in (i) with a reference value,
   wherein said subject has a not increased c-MAF gene expression level, copy number, amplification, or gain with respect to said reference value, and said subject is administered alendronate at a dose of from about 50 mg to about 100 mg, administered risedronate at a dose of from about 20 mg to about 50 mg, or administered ibandronate at a dose from about 100 mg to about 200 mg.

5. The method of claim 1, wherein the subject is administered about 50 mg, about 60 mg, about 70 mg, about 80 mg, about 90 mg, or about 100 mg of alendronate.

6. The method of claim 5, wherein the alendronate is administered weekly.

7. The method of claim 1, wherein the subject is administered about 20 mg, about 25 mg, about 30 mg, about 35 mg, about 40 mg, about 45 mg, or about 50 mg of risedronate.

8. The method of claim 7, wherein the risedronate is administered weekly.

9. The method of claim 1, wherein the subject is administered about 100 mg, about 110 mg, about 120 mg, about 130 mg, about 140 mg, about 150 mg, about 160 mg, about 170 mg, about 180 mg, about 190 mg, or about 200 mg of ibandronate.

10. The method of claim 9, wherein the ibandronate is administered monthly.

11. The method of claim 1, wherein the alendronate, risedronate, or ibandronate is administered with an additional therapy.

12. The method of claim 1, wherein the breast cancer is Stage 0 breast cancer.

13. The method of claim 1, wherein the breast cancer is Stage I, Stage II, Stage III, Stage IV, or metastatic breast cancer.

14. The method of claim 1, wherein the method further comprises quantifying the messenger RNA (mRNA) of said c-MAF gene, or a fragment of said mRNA, the complementary DNA (cDNA) of said c-MAF gene, or a fragment of said cDNA or quantifying the level of protein encoded by said c-MAF gene.

15. The method of claim 1, wherein the expression level, copy number, amplification of gain is quantified by means of a quantitative polymerase chain reaction (PCR) or a DNA or RNA array, FISH, in situ hybridization, or nucleotide hybridization technique.

16. The method of claim 14, wherein the level of protein is quantified by means of western blot, ELISA, immunohistochemistry or a protein array.

17. The method of claim 1, wherein the breast cancer is ER+ breast cancer.

18. The method of claim 1, wherein the breast cancer is ER-breast cancer, triple negative breast cancer, of the basal-like subtype, or HER2+ breast cancer.

19. The method of claim 1, wherein the subject is non-postmenopausal.

20. The method of claim 1, wherein the subject is premenopausal or postmenopausal.

21. The method of claim 1, wherein the treatment or therapy improves invasive disease free survival or disease free survival.

22. The method of claim 1, wherein the treatment or therapy improves overall survival.

* * * * *

SEQUENCE LISTING

```
Sequence total quantity: 24
SEQ ID NO: 1              moltype = DNA   length = 6878
FEATURE                   Location/Qualifiers
source                    1..6878
                          mol_type = genomic DNA
                          organism = Homo sapiens
SEQUENCE: 1
agaggcttta aaatcttttt tcatcttcta gctgtagctc gggctgcttg tcggcttggc    60
ctcccccctcc cccctttgct ctctgcctcg tctttcccca ggacttcgct attttgcttt   120
tttaaaaaaa ggcaagaaag aactaaactc cccctccct ctcctccagt cgggctgcac    180
ctctgccttg cactttgcac agaggtagag agcgcgcgag ggagagagag gaaagaaaaa    240
aaataataaa gagagccaag cagaagagga ggcgagaagc atgaagtgtt aactccccg    300
tgccaaggcc cgcgccgccc ggacagacgc ccgccgcgcc tccagccccg agcggacgcc    360
gcgcgcgccc tgcctgcagc ccgggccggc gaggcgagcc cttccttatg caaagcgcgc    420
agcggagcgg cgagcggggg acgccgcgca ccgggccggg ctcctccagc ttcgccgccg    480
cagccaccac cgccgccacc gcagctcgcg gaggatcttc ccgagcctga agccgccggc    540
tcggcgcgca aggaggcgag cgagcaagga ggggcgcggg cgagcgaggg agcacattgg    600
cgtgagcagg ggggagggag ggcgggcgcg ggggcgcgg gcagggcggg ggggtgtgtg    660
tgtgagcgcg ctcggaggtt tcgggccagc caccgccgcg caagctagaa gcgccccagc    720
ccggcaagct ggctcacccg ctggccaccc agcacagccc gctggcccct ctcctgcagc    780
ccatctggcg gagcggcggc ggcggcggcg gcggcggcag gagaatggca tcagaactgg    840
caatgagcaa ctccgacctg cccaccagtc ccctggccat ggaatatgtt aatgacttcg    900
atctgatgaa gtttgaagtg aaaaaggaac cggtggagac cgaccgcatc atcagccagt    960
gcggccgtct catcgccggg ggctcgctgt cctccacccc catgagcacg ccgtgcagct   1020
cggtgccccc ttccccaccc ttctcggcgc ccagccccgg ctcgggcagc gagcagaagg   1080
cgcacctgga agactactac tggatgaccg gctaccgca gcagctgaac cccgaggcgc   1140
tgggcttcag ccccgaggac gcggtcgagg cgctcatcag caacagccac cagctccagg   1200
gcggcttcga tggctacgcg cgcggggcgc agcagctggc cgcggcggcc ggggccggtg   1260
ccggcgcctc cttgggcggc agcggcgagg agatgggccc cgccgccgcc gtggtgtccg   1320
ccgtgatcgc cgcggccgcc gcgcagagcg gcgcgggccc gcactaccac caccaccacc   1380
accacgccgc cggccaccac caccacccga cggccgcgcc gcccggcgcc gcgggcagcg   1440
cggccgcctc ggccggtggc gctggggcg cgggcggcgg tggcccggcc agcgctgggg   1500
gcggcggcgg cggcggcggc ggcggaggcg gcgggggcgc ggcggggcg gggggcgccc   1560
tgcacccgca ccacgccgcc ggcggcctgc acttcgacga ccgcttctcc gacgagcagc   1620
tggtgaccat gtctgtgcgc gagctgaacc ggcagctgcg cgggtcagc aaggaggagg   1680
tgatccggct gaagcagaag aggcggaccc tgaaaaaccg cggctatgcc cagtcctgcc   1740
gcttcaagag ggtgcagcag agacacgtcc tggagtcgga gaaaccag ctgctgcagc    1800
aagtcgacca cctcaagcag gagatctcca ggctggtgcg cgagagggac gcgtacaagg   1860
agaaatacga gaagttggtg agcagcggct tccgagaaaa cggctcgagc agcgacaacc   1920
cgtcctctcc cgagtttttc atgtgagtct gacacgcgat tccagctagc caccctgata   1980
agtgctccgc gggggtccgg ctcgggtgtg ggcttgctag ttctagagcc atgctcgcca   2040
ccacctcacc accccacccc ccaccgagtt tggccccctt ggccccctac acacacacaa   2100
acccgcacgc acacaccaca cacacacaca cacacacaca cacacccac accctgctcg   2160
agtttgtggt ggtggtggct gttttaaact ggggagggaa tgggtgtctg gctcatggat   2220
tgccaatctg aaattctcca taacttgcta gcttgttttt ttttttttt tacaccccc    2280
cgccccaccc ccggacttgc acaatgttca atgatctcag cagagttctt catgtgaaac   2340
gttgatcacc tttgaagcct gcatcattca catattttt cttcttcttc cccttcagtt    2400
catgaactgg tgttcatttt ctgtgtgtgt gtgtgtttta ttttgtttgg attttttttt   2460
ttaattttac tttagagct tgctgtgttg cccacctttt ttccaacctc caccctcact    2520
ccttctcaac ccatctcttc cgagatgaaa gaaaaaaaaa agcaaagttt tttttttctt   2580
tcctgagttc ttcatgtgag attgagcttg caaggaaaa aaaatgtga atgttatag     2640
acttgcagcg tgccgagttc catcgggttt ttttttttagc attgttatgc taaaatagag   2700
aaaaaaatcc tcatgaacct tccacaatca agcctgcatc aaccttctgg gtgtgacttg    2760
tgagttttgg ccttgtgatg ccaaatctga gagtttagtc tgccattaaa aaaactcatt    2820
ctcatctcat gcattattat gcttgctact ttgtcttagc aacaatgaac tataactgtt    2880
tcaaagactt tatggaaaag agacattata ttaataaaa aaaaagcct gcatgctgga     2940
catgtatggt ataattattt tttccttttt ttttccttt ggcttggaaa tggacgttcg     3000
aagacttata gcatggcatt catacttttg ttttattgcc tcatgcattt tttgagttta    3060
gaacaaaaca gtgcaaccgt agagccttct tcccatgaaa ttttgcatct gctccaaaac    3120
tgctttgagt tactcagaac ttcaacctcc caatgcactg aaggcattcc ttgtcaaaga    3180
taccagaatg ggttacacat ttaacctggc aaacattgaa gaactcttaa tgttttcttt    3240
ttaataagaa tgacgcccca ctttggggac taaaattgtg ctattgccga gaagcagtct    3300
aaaatttatt tttaaaaag agaaactgcc ccattatttt tggtttgttt tattttatt     3360
ttatattttt tggcttttgg tcattgtcaa atgtggaatg ctctgggttt ctagtatata    3420
atttaattct agttttttata atctgttagc ccagttaaaa tgtatgctac agataaagga    3480
atgttataga taaatttgaa agagttaggt ctgtttagct gtagattttt taaacgattg    3540
atgcactaaa ttgtttacta ttgtgatgtt aaggggggta gagtttgcaa gggggactgtt   3600
taaaaaaagt agcttataca gcatgtgctt gcaacttaaa tataagttgg gtatgtgtag    3660
tcttttgctat accactgact gtattgaaaa ccaaagtatt aagagggaa acgcccctgt    3720
ttatatctgt agggtattt tacattcaaa aatgtatgtt tttttttctt ttcaaaatta    3780
aagtatttgg gactgaattg cactaagata taacctgcaa gcatataata caaaaaaaa    3840
ttgcaaaact gtttagaacg ctaataaaat ttatgcagtt ataaaatgg cattactgca    3900
cagttttaag atgatgcaga ttttttttaca gttgtattgt ggtgcagaac tggattttct    3960
gtaacttaaa aaaaaatcca cagttttaaa ggcaataatc agtaaatgtt attttcaggg   4020
actgacatcc tgtctttaaa aagaaatgaa aagtaaatct taccacaata aatataaaaa   4080
```

```
aatcttgtca gttactttc ttttacatat tttgctgtgc aaaattgttt tatatcttga   4140
gttactaact aaccacgcgt gttgttccta tgtgcttttc tttcatttc aattctggtt    4200
atatcaagaa aagaataatc tacaataata aacggcattt ttttttgatt ctgtactcag  4260
tttcttagtg tacagtttaa ctgggcccaa caacctcgtt aaaagtgtaa aatgcatcct  4320
tttctccagt ggaaggattc ctggaggaat agggagacag taattcaggg tgaaattata  4380
ggctgttttt tgaagtgagg aggctggccc catatactga ttagcaatat ttaatataga  4440
tgtaaattat gacctcattt ttttctcccc aaagttttca gttttcaaat gagttgagcc  4500
ataattgccc ttggtaggaa aaacaaaaca aaacagtgga actaggcttc ctgagcatgg  4560
ccctacactt ctgatcagga gcaaagccat ccatagaccg aggagccgga caaatatggc  4620
gcatcagagg tggcttgcgc acatatgcat tgaacggtaa agagaaacag cgcttgcctt  4680
ttcactaaag ttgactattt ttccttcttc tcttacacac cgagattttc ttgttagcaa  4740
ggcctgacaa gatttaacat aaacatgaca aatcatagtt gtttgttttg ttttgctttt  4800
ctcttaaca ctgaagatca tttgtcttaa ataggaaaaa gaaaatccac tccttacttc   4860
catatttcca agtacatatc tggtttaaac tatgttatca aatcatattt caccgtgaat  4920
attcagtgga gaacttctct acctggatga gctagtaatg atttcagatc atgctatccc  4980
cagaaataaa agcaaaaaat aatacctgtg tggaatatag gctgtgcttt gatttactgg  5040
tatttacccc aaaataggct gtgtatgggg gctgacttaa agatcccttg gaaagactca  5100
aaactacctt cactagtagg actcctaagc gctgacctat ttttaaatga cacaaattca  5160
tgaaactaat gttacaaatt catgcagttt gcactcttag tcatcttccc ctagcacacc  5220
aatagaatgt tagacaaagc cagcactgtt ttgaaaatac agccaaacac gatgactttt  5280
gttttgtttt ctgccgttct taaagaaaa aaagataata ttgcaactct gactgaaaga   5340
cttattttta agaaaacagg ttgtgtttgg tgctgctaag ttctggccag tttatcatct  5400
ggccttcctg cctatttttt acaaaacacg aagacagtgt gtaacctcga cattttgacc  5460
ttcctttatg tgctagttta gacaggctcc tgaatccaca cttaattttg cttaacaaaa  5520
gtcttaatag taaacctccc ctcatgagct tgaagtcaag tgttcttgac ttcagatatt  5580
tctttccttt ttttttttt ttcctcatca caactaagag atacacaaac tctgaagaag  5640
cagaaatgga gagaatgctt ttaacaaaaa agcatctgat gaaagatttt aggcaaacat  5700
tctcaaaata agagtgatat tctgatgta gttattgcag ttatctcatg acaaatgagg   5760
cctggattgg aaggaaaata tagttgtgta gaattaagca ttttgatagg aatctacaag  5820
gtagttgaat ataataagca ggtttgggcc cccaaacttt agaaaatcaa atgcaaaggt  5880
gctggcaaaa atgaggtttg agtggctggc tgtaagagaa ggttaactcc tagtaaaagg  5940
cattttaga aataacaatt actgaaaact ttgaagtata gtgggagtag caaacaaata   6000
catgttttt ttttcttaca aagaactcct aaatcctgag taagtgccat tcattacaat   6060
aagtctctaa atttaaaaaa aaaaaaatca tatgaggaaa tctagctttc ccctttacgc  6120
tgcgtttgat ctttgtctaa atagtgttaa aattcctttc attccaatta cagaactgag  6180
cccactcgca agttggagcc atcagtggga tacgccacat tttggaagcc ccagcatcgt  6240
gtacttacca gtgtgttcac aaaatgaaat ttgtgtgaga gctgtacatt aaaaaaaatc  6300
atcattatta ttattatttg cagtcatgga gaaccaccta cccctgactt ctgtttagtc  6360
tccttttaa ataaaaatta ctgtgttaga gaagaaggct attaaatgta gtagttaact   6420
atgcctcttg tctggggggtt tcatagagac cggtaggaaa gcgcactcct gcttttcgat  6480
ttatggtgtg tgcaagtaaa caggtgcatt gctttcaacc tgccatacta gttttaaaaa  6540
ttcactgaaa ttacaaagat acatatatat gcatatatat aatggaaagt ttcccggaat  6600
gcaacaatta gcattttaaa atcatatata ggcatgcaca ttctaaatag tacttttca   6660
tgcttcattg tttctctggc agataatttt actaagaaga aaaatagata ttcgactccc  6720
cttccctaaa caaatccacg ggcagaggct ccagcggagc cgagccccct ggttttctcg  6780
taggccctag acgtgttgc atttatcagt gatgtcaaac gtgctcattt gtcagacata   6840
gctgtaaatg aaaacaatgt gtggcaaaat acaaagtt                          6878
```

SEQ ID NO: 2           moltype = DNA   length = 2656
FEATURE                Location/Qualifiers
source                 1..2656
                       mol_type = genomic DNA
                       organism = Homo sapiens
SEQUENCE: 2

```
gaggcttaa aatctttttt catcttctag ctgtagctcg ggctgcttgt cggcttggcc    60
tccccctccc cccttttgctc tctgcctcgt ctttccccag gacttcgcta ttttgctttt  120
ttaaaaaaag gcaagaaaga actaaactcc ccctccctc tcctccagtc gggctgcacc   180
tctgccttgc actttgcaca gaggtagaga gcgcgcgagg gagagagagg aaagaaaaaa  240
aataataaag agagccaagc agaagaggag gcgagaagca tgaagtgtta actccccgt   300
gccaaggccc gcgccgcccg gacagacgcc cgccgcgcct ccagccccga gcggacgcgg  360
cgcgcgccct gcctgcagcc cgggccggcg aggcgagccc ttccttatgc aaagcgcgca  420
gcggagcggc gagcggggga cgccgcgcac cgggccgggc tcctccagct tcgccgcgc   480
agccaccacc gccgccaccg cagctcgcgg aggatcttcc cgagcctgaa gccgccggct  540
cggcgcgcaa ggaggcgagc gagcaaggag gggcgggcag gacgcagggg gcacattggc  600
gtgagcaggg ggagggagg gcgggcgcgg ggggcgcggg cagggcgggg gggtgtgtgt  660
gtgagcgcgc tcgaggtttt cgggccagcc accgccgcgc aagctagaag cgccccagcc  720
cggcaagctg gctcacccgc tggccaccca gcacagcccg ctggcccctc tcctgcagcc  780
catctggcgg agcggcggcg gcggcggcgg cggcggcagg agaatggcat cagaactggc  840
aatgagcaac tccgacctgc ccaccagtcc cctggccatg cctggcacct gaatactgtta atgacttcgtg 900
tctgatgaag tttgaagtga aaaggaacc ggtggagacc gaccgcatca tcagccagtg    960
cggccgtctc atcgccgggg gctcgctgtc ctccaccccc atgagcacgc cgtgcagctc  1020
ggtgcccct tccccagct tctcggcgcc cagcccgggc tcgggcagcg agcagaaggc   1080
gcacctggaa gactactact ggatgaccgg ctaccccgcag cagctgaacc ccgaggcgct  1140
gggcttgacc cccgaggacg gtgaggagge gctcatcgac aacagccacc agtccaggtg  1200
cggcttcgat ggctacgcgc gcggggcgca gcagctcggc gcggcggccg gggccggtgc  1260
cggcgcctcc ttgggcggca gcgcggagga gatgggccc gccgccgcc tggtgtccgc   1320
cgtgatcgcc gcggccgccg cgcagagcgg cgcgggcccg cactaccacc accaccacca  1380
ccacgccgcc ggccaccacc accacccgac ggccggcgcg cccggcgccg cggcagcgc   1440
ggccgcctcg gccggtggcg ctgggggcgc gggcggcggt ggcccggcca gcgctggggg  1500
```

```
cggcggcggc ggcggcggcg gcggaggcgg cgggggcgcg gcggggcggg ggggcgccct    1560
gcaccgcac  cacgccgccg gcggcctgca cttcgacgac cgcttctccg acgagcagct    1620
ggtgaccatg tctgtgcgcg agctgaaccg gcagctgcgc ggggtcagca aggaggaggt    1680
gatccggctg aagcagaaga ggcggaccct gaaaaaccgc ggctatgccc agtcctgccg    1740
cttcaagagg gtgcagcaga gacacgtcct ggagtcggag aagaaccagc tgctgcagca    1800
agtcgaccac ctcaagcagg agatctccag gctggtgcgc gagagggacg cgtacaagga    1860
gaaatacgag aagttggtga gcagcggctt ccgagaaaac ggctcgagca gcgacaaccc    1920
gtcctctccc gagttttcta actgagcc   cactcgcaag ttggagccat cagtgggata    1980
cgccacattt tggaagcccc agcatcgtgt acttaccagt gtgttcacaa aatgaaattt    2040
gtgtgagagc tgtacattaa aaaaaatcat cattattatt attatttgca gtcatggaga    2100
accacctacc cctgacttct gtttagtctc ctttttaaat aaaaaattact gtgttagaga    2160
agaaggctat taaatgtagt agttaactat gcctcttgtc tgggggtttc atagagaccg    2220
gtaggaaagc gcactcctgc ttttcgattt atggtgtgtg caagtaaaca ggtgcattgc    2280
tttcaacctg ccatactagt tttaaaaatt cactgaaatt acaaagatac atatatatgc    2340
atatatataa tggaaagttt cccggaatgc aacaattagc attttaaaat catatatagg    2400
catgcacatt ctaaatagta ctttttcatg cttcattgtt tctctggcag ataatttttac    2460
taagaagaaa aatagatatt cgactcccct tccctaaaca aatccacggg cagaggctcc    2520
agcggagccg agcccctgg  ttttctcgta ggccctagac ggtgttgcat ttatcagtga    2580
tgtcaaacgt gctcatttgt cagacatagc tgtaaatgaa acaatgtgt  ggcaaaatac    2640
aaagttaaaa aaaaaa                                                    2656

SEQ ID NO: 3            moltype = DNA  length = 6887
FEATURE                 Location/Qualifiers
source                  1..6887
                        mol_type = genomic DNA
                        organism = Homo sapiens
SEQUENCE: 3
gaggctttaa aatcttttt  catcttctag ctgtagctcg ggctgcttgt cggcttggcc      60
tccccctccc cctttgctc  tctgcctcgt cttttcccag gacttcgcta ttttgctttt     120
ttaaaaaaag gcaagaaaga actaaactcc ccctccctc  tcctccagtc gggctgcacc     180
tctgccttgc actttgcaca gaggtagaga gcgcgcgagg gagagagagg aaagaaaaaa     240
aataataaag agagccaagc agaagaggag gcgagaagca tgaagtgtta actccccgt      300
gccaaggccc gcgccgcccg gacagacgcc cgccgcgcct ccagcccga  gcggacgccg     360
cgcgcgccct gcctgcagcc cgggccggcg aggcgagccc ttccttatgc aaagcgcgca     420
gcggagcggc gagcgggga  cgccgcgcac cgggccgggc tcctccagct tcgccgccgc     480
agccaccacc gccgccaccg cagctcgcgg aggatcttcc cgagcctgaa gccgccggct     540
cggcgcgcaa ggaggcgagc gagcaaggag ggggccgggc gagcgaggga gcacattggc     600
gtgagcaggg ggagggagg  gcgggcgcgg ggggcgcggg cagggcgggg gggtgtgtgt     660
gtgagcgcgc tcggaggttt cgggccagcc accgccgcc  aagctagaag ggccccagcc     720
cggcaagctg gctcacccgc tggccaccca gcacagcccg ctggcccctc tcctgcagcc     780
catctgcgcg agcggcggcg gcggcggcgg cggcggcagg agaatggcat cagaactggc     840
aatgagcaac tccgacctgc ccaccagtcc cctggccatg gaatatgtta atgacttcga     900
tctgatgaag tttgaagtga aaaaggaacc ggtggagacc gaccgcatca tcagccagtg     960
cggccgtctc atcgccgggg gctcgctgtc ctccacccc  atgagcacgc cgtgcagctc    1020
ggtgccccct tcccccagct tctcggccgc cagcccgggc tcgggcagcg agcagaaggc    1080
gcacctggaa gactactact ggatgaccgg ctacccgcag cagctgaacc ccgaggcgct    1140
gggcttcagc cccgaggacg cggtcgaggc gctcatcgac aacagccacc agctccaggg    1200
cggcttcgat ggctacgcgc gcggggcgca gcagtggcc  gcggcggccg gggccggtgc    1260
cggcgcctcc ttgggcggca gcggcggagga gatgggcccc gccgccgcc  tggtgtccgc    1320
cgtgatcgcc gcggccgccg gcagagcgg  cgcgggcccg cactaccacc accaccacca    1380
ccacgccgcc ggccaccacc accaccaccc gccgcgccg  ccgggcagcgc                1440
```

-continued

```
gctttgagtt actcagaact tcaacctccc aatgcactga aggcattcct tgtcaaagat  3180
accagaatgg gttacacatt taacctggca acattgaag aactcttaat gttttctttt  3240
taataagaat gacgcccac tttggggact aaaattgtgc tattgccgag aagcagtcta  3300
aaatttattt tttaaaaaga gaaactgccc cattatttt ggtttgtttt attttattt   3360
tatattttt ggcttttggt cattgtcaaa tgtggaatgc tctgggtttc tagtatataa  3420
tttaattcta gttttataa tctgttagcc cagttaaaat gtatgctaca gataaaggaa   3480
tgttatagat aaatttgaaa gagttaggtc tgttagctg tagatttttt aaacgattga   3540
tgcactaaat tgtttactat tgtgatgtta agggggtag agtttgcaag gggactgttt   3600
aaaaaaagta gcttatacag catgtgcttg caacttaagt ataagttggg tatgtgtagt   3660
ctttgctata ccactgactg tattgaaaac caaagtatta agaggggaaa cgcccctgtt   3720
tatatctgta ggggtatttt acattcaaaa atgtatgttt ttttttcttt tcaaaattaa   3780
agtatttggg actgaattgc actaagatat aacctgcaag catataatac aaaaaaaaat   3840
tgcaaaactg tttagaacgc taataaaatt tatgcagtta taaaaatggc attactgcac   3900
agttttaaga tgatgcagat ttttttacag ttgtattgtg gtgcagaact ggattttctg   3960
taacttaaaa aaaatccac agttttaaag gcaataatca gtaaatgtta ttttcaggga   4020
ctgacatcct gtctttaaaa agaaatgaaa agtaaatctt accacaataa atataaaaaa   4080
atcttgtcag ttactttct tttacatatt ttgctgtgca aaattgtttt atatcttgag    4140
ttactaacta accacgcgtg ttgttcctat gtgcttttct ttcattttca attctggtta   4200
tatcaagaaa agaataatct acaataataa acggcatttt ttttgattc tgtactcagt    4260
ttcttagtgt acagtttaac tgggcccaac aacctcgtta aaagtgtaaa atgcatcctt   4320
ttctccagtg gaaggattcc tggaggaata gggagacagt aattcagggt gaaattatag   4380
gctgttttt gaagtgagga ggctggcccc atatactgat tagcaatatt taatatagat   4440
gtaaattatg acctcatttt tttctcccca aagttttcag ttttcaaatg agttgagcca   4500
taattgccct tggtaggaaa aacaaaacaa aacagtggaa ctaggcttcc tgagcatggc   4560
cctacacttc tgatcaggag caaagccatc catagacaga ggagccggac aaatatggcg   4620
catcagaggt ggcttgcgca catatgcatt gaacggtaaa ggagaaacagc gcttgccttt   4680
tcactaaagt tgactatttt tccttcttct cttacacacc gagattttct tgttagcaag   4740
gcctgacaag atttaacata aacatgacaa atcatagttg tttgttttgt tttgcttttc   4800
tctttaacac tgaagatcat ttgtcttaaa taggaaaaag aaaatccact ccttacttcc   4860
atatttccaa gtacatatct ggtttaaact atgttatcaa atcatatttc accgtgaata   4920
ttcagtggag aacttctcta cctggatgag ctagtaatga tttcagatca tgctatcccc   4980
agaaataaaa gcaaaaaata atacctgtgt ggaatatagg ctgtgctttg atttactggt   5040
atttacccca aaataggctg tgtatgggggg ctgacttaaa gatcccttgg aaagactcaa   5100
aactaccttc actagtagga ctcctaagcg ctgacctatt tttaaatgac acaaattcat   5160
gaaactaatg ttacaaattc atgcagtttg cactcttagt catcttcccc tagcacacca   5220
atagaatgtt agacaaagcc agcactgttt tgaaaataca gccaaacacg atgactttg    5280
ttttgttttc tgccgttctt aaaagaaaaa aagataatat tgcaactctg actgaaagac   5340
ttattttaa gaaaacaggt tgtgtttggt gctgctaagt tctggccagt ttatcatctg   5400
gccttcctgc ctatttttta caaaacacga agacagtgtg taacctcgac attttgacct   5460
tcctttatgt gctagtttag acaggctcct gaatcacac ttaattttgc ttaacaaaag   5520
tcttaatagt aaacctcccc tcatgagctt gaagtcaagt gttcttgact tcagatattt   5580
cttttccttt tttttttt tcctcatcac aactaagaga tacacaaact ctgaagaagc    5640
agaaattggag agaatgcttt taacaaaaaa gcatctgatg aagattta ggcaaacatt    5700
ctcaaaataa gagtgatatt ctggatgtag ttattgcagt tatctcatga caaatgaggc   5760
ctggattgga aggaaaatat agttgtgtag aattaagcat tttgatagga atctacaagg   5820
tagttgaata taataagcag gtttgggccc ccaaacttta gaaaatcaaa tgcaaggtgt   5880
ctggcaaaaa tgaggtttga ggtggctggct gtaagagaag gttaactcct agtaaaaggc   5940
atttttagaa ataacaatta ctgaaaactt tgaagtatag tgggagtagc aaacaaatac   6000
atgttttttt tttcttacaa agaactccta aatcctgagt aagtgccatt cattacaata   6060
agtctctaaa tttaaaaaaa aaaaatcat atgaggaaat ctagctttcc cctttacgct   6120
gcgtttgatc tttgtctaaa tagtgttaaa attccttca ttccaattac agaactgagc    6180
ccactcgcaa gttggagcca tcagtgggat acgccacatt ttggaagccc cagcatcgtg   6240
tacttaccag tgtgttcaca aaatgaaatt tgtgtgagag ctgtacatta aaaaaaatca   6300
tcattattat tattatttgc agtcatggag aaccacctac ccctgacttc tgtttagtct    6360
cctttttaaa taaaaattac tgtgttagag aagaaggcta ttaagtgtag tagttaacta   6420
tgcctcttgt ctgggggttt catagagacc ggtaggaaag cgcactcctg cttttcgatt   6480
tatggtgtgt gcaagtaaac aggtgcattg ctttcaacct gccatactag ttttaaaaat   6540
tcactgaaat tacaaagata catatatg catatatata atggaaagtt tcccggaatg    6600
caacaattag cattttaaaa tcatatatag gcatgcaact tctaaatagt acttttttcat   6660
gcttcattgt ttctctggca gataattta ctaagaagaa aaatagatat tcgactcccc    6720
ttccctaaac aaatccacgg gcagaggctc cagcggagcc gagcccctg gttttctcgt   6780
aggccctaga cggtgttgca tttatcagtg atgtcaaacg tgctcatttg tcagacatag   6840
ctgtaaatga aaacaatgtg tggcaaaata caaagttaaa aaaaaa            6887
```

| | | |
|---|---|---|
| SEQ ID NO: 4 | moltype = AA  length = 400 | |
| FEATURE | Location/Qualifiers | |
| source | 1..400 | |
| | mol_type = protein | |
| | organism = Homo sapiens | |

SEQUENCE: 4

```
MASELAMSNS DLPTSPLAME YVNDFDLMKF EVKKEPVETD RIISQCGRLI AGGSLSSTPM    60
STPCSSVPPS PSFSAPSPGS GSEQKAHLED YYWMTGYPQQ LNPEALGFSP EDAVEALISN  120
SHQLQGGFDG YARGAQQLAA AAGAGAGASL GGSGEEMGPA AAVVSAVIAA AAAQSGAGPH  180
YHHHHHHAAG HHHHPTAGAP GAAGSAAASA GGAGGAGGGG PASAGGGGGG GGGGGGGGAA  240
GAGGGALHPHH AAGGLHFDDR FSDEQLVTMS VRELNRQLRG VSKEEVIRLK QKRRTLKNRG  300
YAQSCRFKRV QQRHVLESEK NQLLQQVDHL KQEISRLVRE RDAYKEKYEK LVSSGFRENG  360
SSSDNPSSPE FFITEPTRKL EPSVGYATFW KPQHRVLTSV                        400
```

| | | |
|---|---|---|
| SEQ ID NO: 5 | moltype = AA  length = 373 | |

| FEATURE | Location/Qualifiers |
|---|---|
| source | 1..373<br>mol_type = protein<br>organism = Homo sapiens |

SEQUENCE: 5
```
MASELAMSNS DLPTSPLAME YVNDFDLMKF EVKKEPVETD RIISQCGRLI AGGSLSSTPM   60
STPCSSVPPS PSFSAPSPGS GSEQKAHLED YYWMTGYPQQ LNPEALGFSP EDAVEALISN  120
SHQLQGGFDG YARGAQQLAA AAGAGAGASL GGSGEEMGPA AAVVSAVIAA AAAQSGAGPH  180
YHHHHHHAAG HHHHPTAGAP GAAGSAAASA GGAGGAGGGG PASAGGGGGG GGGGGGGGAA  240
GAGGALHPHH AAGGLHFDDR FSDEQLVTMS VRELNRQLRG VSKEEVIRLK QKRRTLKNRG  300
YAQSCRFKRV QQRHVLESEK NQLLQQVDHL KQEISRLVRE RDAYKEKYEK LVSSGFRENG  360
SSSDNPSSPE FFM                                                    373
```

| SEQ ID NO: 6 | moltype = RNA length = 19 |
|---|---|
| FEATURE | Location/Qualifiers |
| source | 1..19<br>mol_type = other RNA<br>note = c-MAF specific siRNA<br>organism = synthetic construct |

SEQUENCE: 6
```
acggctcgag cagcgacaa                                               19
```

| SEQ ID NO: 7 | moltype = RNA length = 19 |
|---|---|
| FEATURE | Location/Qualifiers |
| source | 1..19<br>mol_type = other RNA<br>note = c-MAF specific siRNA<br>organism = synthetic construct |

SEQUENCE: 7
```
cttaccagtg tgttcacaa                                               19
```

| SEQ ID NO: 8 | moltype = RNA length = 20 |
|---|---|
| FEATURE | Location/Qualifiers |
| source | 1..20<br>mol_type = other RNA<br>note = c-MAF specific siRNA<br>organism = synthetic construct |

SEQUENCE: 8
```
tggaagacta ctactggatg                                              20
```

| SEQ ID NO: 9 | moltype = RNA length = 20 |
|---|---|
| FEATURE | Location/Qualifiers |
| source | 1..20<br>mol_type = other RNA<br>note = c-MAF specific siRNA<br>organism = synthetic construct |

SEQUENCE: 9
```
atttgcagtc atggagaacc                                              20
```

| SEQ ID NO: 10 | moltype = RNA length = 20 |
|---|---|
| FEATURE | Location/Qualifiers |
| source | 1..20<br>mol_type = other RNA<br>note = c-MAF specific siRNA<br>organism = synthetic construct |

SEQUENCE: 10
```
caaggagaaa tacgagaagt                                              20
```

| SEQ ID NO: 11 | moltype = RNA length = 20 |
|---|---|
| FEATURE | Location/Qualifiers |
| source | 1..20<br>mol_type = other RNA<br>note = c-MAF specific siRNA<br>organism = synthetic construct |

SEQUENCE: 11
```
acaaggagaa atacgagaag                                              20
```

| SEQ ID NO: 12 | moltype = RNA length = 20 |
|---|---|
| FEATURE | Location/Qualifiers |
| source | 1..20<br>mol_type = other RNA<br>note = c-MAF specific siRNA<br>organism = synthetic construct |

SEQUENCE: 12
```
acctggaaga ctactactgg                                              20
```

| SEQ ID NO: 13 | moltype = DNA length = 13878 |
|---|---|
| FEATURE | Location/Qualifiers |
| source | 1..13878 |

```
                      mol_type = genomic DNA
                      organism = Homo sapiens
SEQUENCE: 13
aactatatat taaacacctc cggtctgaga ggccgtgttg ggtgtctttg tcaggtgaag    60
aaagagaaga aggctggtac accttcccag gaattctcac tgaagaaaac atctggattt   120
tttacatctc ttgtgcaaaa caaacaaaga tttcattaag tgatgtatat tgttttccaa   180
ggaagaaacc tgcagagaca aaaacaaata agcaaataat tgaaacaaaa atatgataaa   240
cccccaaatt cttccagtgc taatttactt gttatcatgg ttctctacaa aggcagagat   300
cactaattac aggttttttcc agaattcaca tttcacgtca agatcatcca atccaaacag   360
tgtacggaaa gcctagggcc ttcttcactt tgcccctac cccaccctac acacacgccc   420
ccatctaaat gatacccttg gaaagaaacc tacacatctc atttgtctat attttgcttc   480
ctccctcgcc tcccggtaac caaatgtgag ttgttctcta actgcactgg agaatcagaa   540
tttattgtac atatgtttgt gttccactta ataaaaaaac ctatattta agataaactt   600
tgttagtaat tcatgaggta agtgactatt tatgctaatc aggcagaaat atattctcaa   660
gcataatgca ttcataaaat ttgaatgtaa aatgttcaat tatgaagtaa atacaggtaa   720
tgcaaataat aaaattacctc taataaaaat tataaaagat gtgccttgaa agagagagcg   780
gctttaactt acaactgtga attgcttaaa gagaaagaa ttaataaatg ctgaattact   840
ctgatgatta tttagcacat aattcaccta ttcataacga ctcctagtaa tcagactgtt   900
gtttcacatc ctccaacatg aggcaagact gtttcctcag caattttgcc cttatcagat   960
tatctcgtct gattctatta attttcttcc atgaatctgc taacagtgat ttgtgattta  1020
cttaccctgc taactgaaga ctgttaaaag gatttatcta acactggacc taagaacagt  1080
gtacgccttga tcgttcagtt actctgaaga actcttttcc aaatcaattt agttggtttc  1140
atagtgaaat ttagtggaca ctggttagtt ctgccccata aaatcagccc ctaaacaaag  1200
agtccagaca ccatacctga tgcatcccat tctattcaga ttatgatgt ctgattccaa  1260
catgatatat ttgagttgct ataactcaca atcggggaaa atatattcct ttaagctttt  1320
aatctttgta atttggacat gaacagggt tttgttttc atttttgcat gaagtcatta  1380
tgtatgtact gacgtgaaac tataattgtg tttctgatgt tactgtgtca caatattcta  1440
tgcgatgtaa cccatgtcct cctccccctc acaaatctcc tataaatatt cattgctttc  1500
aaaaacttta atactactgg tccgaattgg tcaataatga caaatgcatg gtttctaaat  1560
tactgtatat tgttctacag agattactag agtatatata gcaaggggat gttaagcagt  1620
aagaaaacac agttcacatt gtatttggat tagattggct tggatagaag tgaaacaaac  1680
aatgttagca aagaagtcta aagacatgtg gcccactgta attgtacaga atcaaaaacc  1740
tgaatagtac tcattaaaat gagagagctc aattgttata aagaaatgc tgctaacaga  1800
gaactgtaaa tgtttagaca cccctgtgaa tcactaaata ataatgtaaa aaggataaaa  1860
atgagaatta agttataagc ctgagagcat tactgctaca catctaaaaa aataattctg  1920
atcctctctt tttttttcc aagagaaaat gggcgactat aaaagacctt gcaataagag  1980
aaataaaaat accatgtctt cacagcagtg tacataaata aaccataaaa atgtgcagat  2040
aataatatat ttagctgccc aaacatgggc atttaatttc tagaaatgat atataacaat  2100
gtaacaatta gatactcagc catgaatgtg tatggcacag tcttcatcat tagcaaactt  2160
tgtgtataaa atattattta ttatttatta taatactgct ttcagaggca atgatcatac  2220
cttacagctt ttaacacaaa tatgatgcaa aaggattaaa agtatatcat aaacaaacaa  2280
taaattcttt ctaaatacac ttaaattcat attttacatg aaaaatataa acttcctaca  2340
tttgtgacta ctgactttta aaaagaccta gaaaactatt gttacgggca atgttaaatg  2400
acataatgct tatgtaatgg aaagtgtgga ttttcctcta aataaactat aatcccttaa  2460
cttcattact agggaaaata ttgttaaaga gaaggaaagc aagggaattc tgctaggttg  2520
cataaatatt gacataatct tcactctttc ttccccaaac tggtaataga catagtttat  2580
tccaccaac aaatgctct tataagacca aaactaccct tattaacaac ttctctgcag  2640
tcacgatgaa aagaaacact acttgtctga aaaataccga cagcgctgcc cttttcagat  2700
tagggtgtgc ctacgaatct tttgggaagt cttccattaa ggattcctgg gtttgctgaa  2760
actgaagtct actaggatca gagaaattaa cacaggtcta atatggtgca aggaacgagt  2820
gagagacacc tgaggttata aatagacaaag catgctgcgg ggtggggaag accattctga  2880
agtgcaatgt tcaagacgct ggcttaatat atgactaagt gtcagaagtc aggttttctg  2940
agaattactt tccagataaa caactttata gcactgcact taatcttact tactagagac  3000
atctcattta tcactgaatt acaagtaact ttaatcctat tgatattgcc ataaagcccg  3060
ttgaaaatcc atcctggcac ttttaaaggg tttggggccc tgttacatgg ggatcctctt  3120
gcaaaggtct cagccagaaa ttacacccccg agggtgtctg tatccccctgg cctctttgtc  3180
aacaatcaag gagaagagga ggggcaaaaa tgatctctgc atctgccagc actttcttcg  3240
gcccctttcc tatagggtcg ggttctccca cttcagtcaa actaactttg tgtgtctctt  3300
tcctcctccc acactgggta accagctgct tttcacttca tcgacaaaac tggacacgga  3360
tcaatttcaa ctgacctttg ccgaaggtg gcgctgttga ggtaaaaacc aactcgctcc  3420
aacaatagtt tccactcttc gatccttttg caggcttttc agaatttttt tttttttta  3480
atgcaccctc ctagccgtctc cccttctca taaagtaaaa taaatacgat taaaacacc  3540
aaatgcattt cattaattga aggaatcaac agtcccaact tctaagcaga cgggctggtc  3600
ttccaaaggc tgggtcggtt tcaggagctt tctctccaaa taatctctg cttcttcgac  3660
ttgcctatcg ctttaaaatc ttagaaacag agttagttgt tggtttcctt cttttttctt  3720
tttcttttt atttctttt tgcataaact tttagagaat caatctagaa atttgaacta  3780
cttattagca tttgcaactg ggggtggggg gagcagcctc ccccacccca ccccccactc  3840
tgcgtttccg gactagttcc agaaaccgcg gtttaaaatt taaccccttcg agggtagctg  3900
gtgagggctg gggtattgtt tttccccccctt gctccctgcc acgatcaagt gcgaaataat  3960
taaaggaaac gtaaagtgc aaagggcgcg cctgaccctg ataaacagag gtcagatttc  4020
gtaagggac gggtgagtgt gagtgtgtgt gtgtttgtgt gtgtgtgtgt aagagagaga  4080
gagagcgagc gcgcaatatg agtctcaaag gccaaactcc ggccagtcag gagccggaag  4140
gctgagcccg gctgacctga ctttgagctt cccccggagtt atctcgcata ggcgctcgct  4200
ctgtccaagg gcacgcgacg ccagcgggca gccggtctc gtgaagaatg gcctctaaac  4260
aacttatttt acctcgttgt aaagagaggg ataaaatggg cttttcctct ccacggatgc  4320
ccagccttct gggcaggcgc atggccgggc ggcgcccagc ccgcagcccc gatccggaca  4380
ccccactgca tccctccctt cccggtccct tcccgcacg ggcgcccgag agacggacaa  4440
agagttgggg ccaagtttga gcgccgggca cggccaggct cagggaagga aggtccccgg  4500
cagacaccctg ggtaccagag ttggtgcgag gaggaaaagc tgggaggcga attcacaatc  4560
```

```
ctgggggtgg agggcaggca ggggagggga atcaggccaa tcccagccga gtgagccccc    4620
agcgagctgg ggctccggat ggggaggcct tctcgcgctc caaagaaaag caaaccgccc    4680
tcccaggtcc gcccggattg ccgaagcccc tctggaaaaa ctccttcccc tcttacacca    4740
aactttgcgc cgggcctcgt tccctccgg gtaggcagcg cgcaggaag ggttaagcca      4800
gcccgtccca gctgacagtc agctgattgg gccctgattg acagctccga aaagtttcct    4860
tgtttctata ctattatgct aatcgcggcc gctctcgccg cctcccattg gcccggagtg    4920
ccagtcaatt tctcatttgg acctgacgtc acgagtgcta taaaactcag caattgcttt    4980
aaaactcttct tgctggatca gaggctttaa aatctttttt catcttctag ctgtagctcg   5040
ggctgcttgt cggcttggcc tcccctccc cctttgctc tctgcctcgt cttccccag       5100
gacttcgcta ttttgctttt ttaaaaaaag gcaagaaaga actaaactcc cccctccctc    5160
tcctccagtc gggctgcacc tctgccttgc actttgcaca gaggtagaga gcgcgcgagg    5220
gagagagagg aaagaaaaaa aataataaag agagccaagc agaagaggag gcgagaagca    5280
tgaagtgtta actccccgt gccaaggccc gcgccgccg gacagacgcc cgccgcgcct      5340
ccagccccga gcggaccgcg cgccgccct gcctgccgca cgggccggcg aggcgagccc     5400
ttccttatgc aaagcgcgca gcggagcggc gagcgggga cgccgcgcac cgggccgggc    5460
tcctccagct tcgccgccgc agccaccacc gccgccaccg cagctcgcgg aggatcttcc    5520
cgagcctgaa gccgccggct cggcgcgcaa ggaggcgagc gagcaaggag gggccggggc    5580
gagcgaggga gcacattggc gtgagcaggg gggaggagg gggcgcagg ggggcgcggg     5640
cagggcgggg gggtgtgtgt gtgagcgcgc tcggaggttt cgggccagcc accgccgcgc    5700
aagctagaag cgcccagcc cggcaagctg gctcacccgc tggccaccca gcacagcccg    5760
ctggcccctc tcctgcagcc catctggcgg agcggcggcg gcgcggcgg cggcggcagg    5820
agaatggcat cagaactggc aatgagcaac tccgacctgc ccaccagtcc cctggccatg    5880
gaatatgtta atgacttcga tctgatgaag tttgaagtga aaaaggaacc ggtgagacc     5940
gaccgcatca tcagccagtg cggccgtctc atcgccgggg gctcgctgtc ctccaccccc    6000
atgagcacgc cgtgcagctc ggtgcccct tcccccagct tctcggcgcc cagcccgggc    6060
tcgggcagcg agcagaaggc gcacctggaa gactactact ggatgaccgg ctacccgacg    6120
cagctgaacc ccgaggcgct gggcttcagc cccgaggacg cggtcgaggc gctcatcagc    6180
aacagccacc agctccaggg cggcttcgat ggctacgcgc gcggggcgca gcagctggcc    6240
gcggcggccg gggccggtgc cggcgcctcc ttgggcggca gcggcgagga gatgggcccc    6300
gccgccgcg tggtgtccgc cgtgatcgcc gcggccgcc gcagagcgg cgcggccgcg     6360
cactaccacc accaccacca ccacgccgcc ggccaccacc accacccgac ggccggcgcg    6420
cccggcgccg cggcagcgc ggccgcctcg gccgtggcg ctgggggcgc gggcggcggt     6480
ggcccggcca gcgctggggg cggcggcggc ggcggcggcg gcggaggcgg cggggcgcg    6540
gcgggggcgg ggggcgccct gcaccgccg cacgccgccg gcggcctgca cttcgacgcc    6600
cgcttctccg acgagcagct ggtgaccatg tctgtgccg agctgaaccg gcagctgcgc    6660
ggggtcagca aggaggaggt gatccggctg aagcagaaga ggcggaccct gaaaaaccgc    6720
ggctatgccc agtcctgccg cttcaagagg gtgcagcaga cacgtcct ggagtcggag     6780
aagaaccagc tgctgcagca agtcgaccac ctcaagcagg agatctccag gctggtgcgc    6840
gagaggacg cgtacaagga gaaatacgag aagttggtga gcagcggctt ccgagaaaac    6900
ggctcgagca gcgacaaccc gtcctctccc gagttttca tgtgagtctg acacgcgatt    6960
ccagctagcc accctgataa gtgctccgcg ggggtccggc tcgggtgtgg gcttgctagt    7020
tctagagcca tgctcgccac cacctcacca ccccaccc caccgagttt ggccccttg      7080
gcccctaca cacacaaa cccgcacgca cacaccaca acacacac acacacac            7140
acacccaca ccctgctcga gtttgtggtg gtggtggctg ttttaaactg ggagagggat    7200
gggtgtctgg ctcatggatt gccaatctga aattctccat aacttgctag cttgttttt    7260
tttttttttt acaccccccc gccccacccc cggacttgca caatgttcaa tgatctcagc   7320
agagttcttc atgtgaaacg ttgatcaccct ttgaagcctg catcattcac atatttttt    7380
ttcttcttcc ccttcagttc atgaactggt gttcatttc tgtgtgtgtg tgtgttttat    7440
tttgtttgga ttttttttt taattttact tttagagctt gctgtgttgc ccacttttt     7500
tccaacctcc accctcactc cttctcaacc catctcttcc gagatgaaag aaaaaaaaaa    7560
gcaaagtttt tttttttctt cctgaagttct tcatgtgaga ttgagcttgc aaaggaaaaa   7620
aaaatgtgaa atgttataga cttgcagcgt gccgagttcc atcgggtttt ttttttagca    7680
ttgttatgct aaaatagaga aaaaaatcct catgaacctt ccacaatcaa gcctgcatca    7740
accttctggg tgtgacttgt gagttttggc cttgtgatgc caaatctgag agtttagtct    7800
gccattaaaa aaactcattc tcatctcatg cattattatg cttgctactt tgtcttagca    7860
acaatgaact ataactgttt caaagacttt atggaaaaga gacattatat taataaaaaa    7920
aaaaagcctg catgctggac atgtatggta aattatttt ttcctttttt tttccttttg     7980
gcttggaaat ggacgttcga agacttatag catggcattc atacttttgt tttattgcct    8040
catgactttt ttgagtttag aacaaaacag tgcaaccgta gagccttctt cccatgaaat    8100
tttgcatctg ctccaaaact gctttgagtt actcagaact tcaacctccc aatgcactga    8160
aggcattcct tgtcaaagat accagaatgg gttacacatt taacctggca aacattgaag    8220
aactcttaat gttttctttt taataagaat gacgcccac tttggggact aaaattgtgc     8280
tattgccgag aagcagtcta aaatttattt tttaaaaga gaaactgccc cattatttt     8340
ggtttgtttt atttttttt tatatttttt ggctttttgt cattgtcaaa tgtggaatgc    8400
tctgggtttc tagtatataa tttaattcta gtttttaaa tctgttagcc cagttaaaat    8460
gtatgctaca gataaaggaa tgttatagat aaatttgaaa gagttaggtc tgtttagctg    8520
tagatttttt aaacgattga tgcactaaat tgttactat tgtgatgtta aggggggtag    8580
agtttgcaag gggactgttt aaaaaaaagta gcttatacag catgtgcttg caacttaaat    8640
ataagttggg tatgtgtagt ctttgctata ccactgactg tattgaaaac caaagtttg    8700
agaggggaaa cgcccctgtt tatatctgta ggggtatttt acattcaaaa atgtatgttt    8760
ttttttcttt tcaaaattaa agtatttggg actgaattgc actaagatat aacctgcaag    8820
catataatac aaaaaaaaat tgcaaaactg tttagaacgc taataaaatt tatgcagtta    8880
taaaaatggc attactgcac agttttaaga tgatgcagat ttttttacag ttgtattgtg    8940
gtgcagaact ggatttttctg taacttaaaa aaaaatccac agttttaaag gcaataatca    9000
gtaaatgtta ttttcaggga ctgacatcct gtctttaaaa agaaatgaaa agtaaatctt    9060
accacaataa atataaaaaa atcttgtcag ttacttttct tttacatatt ttgctgtgca    9120
aaattgtttt atatcttgag ttactaacta accacgcgtg ttgttcctat gtgcttttct    9180
ttcatttca attctggtta tatcaagaaa agaataatct acaataataa acggcatttt    9240
tttttgattc tgtactcagt ttcttagtgt acagtttaac tgggcccaac aacctcgtta    9300
```

```
aaagtgtaaa atgcatcctt ttctccagtg gaaggattcc tggaggaata gggagacagt  9360
aattcagggt gaaattatag gctgtttttt gaagtgagga ggctggcccc atatactgat  9420
tagcaatatt taatatagat gtaaattatg acctcatttt tttctcccca aagttttcag  9480
ttttcaaatg agttgagcca taattgccct tggtaggaaa aacaaaacaa aacagtggaa  9540
ctaggcttcc tgagcatggc cctacacttc tgatcaggag caaagccatc catagacaga  9600
ggagccggac aaatatggcg catcagaggt ggcttgcgca catatgcatt gaacggtaaa  9660
gagaaacagc gcttgccttt tcactaaagt tgactatttt tccttcttct cttacacacc  9720
gagattttct tgttagcaag gcctgacaag atttaacata aacatgacaa atcatagttg  9780
tttgttttgt tttgcttttc tctttaacac tgaagatcat ttgtcttaaa taggaaaaag  9840
aaaatccact ccttacttcc atatttccaa gtacatatct ggtttaaact atgttatcaa  9900
atcatatttc accgtgaata ttcagtggag aacttctcta cctggatgag ctagtaatga  9960
tttcagatca tgctatcccc agaaataaaa gcaaaaaata atacctgtgt ggaatatagg 10020
ctgtgctttg atttactggt atttacccca aaataggctg tgtatggggg ctgacttaaa 10080
gatccctgg aaagactcaa aactaccttc actagtagga ctcctaagcg ctgacctatt 10140
tttaaatgac acaaattcat gaactaatg ttacaaattc atgcagtttg cactcttagt 10200
catcttcccc tagcacacca atagaatgtt agacaaagcc agcactgttt tgaaaataca 10260
gccaaacacg atgactttg ttttgttttc tgccgttctt aaaagaaaaa aagataatat 10320
tgcaactctg actgaaagac ttattttaa gaaaacaggt tgtgtttggt gctgctaagt 10380
tctggccagt ttatcatctg gccttcctgc ctatttttta caaaacacga agacagtgtg 10440
taacctcgac attttgacct tccttatgt gctagtttag acaggctcct gaatccacac 10500
ttaattttgc ttaacaaaag tcttaatagt aaacctcccc tcatgagctt gaagtcaagt 10560
gttcttgact tcagatattt cttttccttt tttttttttt tcctcatcac aactaagaga 10620
tacacaaact ctgaagaagc agaaatggag agaatgcttt taacaaaaaa gcatctgatg 10680
aaagatttta ggcaaacatt ctcaaaataa gagtgatatt ctggatgtag ttattgcagt 10740
tatctcatga caaatgaggc ctggattgga aggaaaatat agttgtgtag aattaagcat 10800
tttgatagga atctacaagg tagttgaata taataagcag gtttgggccc ccaaacttta 10860
gaaaatcaaa tgcaaaggtg ctggcaaaaa tgaggtttga gtggctggct gtaagagaag 10920
gttaactcct agtaaaaggc attttagaa ataacaatta ctgaaaactt tgaagtatag 10980
tgggagtagc aaacaaatac atgtttttt ttcttacaa agaactccta aatcctgagt 11040
aagtgccatt cattacaata agtctctaaa tttaaaaaaa aaaaaatcat atgaggaaat 11100
ctagctttcc cctttacgct gcgtttgatc tttgtctaaa tagtgttaaa attccttttca 11160
ttccaattac agaactgagc ccactcgcaa gttggagcca tcagtgggat acgccacatt 11220
ttggaagccc cagcatcgtg tacttaccag tgtgttcaca aaatgaaatt tgtgtgagag 11280
ctgtacatta aaaaaaatca tcattattat tattatttgc agtcatggag aaccacctac 11340
ccctgacttc tgtttagtct ccttttttaaa taaaaattac tgtgttagag aagaaggcta 11400
ttaaatgtag tagttaacta tgcctcttgt ctgggggttt catagagacc ggtaggaaag 11460
cgcactcctg cttttcgatt tatggtgtgt gcaagtaaac aaggtgcattg ctttcaacct 11520
gccatactag ttttaaaaat tcactgaaat tacaaagata catatatag catatatata 11580
atggaaagtt tcccggaatg caacaattag cattttaaaa tcatatatag gcatgcacat 11640
tctaaaatagt acttttttcat gcttcattgt ttctctggca gataatttta ctaagaagaa 11700
aaatagatat tcgactcccc ttccctaaac aaatccacgg gcagaggctc cagcggagcc 11760
gagcccctg gttttctcgt aggccctaga cggtgttgca tttatcagtg atgtcaaacg 11820
tgctcatttg tcagacatag ctgtaaatga aaacaatggt tggcaaaata caagttagt 11880
taaatacaca ccctctgtgt gattttttgc tcccttttct ttttttgctcc tactcaaaaa 11940
aaaaaaaatc acctccttta catttccctg gcttcttgca tgtttccctt ttcaaaaacc 12000
atgtaataat tttttacaat gtatctgaca cattaatata ttgacatcaa ataggcagac 12060
attctacttt tgcctggcaa taaaatctgc tacggagaca tcattttctc actgtctcaa 12120
agccataact acctgggagt cttttcaacac agacccctcc gatgggaaat gctgtttatt 12180
actgaatgca ggatgctcac gctctgatct ttttctccctt gtgccttttac cccagtcatt 12240
tttacttagc aacaccaatt ctagatactt ctgttctgaa gtagaaccac ccccttgcca 12300
cactgccagt tttcctgcta aaagcagtgg acagaagaca gatcatgtgc accctcacaa 12360
acatggcaca cagctgtctc ggtagctgca ttcccagcat gtcctggtct aaatatctag 12420
agttgcctat gacacgttca aaggttccca agcacagtac attgggaggc ttttgctgct 12480
gtggccgttg ttttcgttta ggccaactta cttccgtatt cacatactct ggctttacg 12540
aaatacactc ctccagtcta ctaggccaat caatatattt aaaagtctga ttgccacata 12600
agtctctctc tctctcttttt tgtttttgt ttgtttgttt ttttctgttt tggctgccag 12660
tagttaaaga ctgagatagg ttggaagact aaaatacagg agtacatgag tgacaacctt 12720
cagccgtctg atttccatgc cggtaaaaca cacaaccaag ctcttcttag cgctgctaat 12780
ataacattc actaagaggg aataggaagt gagatttacc agcttcactt tgctgatttg 12840
caaggttccc cactacgatt cactgtcatt tgattttga aaaataattt tgtccgtctc 12900
tttgaagaaa tgtcttagtt ctttttatttt gtttgtttgg tttttttttag agaagttta 12960
tctgcagtga taggctacaa ttttatctc cgctgattat ttgtcaggat gctgaatgaa 13020
taatttggtc ctgtgccttc cttgttgttc tgaggaaaat aagagaaact tggaagtttg 13080
tttcactctt agcccatcct aaatctaaaa gaagtatgct cagtccagg caggccagtg 13140
agtagttata aaggaggtgg tccaggtcca gccacctcaa tcaggatttg tttgtttga 13200
agcatttgct taaagcgga gcaagagtct taacccaact tgccataaca ctgctttcct 13260
cgcttttgat gtaaatcttc aaaattcaga catcaaacag ccccagaaaa gggaattct 13320
ctccaggcat tgctccgccc cagctcctga acaaaccgag ctctgtctag cattttttc 13380
cctagcgggg gtaggggaca gggtgagaga atttcagtct cccagcgctgt ctcatgattg 13440
ttagggcata aagaaacaca gtcctgccac aaatttgggag catctttacc ctttagagag 13500
aaacaaaaca aaactaaaca aacaaatcaa attgctttgc atgaaggcgt agcaaataaa 13560
atctcggcct ccctgttccc tgcaccattt gtaggaggtg agaaatgagg gaaacaagag 13620
aaggggaac tttaaaagcg ggaggcccag aaataatccc tgttaccagt ctgaatttca 13680
cctgctcgt ggctaacgtc agactagtg tgcatgtatg ccagaagtaa actaggctcg 13740
gctgtccatt tctttaaaat atgttccatt gtttcctttt tgaaaacaat ttgggggact 13800
aaacccaaat ggagagattt gaggaaatcg ttaatgtctt aacattgag tatatttata 13860
aatgtatcag tctgtgat                                              13878

SEQ ID NO: 14         moltype = AA    length = 455
```

```
FEATURE                 Location/Qualifiers
REGION                  1..132
                        note = Variable Heavy Chain
REGION                  133..138
                        note = Start of constant region
REGION                  317..416
                        note = Variant
source                  1..455
                        mol_type = protein
                        note = INB-1-11-8 (H1) Heavy Chain
                        organism = synthetic construct
SEQUENCE: 14
METGLRWLLL VAVLKGVQCQ SLEESGGRLV TPGTPLTLTC TASGFSLNNY PMTWVRQAPG    60
KGLDYIGVIN NSGETAYATW AKRRFTISRT STTLYLKIAS PTIEDTATYF CARGGPVSSD   120
MWGPGTLVIV SSGQPKAPSV FPLAPCCGDT PSSTVTLGCL VKGYLPEPVT VTWNSGTLTN   180
GVRTFPSVRQ SSGLYSLSSV VSVTSSSQPV TCNVAHPATN TKVDKTVAPS TCSKPTCPPP   240
ELLGGPSVFI FPPKPKDTLM ISRTPEVTCV VVDVSQDDPE VQFTWYINNE QVRTARPPLR   300
EQQFNSTIRV VSTLPIAHQD WLRGKEFKCK VHNKALPAPI EKTISKARGQ PLEPKVYTMG   360
PPREELSSRS VSLTCMINGF YPSDISVEWE KNGKAEDNYK TTPAVLDSDG SYFLYSKLSV   420
PTSEWQRGDV FTCSVMHEAL HNHYTQKSIS RSPGK                              455

SEQ ID NO: 15           moltype = AA  length = 132
FEATURE                 Location/Qualifiers
source                  1..132
                        mol_type = protein
                        note = INB-1-11-8 (H1) Variable Heavy Chain
                        organism = synthetic construct
SEQUENCE: 15
METGLRWLLL VAVLKGVQCQ SLEESGGRLV TPGTPLTLTC TASGFSLNNY PMTWVRQAPG    60
KGLDYIGVIN NSGETAYATW AKRRFTISRT STTLYLKIAS PTIEDTATYF CARGGPVSSD   120
MWGPGTLVIV SS                                                       132

SEQ ID NO: 16           moltype = AA  length = 236
FEATURE                 Location/Qualifiers
REGION                  1..133
                        note = Variable Light Chain
REGION                  134..139
                        note = Start of constant region
REGION                  146..149
                        note = Variant
source                  1..236
                        mol_type = protein
                        note = INB-1-11-8 (L4) Light Chain
                        organism = synthetic construct
SEQUENCE: 16
MDTRAPTQLL GLLLLWLPGA TFAQVLTQTA SPVSAVVGGT VTINCQSSQS VYRGDWLAWY    60
QQRPGQPPKL LIYGASTLAS GVPSRFKGSG SGTHFTLTIS DLDCDDAATY YCAGGFSGHI   120
YDFGGGTEVV VKGDPVAPTV LIFPPAADQV ATGTVTIVCV ANKYFPDVTV TWEVDGTTQT   180
TGIENSKTPQ NSADCTYNLS STLTLTSTQY NSHKEYTCKV TQGTTSVVQS FNRGDC       236

SEQ ID NO: 17           moltype = AA  length = 133
FEATURE                 Location/Qualifiers
source                  1..133
                        mol_type = protein
                        note = INB-1-11-8 (L4) Variable Light Chain
                        organism = synthetic construct
SEQUENCE: 17
MDTRAPTQLL GLLLLWLPGA TFAQVLTQTA SPVSAVVGGT VTINCQSSQS VYRGDWLAWY    60
QQRPGQPPKL LIYGASTLAS GVPSRFKGSG SGTHFTLTIS DLDCDDAATY YCAGGFSGHI   120
YDFGGGTEVV VKG                                                      133

SEQ ID NO: 18           moltype = AA  length = 13
FEATURE                 Location/Qualifiers
source                  1..13
                        mol_type = protein
                        note = CDR1
                        organism = synthetic construct
SEQUENCE: 18
QSSQSVYRGD WLA                                                       13

SEQ ID NO: 19           moltype = AA  length = 7
FEATURE                 Location/Qualifiers
source                  1..7
                        mol_type = protein
                        note = CDR2
                        organism = synthetic construct
SEQUENCE: 19
GASTLAS                                                               7
```

```
SEQ ID NO: 20           moltype = AA  length = 10
FEATURE                 Location/Qualifiers
source                  1..10
                        mol_type = protein
                        note = CDR3
                        organism = synthetic construct
SEQUENCE: 20
AGGFSGHIYD                                                                        10

SEQ ID NO: 21           moltype = AA  length = 5
FEATURE                 Location/Qualifiers
source                  1..5
                        mol_type = protein
                        note = CDR1
                        organism = synthetic construct
SEQUENCE: 21
NYPMT                                                                              5

SEQ ID NO: 22           moltype = AA  length = 16
FEATURE                 Location/Qualifiers
source                  1..16
                        mol_type = protein
                        note = CDR2
                        organism = synthetic construct
SEQUENCE: 22
VINNSGETAY ATWAKR                                                                 16

SEQ ID NO: 23           moltype = AA  length = 8
FEATURE                 Location/Qualifiers
source                  1..8
                        mol_type = protein
                        note = CDR3
                        organism = synthetic construct
SEQUENCE: 23
GGPVSSDM                                                                           8

SEQ ID NO: 24           moltype = AA  length = 18
FEATURE                 Location/Qualifiers
source                  1..18
                        mol_type = protein
                        organism = Homo sapiens
SEQUENCE: 24
EQKAHLEDYY WMTGYPQQ                                                               18
```